United States Patent
Wang et al.

(10) Patent No.: US 11,730,797 B2
(45) Date of Patent: Aug. 22, 2023

(54) CS1 TARGETED CHIMERIC ANTIGEN RECEPTOR-MODIFIED T CELLS

(71) Applicant: City of Hope, Duarte, CA (US)

(72) Inventors: Xiuli Wang, Duarte, CA (US); Stephen J. Forman, Duarte, CA (US)

(73) Assignee: City of Hope, Duarte, CA (US)

( * ) Notice: Subject to any disclaimer, the term of this patent is extended or adjusted under 35 U.S.C. 154(b) by 241 days.

(21) Appl. No.: 16/992,361

(22) Filed: Aug. 13, 2020

(65) Prior Publication Data
US 2021/0170001 A1     Jun. 10, 2021

Related U.S. Application Data

(63) Continuation of application No. 15/533,153, filed as application No. PCT/US2015/064303 on Dec. 7, 2015, now Pat. No. 10,821,161.

(60) Provisional application No. 62/088,423, filed on Dec. 5, 2014.

(51) Int. Cl.
| | |
|---|---|
| A61K 39/00 | (2006.01) |
| C07K 14/705 | (2006.01) |
| C07K 14/35 | (2006.01) |
| A61K 35/17 | (2015.01) |
| C07K 16/28 | (2006.01) |
| C07K 14/725 | (2006.01) |
| C07K 14/71 | (2006.01) |
| C12N 5/0783 | (2010.01) |

(52) U.S. Cl.
CPC .......... *A61K 39/0011* (2013.01); *A61K 35/17* (2013.01); *C07K 14/35* (2013.01); *C07K 14/705* (2013.01); *C07K 14/7051* (2013.01); *C07K 14/70521* (2013.01); *C07K 14/71* (2013.01); *C07K 16/2803* (2013.01); *C07K 16/2896* (2013.01); *C12N 5/0636* (2013.01); *C12N 5/0637* (2013.01); *C12N 5/0638* (2013.01); *A61K 2039/5156* (2013.01); *A61K 2039/5158* (2013.01); *C07K 2317/526* (2013.01); *C07K 2317/53* (2013.01); *C07K 2317/622* (2013.01); *C07K 2319/02* (2013.01); *C07K 2319/03* (2013.01); *C07K 2319/033* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 6,136,957 A | 10/2000 | Nicola et al. | |
| 8,084,026 B2 | 12/2011 | Glaser et al. | |
| 8,551,715 B2 | 10/2013 | Gurney et al. | |
| 10,358,494 B2 * | 7/2019 | Yu | C07K 16/3061 |
| 10,821,161 B2 * | 11/2020 | Wang | C12N 5/0638 |
| 2013/0287748 A1 | 10/2013 | June et al. | |
| 2016/0075784 A1 | 3/2016 | Yu et al. | |
| 2016/0333108 A1 | 11/2016 | Forman et al. | |
| 2017/0360910 A1 | 12/2017 | Wang et al. | |
| 2020/0188432 A1 * | 6/2020 | Wang | C12N 5/0638 |

FOREIGN PATENT DOCUMENTS

| | | | |
|---|---|---|---|
| BR | 112016017806 | 10/2017 | |
| CN | 101313069 | 11/2008 | |
| RU | 2487888 | 7/2013 | |
| RU | 2515108 | 5/2014 | |
| WO | WO 2007/047829 | 4/2007 | |
| WO | WO 2007/060406 | 5/2007 | |
| WO | WO 2013/123061 | 8/2013 | |
| WO | WO 2013/142034 | 9/2013 | |
| WO | WO 2013/151762 | 10/2013 | |
| WO | WO 2014/179759 | 11/2014 | |
| WO | WO-2014179759 A1 * | 11/2014 | .......... A61K 39/395 |
| WO | WO 2015/121454 | 8/2015 | |
| WO | WO 2015/166056 | 11/2015 | |

OTHER PUBLICATIONS

Chu et al., Clinical Cancer Research 20(15): 3989-4000 (Year: 2014).*
Chu et al., Leukemia 28(4): 917-927 (Year: 2014).*
Berger et al., "Adoptive transfer of effector CD8+ T cells derived from central memory cells establishes persistent T cell memory in primates," J Clin Invest, 2008, 118(1):294-305.
Chien et al., "Significant structural and functional change of an antigen-binding site by a distant amino acid substitution: proposal of a structural mechanism," Proc Natl Acad Sci USA., Jul. 1989, 86(14):5532-5536.
Chu et al., "Genetic modification of T cells redirected toward CS1 enhances eradication of myeloma cells," Clin Cancer Res., Aug. 1, 2014, 20(15):3989-4000.
Chu et al., "CS1-specific chimeric antigen receptor (CAR)-engineered natural killer cells enhance in vitro and in vivo antitumor activity against human multiple myeloma," Leukemia, Sep. 26, 2013,28(4):917-927.
Edelman et al., "The covalent structure of an entire γG immunoglobulin molecule." Proc Natl Acad Sci USA, May 1, 1969, 63(1):78-85.
Galetto et al., "Bypassing the Constraint for Chimeric Antigen Receptor (CAR) Development in T-Cells Expressing the Targeted Antigen: Improvement of Anti-CS1 CAR Activity in Allogenic TCRa/CS1 Double Knockout T-Cells for the Treatment of Multiple Myeloma (MM)," Blood, 2015, 126(23):Abstract 116.
Galetto et al., "Abstract 2289: Allogenic TCRa/CS1 double knock-out T-cells bearing an anti-CS1 chimeric antigen receptor: An improved immunotherapy approach for the treatment of multiple myeloma," AACR 107th Annual Meeting, Apr. 16-20, 2016, Cancer Res., 76(14):5 pages.
Hsi et al., "CS1, a potential new therapeutic antibody target for the treatment of multiple myeloma." Clin Cancer Res., May 1, 2008, 14(1):2775-84.

(Continued)

*Primary Examiner* — Phuong Huynh
(74) *Attorney, Agent, or Firm* — Fish & Richardson P.C.

(57) ABSTRACT

Chimeric antigen receptors for use in treating malignant melanoma and other cancers expressing CS1 are described.

9 Claims, 16 Drawing Sheets

Specification includes a Sequence Listing.

(56) References Cited

OTHER PUBLICATIONS

Jena et al., "Chimeric antigen receptor (CAR)-specific monoclonal antibody to detect CD19-specific T cells in clinical trials," PLoS One., 2013, 8(3):e57838.

Kalos et al., "Adoptive T cell transfer for cancer immunotherapy in the era of synthetic biology," Immunity, 2013, 39(1):49-60.

International Preliminary Report on Patentability in International Application No. PCT/US2015/064303, dated Jun. 15, 2017, dated Jun. 6, 2017, 2 pages.

International Search Report and Written Opinion in International Application No. PCT/US2015/064303, dated Apr. 25, 2016, 15 pages.

Lipowska-Bhalla et al., "Targeted Immunotherapy of cancer with CAR T cells: achievements and challenges," Cancer Immunol Immunother., Jul. 2012, 61(7):953-962.

Mathur et al., "Abstract 502:Universal SLAMF7-specific CAR T-cells as treatment for multiple myeloma," Blood, 2017, 130:15 pages.

Mchayleh et al., "Chimeric Antigen Receptor T-Cells: The Future is Now," J. Clin. Med., 2019, 8:207-210.

Milone et al., "Chimeric Receptors Containing CD137 Signal Transduction Domains Mediate Enhanced Survival of T Cells and Increased Antileukemic Efficacy In Vivo," Mol Ther., Aug. 2009, 17(8):1453-1464.

Ohno et al., "Antigen-binding specificities of antibodies are primarily determined by seven residues of VH," Proc Natl Acad Sci USA., May 1985, 82(9):2945-2949.

Rudikoff et al., "Single amino acid substitution altering antigen-binding specificity," Proc Natl Acad Sci USA., Mar. 1982, 79(6):1979-1983.

Singer, "Geny and Genomy," Moscow, 1998, vol. 1, p. 63.

Tai et al., "Anti-CS1 humanized monoclonal antibody HuLuc63 inhibits myeloma cell adhesion and induces antibody-dependent cellular cytotoxicity in the bone marrow milieu," Blood, 2008, 112:1329-1337.

Till et al., "CD20-specific adoptive immunotherapy for lymphoma using a chimeric antigen receptor with both CD28 and 4-1BB domains: pilot clinical trial results," Blood, 2012, 119(17):3940-3950.

Wang et al., "Lenalidomide Enhances the Function of CS1 Chimeric Antigen Receptor-Redirected T Cells Against Multiple Myeloma," Clin. Cancer Res., Jan. 1, 2018, 24(1):106-119.

Vinay et al., "4-1BB Signaling Beyond T Cells," Cell Mol Immun., Jul. 2011, 8(4):281-284.

European Office Action in EP Application No. 15819937.2 dated Sep. 20, 2018, 6 pages.

Mathur et al., "Universal SLAMF7-Specific CAR T-Cells As Treatment for Multiple Myeloma," Blood, 2017, 130(Supplement 1):502.

\* cited by examiner

MLLLVTSLLLCELPHPAFLLIPEVQLVESGGGLVQPGGSLRLSCAASGFDFSRYWMSWVRQA

GMCSFRa signal peptide (22 aa)    CS1scFv ( aa)

PGKGLEWIGEINPDSSTINYAPSLKDKFIISRDNAKNSLYLQMNSLRAEDTAVYYCARPDGNY

WYFDVWGQGTLVTVSSGSTSGGGSGGGSGGGGSSDIQMTQSPSSLASVGDRVTITCKAS

QDVGIAVAWYQQKPGKVPKLLIYWASTRHTGVPDRFSGSGSGTDFTLTISSLQPEDVATYYC

QQYSSYPYTFGQGTKVEIKESKYGPPCPPCPGGGSSGGGSGGQPREPQVYTLPPSQEEMTK

IgG4-Hinge (12 aa)    Linker (10 aa)    IgG4-CH3

NQVSLTCLVKGFYPSDIAVEWESNGQPENNYKTTPPVLDSDGSFFLYSRLTVDKSRWQEGN

VFSCSVMHEALHNHYTQKSLSLSLGKMFWVLVVVGGVLACYSLLVTVAFIIFWVRSKRSRGG

CD28 transmembrane (28 aa)    CD28 (41 aa)

HSDYMNMTPRRPGPTRKHYQPYAPPRDFAAYRSGGGRVKFSRSADAPAYQQGQNQLYNE

Gly3    CD3 Zeta ( 112 aa)

LNLGRREEYDVLDKRRGRDPEMGGKPRRKNPQEGLYNELQKDKMAEAYSEIGMKGERRRG

KGHDGLYQGLSTATKDTYDALHMQALPPRLEGGGEGRGSLLTCGDVEENPGPRMLLLVTSL

T2A (24 aa)    EGFRt

LLCELPHPAFLLIPRKVCNGIGIGEFKDSLSINATNIKHFKNCTSISGDLHILPVAFRGDSFTHTP

PLDPQELDILKTVKEITGFLLIQAWPENRTDLHAFENLEIIRGRTKQHGQFSLAVVSLNITSLGL

RSLKEISDGDVIISGNKNLCYANTINWKKLFGTSGQKTKIISNRGENSCKATGQVCHALCSPEG

CWGPEPRDCVSCRNVSRGRECVDKCNLLEGEPREFVENSECIQCHPECLPQAMNITCTGRG

PDNCIQCAHYIDGPHCVKTCPAGVMGENNTLVWKYADAGHVCHLCHPNCTYGCTGPGLE

GCPTNGPKIPSIATGMVGALLLLLVVALGIGLFM

FIG. 2

MLLLVTSLLLCELPHPAFLLIPEVQLVESGGGLVQPGGSLRLSCAASGFDFSRYWMSWVRQA

GMCSFRa signal    CS1scFv

PGKGLEWIGEINPDSSTINYAPSLKDKFIISRDNAKNSLYLQMNSLRAEDTAVYYCARPDGNY
WYFDVWGQGTLVTVSSGSTSGGGSGGGSGGGGSSDIQMTQSPSSLSASVGDRVTITCKAS
QDVGIAVAWYQQKPGKVPKLLIYWASTRHTGVPDRFSGSGSGTDFTLTISSLQPEDVATYYC
QQYSSYPYTFGQGTKVEIKESKYGPPCPPCPGGGSSGGGSGGQPREPQVYTLPPSQEEMTK

IgG4 hinge    linker    IgG4

NQVSLTCLVKGFYPSDIAVEWESNGQPENNYKTTPPVLDSDGSFFLYSRLTVDKSRWQEGN
VFSCSVMHEALHNHYTQKSLSLSLGKMALIVLGGVAGLLLFIGLGIFFKRGRKKLLYIFKQPFM

CD4tm    4-1BB

RPVQTTQEEDGCSCRFPEEEEGGCELGGGRVKFSRSADAPAYQQGQNQLYNELNLGRREEY

Gly3    Zeta

DVLDKRRGRDPEMGGKPRRKNPQEGLYNELQKDKMAEAYSEIGMKGERRRGKGHDGLYQ
GLSTATKDTYDALHMQALPPRLEGGGEGRGSLLTCGDVEENPGPRMLLLVTSLLLCELPHPA

T2A    EGFRt

FLLIPRKVCNGIGIGEFKDSLSINATNIKHFKNCTSISGDLHILPVAFRGDSFTHTPPLDPQELDIL
KTVKEITGFLLIQAWPENRTDLHAFENLEIIRGRTKQHGQFSLAVVSLNITSLGLRSLKEISDGD
VIISGNKNLCYANTINWKKLFGTSGQKTKIISNRGENSCKATGQVCHALCSPEGCWGPEPRD
CVSCRNVSRGRECVDKCNLLEGEPREFVENSECIQCHPECLPQAMNITCTGRGPDNCIQCAH
YIDGPHCVKTCPAGVMGENNTLVWKYADAGHVCHLCHPNCTYGCTGPGLEGCPTNGPKIP
SIATGMVGALLLLLVVALGIGLFM

FIG. 6

MLLLVTSLLLCELPHPAFLLIPEVQLVESGGGLVQPGGSLRLSCAASGFDFSRYWMSWVRQA

GMSCFRa　　　　　　　CS1scFV

PGKGLEWIGEINPDSSTINYAPSLKDKFIISRDNAKNSLYLQMNSLRAEDTAVYYCARPDGNY
WYFDVWGQGTLVTVSSGSTSGGGSGGGSGGGGSSDIQMTQSPSSLSASVGDRVTITCKAS
QDVGIAVAWYQQKPGKVPKLLIYWASTRHTGVPDRFSGSGSGTDFTLTISSLQPEDVATYYC
QQYSSYPYTFGQGTKVEIKESKYGPPCPPCPAPEFEGGPSVFLFPPKPKDTLMISRTPEVTCVV

IgG4

VDVSQEDPEVQFNWYVDGVEVHNAKTKPREEQFQSTYRVVSVLTVLHQDWLNGKEYKCK
VSNKGLPSSIEKTISKAKGQPREPQVYTLPPSQEEMTKNQVSLTCLVKGFYPSDIAVEWESNG
QPENNYKTTPPVLDSDGSFFLYSRLTVDKSRWQEGNVFSCSVMHEALHNHYTQKSLSLSLGK

MALIVLGGVAGLLLFIGLGIFFKRGRKKLLYIFKQPFMRPVQTTQEEDGCSCRFPEEEEGGCEL

CD4tm　　　　　　　4-1BB

GGGRVKFSRSADAPAYQQGQNQLYNELNLGRREEYDVLDKRRGRDPEMGGKPRRKNPQE

Gly3　Zeta

GLYNELQKDKMAEAYSEIGMKGERRRGKGHDGLYQGLSTATKDTYDALHMQALPPRLEGG

T2A

GEGRGSLLTCGDVEENPGPRMLLLVTSLLLCELPHPAFLLIPRKVCNGIGIGEFKDSLSINATNI

EGFt

KHFKNCTSISGDLHILPVAFRGDSFTHTPPLDPQELDILKTVKEITGFLLIQAWPENRTDLHAFE
NLEIIRGRTKQHGQFSLAVVSLNITSLGLRSLKEISDGDVIISGNKNLCYANTINWKKLFGTSGQ
KTKIISNRGENSCKATGQVCHALCSPEGCWGPEPRDCVSCRNVSRGRECVDKCNLLEGEPRE
FVENSECIQCHPECLPQAMNITCTGRGPDNCIQCAHYIDGPHCVKTCPAGVMGENNTLVW
KYADAGHVCHLCHPNCTYGCTGPGLEGCPTNGPKIPSIATGMVGALLLLLVVALGIGLFM

FIG. 7

MLLLVTSLLLCELPHPAFLLIPEVQLVESGGGLVQPGGSLRLSCAASGFDFSRYWMSWVRQA

GMCSFRa          CS1scFv

PGKGLEWIGEINPDSSTINYAPSLKDKFIISRDNAKNSLYLQMNSLRAEDTAVYYCARPDGNY
WYFDVWGQGTLVTVSSGSTSGGGSGGGSGGGGSSDIQMTQSPSSLSASVGDRVTITCKAS
QDVGIAVAWYQQKPGKVPKLLIYWASTRHTGVPDRFSGSGSGTDFTLTISSLQPEDVATYYC
QQYSSYPYTFGQGTKVEIKESKYGPPCPPCPAPEFEGGPSVFLFPPKPKDTLMISRTPEVTCVV

IgG4

VDVSQEDPEVQFNWYVDGVEVHNAKTKPREEQFQSTYRVVSVLTVLHQDWLNGKEYKCK
VSNKGLPSSIEKTISKAKGQPREPQVYTLPPSQEEMTKNQVSLTCLVKGFYPSDIAVEWESNG
QPENNYKTTPPVLDSDGSFFLYSRLTVDKSRWQEGNVFSCSVMHEALHNHYTQKSLSLSLGK
MFWVLVVVGGVLACYSLLVTVAFIIFWVRSKRSRGGHSDYMNMTPRRPGPTRKHYQPYAP

CD28tm            CD28cyto

PRDFAAYRSGGGRVKFSRSADAPAYQQGQNQLYNELNLGRREEYDVLDKRRGRDPEMGG

Gly3  Zeta

KPRRKNPQEGLYNELQKDKMAEAYSEIGMKGERRRGKGHDGLYQGLSTATKDTYDALHM
QALPPRLEGGGEGRGSLLTCGDVEENPGPRMLLLVTSLLLCELPHPAFLLIPRKVCNGIGIGEF

T2A            EGFRt

KDSLSINATNIKHFKNCTSISGDLHILPVAFRGDSFTHTPPLDPQELDILKTVKEITGFLLIQAWP
ENRTDLHAFENLEIIRGRTKQHGQFSLAVVSLNITSLGLRSLKEISDGDVIISGNKNLCYANTIN
WKKLFGTSGQKTKIISNRGENSCKATGQVCHALCSPEGCWGPEPRDCVSCRNVSRGRECVD
KCNLLEGEPREFVENSECIQCHPECLPQAMNITCTGRGPDNCIQCAHYIDGPHCVKTCPAGV
MGENNTLVWKYADAGHVCHLCHPNCTYGCTGPGLEGCPTNGPKIPSIATGMVGALLLLLV
VALGIGLFM

FIG. 8

MLLLVTSLLLCELPHPAFLLIPEVQLVESGGGLVQPGGSLRLSCAASGFDFSRYWMSWVRQA

GMCSFa                CS1scFv

PGKGLEWIGEINPDSSTINYAPSLKDKFIISRDNAKNSLYLQMNSLRAEDTAVYYCARPDGNY
WYFDVWGQGTLVTVSSGSTSGGGSGGGSGGGGSSDIQMTQSPSSLSASVGDRVTITCKAS
QDVGIAVAWYQQKPGKVPKLLIYWASTRHTGVPDRFSGSGSGTDFTLTISSLQPEDVATYYC
QQYSSYPYTFGQGTKVEIKGGGSSGGGSGMALIVLGGVAGLLLFIGLGIFFKRGRKKLLYIFKQ linker          CD4tm                    4-1BB

PFMRPVQTTQEEDGCSCRFPEEEEGGCELGGGRVKFSRSADAPAYQQGQNQLYNELNLGR

Gly3  Zeta

REEYDVLDKRRGRDPEMGGKPRRKNPQEGLYNELQKDKMAEAYSEIGMKGERRRGKGHD
GLYQGLSTATKDTYDALHMQALPPRLEGGGEGRGSLLTCGDVEENPGPRMLLLVTSLLLCEL

T2A                    EGFRt

PHPAFLLIPRKVCNGIGIGEFKDSLSINATNIKHFKNCTSISGDLHILPVAFRGDSFTHTPPLDPQ
ELDILKTVKEITGFLLIQAWPENRTDLHAFENLEIIRGRTKQHGQFSLAVVSLNITSLGLRSLKEI
SDGDVIISGNKNLCYANTINWKKLFGTSGQKTKIISNRGENSCKATGQVCHALCSPEGCWGP
EPRDCVSCRNVSRGRECVDKCNLLEGEPREFVENSECIQCHPECLPQAMNITCTGRGPDNCI
QCAHYIDGPHCVKTCPAGVMGENNTLVWKYADAGHVCHLCHPNCTYGCTGPGLEGCPTN
GPKIPSIATGMVGALLLLLVVALGIGLFM

FIG. 9

MLLLVTSLLLCELPHPAFLLIPEVQLVESGGGLVQPGGSLRLSCAASGFDFSRYWMSWVRQA

GMCSFRa                CS1scFv

PGKGLEWIGEINPDSSTINYAPSLKDKFIISRDNAKNSLYLQMNSLRAEDTAVYYCARPDGNY
WYFDVWGQGTLVTVSSGSTSGGGSGGGSGGGGSSDIQMTQSPSSLSASVGDRVTITCKAS
QDVGIAVAWYQQKPGKVPKLLIYWASTRHTGVPDRFSGSGSGTDFTLTISSLQPEDVATYYC
QQYSSYPYTFGQGTKVEIKGGGSSGGGSGMFWVLVVVGGVLACYSLLVTVAFIIFWVRSKRS

Linker       CD28tm                              CD28cyto

RGGHSDYMNMTPRRPGPTRKHYQPYAPPRDFAAYRSGGGRVKFSRSADAPAYQQGQNQ

Gly3  Zeta

LYNELNLGRREEYDVLDKRRGRDPEMGGKPRRKNPQEGLYNELQKDKMAEAYSEIGMKGE
RRRGKGHDGLYQGLSTATKDTYDALHMQALPPRLEGGGEGRGSLLTCGDVEENPGPRMLL

T2A           EGFRt
LVTSLLLCELPHPAFLLIPRKVCNGIGIGEFKDSLSINATNIKHFKNCTSISGDLHILPVAFRGDSF
THTPPLDPQELDILKTVKEITGFLLIQAWPENRTDLHAFENLEIIRGRTKQHGQFSLAVVSLNIT
SLGLRSLKEISDGDVIISGNKNLCYANTINWKKLFGTSGQKTKIISNRGENSCKATGQVCHALC
SPEGCWGPEPRDCVSCRNVSRGRECVDKCNLLEGEPREFVENSECIQCHPECLPQAMNITC
TGRGPDNCIQCAHYIDGPHCVKTCPAGVMGENNTLVWKYADAGHVCHLCHPNCTYGCTG
PGLEGCPTNGPKIPSIATGMVGALLLLLVVALGIGLFM

FIG. 10

```
   1 GTTAGACCAG ATCTGAGCCT GGGAGCTCTC TGGCTAACTA GGGAACCCAC TGCTTAAGCC
     CAATCTGGTC TAGACTCGGA CCCTCGAGAG ACCGATTGAT CCCTTGGGTG ACGAATTCGG
  61 TCAATAAAGC TTGCCTTGAG TGCTTCAAGT AGTGTGTGCC CGTCTGTTGT GTGACTCTGG
     AGTTATTTCG AACGGAACTC ACGAAGTTCA TCACACACGG GCAGACAACA CACTGAGACC
 121 TAACTAGAGA TCCCTCAGAC CCTTTTAGTC AGTGTGGAAA ATCTCTAGCA GTGGCGCCCG
     ATTGATCTCT AGGGAGTCTG GGAAAATCAG TCACACCTTT TAGAGATCGT CACCGCGGGC
 181 AACAGGGACT TGAAAGCGAA AGGGAAACCA GAGGAGCTCT CTCGACGCAG GACTCGGCTT
     TTGTCCCTGA ACTTTCGCTT TCCCTTTGGT CTCCTCGAGA GAGCTGCGTC CTGAGCCGAA
 241 GCTGAAGCGC GCACGGCAAG AGGCGAGGGG CGGCGACTGG TGAGTACGCC AAAAATTTTG
     CGACTTCGCG CGTGCCGTTC TCCGCTCCCC GCCGCTGACC ACTCATGCGG TTTTTAAAAC
 301 ACTAGCGGAG GCTAGAAGGA GAGAGATGGG TGCGAGAGCG TCAGTATTAA GCGGGGGAGA
     TGATCGCCTC CGATCTTCCT CTCTCTACCC ACGCTCTCGC AGTCATAATT CGCCCCCTCT
 361 ATTAGATCGA TGGGAAAAAA TTCGGTTAAG GCCAGGGGGA AAGAAAAAAT ATAAATTAAA
     TAATCTAGCT ACCCTTTTTT AAGCCAATTC CGGTCCCCCT TTCTTTTTTA TATTTAATTT
 421 ACATATAGTA TGGGCAAGCA GGGAGCTAGA ACGATTCGCA GTTAATCCTG GCCTGTTAGA
     TGTATATCAT ACCCGTTCGT CCCTCGATCT TGCTAAGCGT CAATTAGGAC CGGACAATCT
 481 AACATCAGAA GGCTGTAGAC AAATACTGGG ACAGCTACAA CCATCCCTTC AGACAGGATC
     TTGTAGTCTT CCGACATCTG TTTATGACCC TGTCGATGTT GGTAGGGAAG TCTGTCCTAG
 541 AGAAGAGCTA AGATCATTAT ATAATACGAT TATTGTGTGC ATCAAAGGAT
     TCTTCTTGAA TCTAGTAATA TATTATGCTA TCGTTGGGAG ATAACACACG TAGTTTCCTA
 601 AGAGATAAAA GACACCAAGG AAGCTTTAGA CAAGATAGAG GAAGAGCAAA ACAAAAGTAA
     TCTCTATTTT CTGTGGTTCC TTCGAAATCT GTTCTATCTC CTTCTCGTTT TGTTTTCATT
 661 GAAAAAAGCA CAGCAAGCAG CAGCTGACAC AGGCACAGC AATCAGGTCA GCCAAAATTA
     CTTTTTTCGT GTCGTTCGTC GTCGACTGTG TCCTGTGTCG TTAGTCCAGT CGGTTTTAAT
 721 CCCTATAGTG CAGAACATCC AGGGGCAAAT GGTACATCAG GCCATATCAC CTAGAACTTT
     GGGATATCAC GTCTTGTAGG TCCCCGTTTA CCATGTAGTC CGGTATAGTG GATCTTGAAA
 781 AAATGCATGG GTAAAAGTAG TAGAAGAGAA GGCTTTCAGC CCAGAAGTGA TACCCATGTT
     TTTACGTACC CATTTTCATC ATCTTCTCTT CCGAAAGTCG GGTCTTCACT ATGGGTACAA
 841 TTCAGCATTA TCAGAAGGAG CCACCCCACA AGATTTAAAC ACCATGCTAA ACACAGTGGG
     AAGTCGTAAT AGTCTTCCTC GGTGGGGTGT TCTAAATTTG TGGTACGATT TGTGTCACCC
 901 GGGACATCAA GCAGCCATGC AAATGTTAAA AGAGACCATC AATGAGGAAG CTGCAGGCAA
     CCCTGTAGTT CGTCGGTACG TTTACAATTT TCTCTGGTAG TTACTCCTTC GACGTCCGTT
 961 AGAGAAGAGT GGTGCAGAGA GAAAAAGAG CAGTGGGAAT AGGAGCTTTG TTCCTTGGGT
     TCTCTTCTCA CCACGTCTCT CTTTTTTCTC GTCACCCTTA TCCTCGAAAC AAGGAACCCA
1021 TCTTGGGAGC AGCAGGAAGC ACTATGGGCG CAGCGTCAAT GACGCTGACG GTACAGGCCA
     AGAACCCTCG TCGTCCTTCG TGATACCCGC GTCGCAGTTA CTGCGACTGC CATGTCCGGT
1081 GACAATTATT GTCTGGTATA GTGCAGCAGC AGAACATATT GCTGAGGCGC ATTGAGGCGC
     CTGTTAATAA CAGACCATAT CACGTCGTCG TCTTGTTAAA CGACTCCGA TAACTCCGCG
1141 AACAGCATCT GTTGCAACTC ACAGTCTGGG GCATCAAGCA GCTCCAGGCA AGAATCCTGG
     TTGTCGTAGA CAACGTTGAG TGTCAGACCC CGTAGTTCGT CGAGGTCCGT TCTTAGGACC
1201 CTGTGGAAAG ATACCTAAAG GATCAACAGC TCCTGGGGAT TTGGGGTTGC TCTGGAAAAC
     GACACCTTTC TATGGATTTC CTAGTTGTCG AGGACCCCTA AACCCCAACG AGACCTTTTG
1261 TCATTTGCAC CACTGCTGTG CCTTGGATCT ACAAATGGCA GTATTCATCC ACAATTTTAA
     AGTAAACGTG GTGACGACAC GGAACCTAGA TGTTTACCGT CATAAGTAGG TGTTAAAATT
1321 AAGAAAAGCA GGGATTGGGG GGTACAGTGC AGGGGAAAGA ATAGTAGACA TAATAGCAAC
     TTCTTTTCCC CCCTAACCCC CCATGTCACG TCCCCCTTTCT TATCATCTGT ATTATCGTTG
1381 AGACATACAA ACTAAAGAAT TACAAAAACA AATTACAAAA ATTCAAAATT TCGGGTTTA
     TCTGTATGTT TGATTCTTA ATGTTTTGT TTAATGTTTT TAAGTTTTAA AAGCCCAAAT
1441 TTACAGGGAC AGCAGAGATC CAGTTTGGGG ATCAATTGCA TGAAGAATCT GCTTAGGGTT
     AATGTCCCTG TCGTCTCTAG GTCAAACCCC TAGTTAACGT ACTTCTTAGA CGAATCCCAA
1501 AGGCGTTTTG CGCTGCTTCG CGAGGATCTG CGATCGCTCC GGTGCCGTC AGTGGGCAGA
     TCCGCAAAAC GCGACGAAGC GCTCCTAGAC GCTAGCGAGG CCACGGGCAG TCACCCGTCT
1561 GCGCACATCG CCCACAGTCC CCGAGAAGTT GGGGGGAGGG GTCGGCAATT GAACCGGTGC
     CGCGTGTAGC GGGTGTCAGG GGCTCTTCAA CCCCCCTCCC CAGCCGTTAA CTTGGCCACG
1621 CTAGAGATAA TGGCGCGGGG TAAACTGGGA AAGTGATGTC GTGTACTGGC TCCGCCTTTT
     GATCTCTTCC ACCGCGCCCC ATTTGACCCT TTCACTACAG CACATGACCG AGGCGGAAAA
1681 TCCCGAGGGT GGGGGAGAAC CGTATATAAG TGCAGTAGTC GCCGTGAACG TTCTTTTTCG
     AGGGCTCCCA CCCCCTCTTG GCATATATTC ACGTCATCAG CGGCACTTGC AAGAAAAAGC
1741 CAACGGGTTT GCCGCCAGAA CACAGCTGAA GCTTCGAGGG GCTCGCATCT CTCCTTCACG
     GTTGCCCAAA CGGCGGTCTT GTGTCGACTT CGAAGCTCCC CGAGCGTAGA GAGGAAGTGC
1801 CGCCCGCCGC CCTACCTGAG GCCGCCATCC ACGCCGGTTG AGTCGCGTTC TGCCGCCTCC
     GCGGGCGGCG GGATGGACTC CGGCGGTAGG TGCGGCCAAC TCAGCGCAAG ACGGCGGAGG
1861 CGCCTGCTGT GCCTCGTCGA CTGCGTCCGC CGTCTAGGTA AGTTTAAAGC TCAGGTCGAG
     GCGGACACCA CGGAGCAGCT GACGCAGGCG CAGATCCAT TCAAATTTCG AGTCCAGCTC
1921 ACCGGGCCTT TGTCCGGCGC TCCCTTGGAG CCTACCTAGA CTCAGCCGGC TCTCCACGCT
     TGGCCCGGAA ACAGGCCGCG AGGGAACCTC GGATGGATCC GAGTCGGCCG AGAGGTGCGA
```

FIG. 11A

```
1981 TTGCCTGACC CTGCTTGCTC AACTCTACGT CTTTGTTTCG TTTTCTGTTC TGCGCCGTTA
     AACGGACTGG GACGAACGAG TTGAGATGCA GAAACAAAGC AAAAGACAAG ACGCGGCAAT
2041 CAGATCCAAG CTGTGACCGG CGCCTACGGC TAGCGCCGCC ACCATGCTGC TGCTCGTGAC
     GTCTAGGTTC GACACTGGCC GCGGATGCCG ATCGCGGCGG TGGTACGACG ACGAGCACTG
2101 ATCTCTGCTC CTGTGCGAGC TGCCCCACCC CGCCTTTCTG CTGATTCCTG AGGTGCAGCT
     TAGAGACGAC GACACGCTCG ACGGGGTGGG GCGGAAAGAC GACTAAGGAC TCCACGTCGA
2161 GGTGGAAAGC GGCGGAGGAC TGGTGCAGCC TGGCGGATCT CTGAGACTGA GCTGTGCCGC
     CCACCTTTCG CCGCCTCCTG ACCACGTCGG ACCGCCTAGA GACTCTGACT CGACACGGCG
2221 CAGCGGCTTC GACTTCAGCC GGTACTGGAT GAGCTGGGTG CGCCAGGCCC CTGGCAAAGG
     GTCGCCGAAG CTGAAGTCGG CCATGACCTA CTCGACCCAC GCGGTCCGGG GACCGTTTCC
2281 CCTGGAATGG ATCGGCGAGA TCAACCCCGA CAGCAGCACC ATCAACTACG CCCCCAGCCT
     GGACCTTACC TAGCCGCTCT AGTTGGGGCT GTCGTCGTGG TAGTTGATGC GGGGGTCGGA
2341 GAAGGACAAG TTCATCATCA GCCGGGACAA CGCCAAGAAC AGCCTGTACC TGCAGATGAA
     CTTCCTGTTC AAGTAGTAGT CGGCCCTGTT GCGGTTCTTG TCGGACATGG ACGTCTACTT
2401 CTCCCTGCGG GCCGAGGACA CCGCCGTGTA CTATTGCGCC AGACCCGACG GCAACTACTG
     GAGGGACGCC CGGCTCCTGT GGCGGCACAT GATAACGCGG TCTGGGCTGC CGTTGATGAC
2461 GTACTTCGAT GTGTGGGGCC AGGGCACCCT CGTGACAGTG TCTAGCGGCA GCACAAGCGG
     CATGAAGCTA CACACCCCGG TCCCGTGGGA GCACTGTCAC AGATCGCCGT CGTGTTCGCC
2521 AGGCGGATCT GGCGGAGGAT CAGGCGGGGG AGGATCCAGC GATATCCAGA TGACCCAGAG
     TCCGCCTAGA CCGCCTCCTA GTCCGCCCCC TCCTAGGTCG CTATAGGTCT ACTGGGTCTC
2581 CCCCAGCAGC CTGTCTGCCA GCGTGGGCGA CAGAGTGACC ATCACATGCA AGGCCAGCCA
     GGGGTCGTCG GACAGACGGT CGCACCCGCT GTCTCACTGG TAGTGTACGT TCCGGTCGGT
2641 GGACGTGGGA ATCGCCGTGG CCTGGTATCA GCAGAAACCC GGCAAGGTGC CCAAGCTGCT
     CCTGCACCCT TAGCGGCACC GGACCATAGT CGTCTTTGGG CCGTTCCACG GGTTCGACGA
2701 GATCTACTGG GCCAGCACCA GACACACCGG CGTGCCCGAT AGATTTTCCG GCAGCGGCTC
     CTAGATGACC CGGTCGTGGT GTGTGGCC GCACGGGCTA TCTAAAAGGC CGTCGCCGAG
2761 CGGCACCGAC TTCACCCTGA CAATCAGCTC CCTGCAGCCT GAGGACGTGG CCACCTACTA
     GCCGTGGCTG AAGTGGGACT GTTAGTCGAG GGACGTCGGA CTCCTGCACC GGTGGATGAT
2821 CTGCCAGCAG TACAGCAGCT ACCCCTACAC CTTCGGACAG GGCACCAAGG TGGAAATCAA
     GACGGTCGTC ATGTCGTCGA TGGGGATGTG GAAGCCTGTC CCGTGGTTCC ACCTTTAGTT
2881 AGAGTCTAAG TACGGCCCTC CCTGCCCCCC TTGTCCAGGC GGCGGATCTT CCGGAGGAGG
     TCTCAGATTC ATGCCGGGAG GGACGGGGGG AACAGGTCCG CCGCCTAGAA GGCCTCCTCC
2941 AAGCGGAGCC CAGCCCAGAG AACCTCAGGT GTACACACTG CCCCCTAGCC AGGAAGAGAT
     TTCGCCTCCG GTCGGGTCTC TTGGAGTCCA CATGTGTGAC GGGGGATCGG TCCTTCTCTA
3001 GACCAAGAAT CAGGTGTCCC TGACATGCCT TTCTACCCTG CCGATATCGC
     CTGGTCTTA GTCCACAGGG ACTGTACGGA GCACTTCCCG AAGATGGGGA GGCTATAGCG
3061 CGTGGAATGG GAGAGCAACG GCCAGCCTGA GAACAACTAC AAGACCACCC CCCCTGTGCT
     GCACCTTACC CTCTCGTTGC CGGTCGGACT CTTGTTGATG TTCTGGTGGG GGGGACACGA
3121 GGACAGCGAC GGCTCATTCT TCCTGTACAG CAGGCTGACC GTGGACAAGA GCCGGTGGCA
     CCTGTCGCTG CCGAGTAAGA AGGACATGTC GTCCGACTGG CACCTGTTCT CGGCCACCGT
3181 GGAAGGCAAC GTGTTCAGCT GCTCCGTGAT GCACGAGGCC CTGCACAACC ACTACACCCA
     CCTTCCGTTG CACAAGTCGA CGAGGCACTA CGTGCTCCGG GACGTGTTGG TGATGTGGGT
3241 GAAGTCCCTG AGCCTGTCCC TGGGCAAGAT GTTCTGGGTG CTGGTGGTCG TGGGCGGCGT
     CTTCAGGGAC TCGGACAGGG ACCCGTTCTA CAAGACCCAC GACCACCAGC ACCGGCCGCA
3301 GCTGGCCTGT TATAGCCTGC TCGTGACCGT GGCCTTCATC ATCTTTTGGG TGCGCAGCAA
     CGACCGGACA ATATCGGACG AGCACTGGCA CCGGAAGTAG TAGAAAACCC ACGCGTCGTT
3361 GCGGAGCAGA GGCGGCCACA GCGACTACAT GAACATGACC CCCAGACGGC CAGGCCCCAC
     CGCCTCGTCT CCGCCGGTGT CGCTGATGTA CTTGTACTGG GGTCTGCCG GTCCGGGGTG
3421 CCGGAAACAC TATCAGCCTT ACGCCCCTCC CAGAGACTTC GCCGCTTATC GGTCCGGCGG
     GGCCTTTGTG ATAGTCGGAA TGCGGGGAGG GTCTCTGAAG CGGCGAATAG CCAGGCCGCC
3481 AGGGCGGGTG AAGTTCAGCA GAAGCGCCGA CGCCCCTGCC TACCAGCAGG GCCAGAATCA
     TCCCGCCCAC TTCAAGTCGT CTTCGCGGCT GCGGGACACG ATGGTCGTCC CGGTCTTAGT
3541 GCTGTACAAC GAGCTGAACC TGGGCAGAAG GGAAGAGTAC GACGTCCTGA ATAAGCGGAG
     CGACATGTTG CTCGACTTGG ACCCGTCTTC CCTTCTCATG CTGCAGGACT TATTCGCCTC
3601 AGGCCGGGAC CCTGAGATGG GCGGCAAGCC TCGGCGGAAG AACCCCCAGG AAGGCCTGTA
     TCCGGCCCTG GGACTCTACC CGCCGTTCGG AGCCGCCTTC TTGGGGGTCC TTCCGGACAT
3661 TAACGAACTG CAGAAAGACA AGATGGCCGA GGCCTACAGC GAGATCGGCA TGAAGGGCGA
     ATTGCTTGAC GTCTTTCTGT TCTACCGGCT CCGGATGTCG CTCTAGCCGT ACTTCCCGCT
3721 GCGGAGGCGG GGCAAGGGCC ACGACGGCCT GTATCAGGGC CTGTCCACCG CCACCAAGGA
     CGCCTCCGCC CCGTTCCGG TGCTGCCGGA CATAGTCCCG GACAGGTGGC GGTGGTTCCT
3781 TACCTACGAC GCCCTGCACA TGCAGGCCCT GCCCCCAAGG CTCGAGGGCG GCGGAGAGGG
     ATGGATGCTG CGGGACGTGT ACGTCCGGGA CGGGGGTTCC GAGCTCCCGC CGCCTCTCCC
3841 CAGAGGAAGT CTTCTAACAT GCGGTGACGT GGAGGAGAAT CCCGGCCCTA GGATGCTTCT
     GTCTCCTTCA GAAGATTGTA CGCCACTGCA CCTCCTCTTA GGGCCGGGAT CCTACGAAGA
```

FIG. 11B

```
3901 CCTGGTGACA AGCCTTCTGC TCTGTGAGTT ACCACACCCA GCATTCCTCC TGATCCCACG
     GGACCACTGT TCGGAAGACG AGACACTCAA TGGTGTGGGT CGTAAGGAGG ACTAGGGTGC
3961 CAAAGTGTGT AACGGAATAG GTATTGGTGA ATTTAAAGAC TCACTCTCCA TAAATGCTAC
     GTTTCACACA TTGCCTTATC CATAACCACT TAAATTCTG AGTGAGAGGT ATTTACGATG
4021 GAATATTAAA CACTTCAAAA ACTGCACCTC CATCGGTGGC GATCTCCACA TCCTGCCGGT
     CTTATAATTT GTGAAGTTTT TGACGTGGAG GTAGTCACCG CTAGAGGTGT AGGACGGCCA
4081 GGCATTTAGG GGTGACTCCT TCACACATAC TCCTCCTCTG GATCCACAGG AACTGGATAT
     CCGTAAATCC CCACTGAGGA AGTGTGTATG AGGAGGAGAC CTAGGTGTCC TTGACCTATA
4141 TCTGAAAACC GTAAAGGAAA TCACAGGGTT TTTGCTGATT CAGGCTTGGC CTGAAAACAG
     AGACTTTTGG CATTTCCTTT AGTGTCCCAA AAACGACTAA GTCCGAACCG GACTTTTGTC
4201 GACGGACCTC CATGCCTTTG AGAACCTAGA AATCATACGC GGCAGGACCA AGCAACATGG
     CTGCCTGGAG GTACGGAAAC TCTTGGATCT TTAGTATGCG CCGTCCTGGT TCGTTGTACC
4261 TCAGTTTTCT CTTGCAGTCG TCAGCCTGAA CATAACATCC TTGGGATTAC GCTCCCTCAA
     AGTCAAAAGA GAACGTCAGC AGTCGGACTT GTATTGTAGA AACCCTAATG CGAGGGAGTT
4321 GGAGATAAGT GATGGAGATG TGATAATTTC AGGAAACAAA AATTTGTGCT ATGCAAATAC
     CCTCTATTCA CTACCTCTAC ACTATTAAAG TCCTTTGTTT TTAAACACGA TACGTTTATG
4381 AATAAACTGG AAAAAACTGT TTGGGACCTC CGGTCAGAAA ACCAAAATTA TAAGCAACAG
     TTATTTGACC TTTTTTGACA AACCCTGGAG GCCAGTCTTT TGGTTTTAAT ATTCGTTGTC
4441 AGGTGAAAAC AGCTGCAAGG CCACAGGCCA GGTCTGCCAT GCCTTGTGCT CCCCCGAGGG
     TCCACTTTTG TCGACGTTCC GGTGTCCGGT CCAGACGGTA CGGAACACGA GGGGGCTCCC
4501 CTGCTGGGGC CCGGAGCCCA GGGACTGCGT CTCTTGCCGG AATGTCAGCC GAGGCAGGGA
     GACGACCCCG GGCCTCGGGT CCCTGACGCA GAGAACGGCC TTACAGTCGG CTCCGTCCCT
4561 ATGCGTGGAC AAGTGCAACC TTCTGGAGGG TGAGCCAAGG GAGTTTGTGG AGAACTCTGA
     TACGCACCTG TTCACGTTGG AAGACCTCCC ACTCGGTTCC CTCAAACACC TCTTGAGACT
4621 GTGCATACAG TGCCACCCAG AGTGCCTGCC TCAGGCCATG AACATCACCT GCACAGGACG
     CACGTATGTC ACGGTGGGTC TCACGGACGG AGTCCGGTAC TTGTAGTGGA CGTGTCCTGC
4681 GGGACCAGAC AACTGTATCC AGTGTGCCCA CTACATTGAC GGCCCCCACT GCGTCAAGAC
     CCCTGGTCTG TTGACATAGG TCACACGGGT GATGTAACTG CCGGGGGTGA CGCAGTTCTG
4741 CTGCCCGGCA GGAGTCATGG GAGAAAACAA CACCCTGGTC TGGAAGTACG CAGACGCCGG
     GACGGGCCGT CCTCAGTACC CTCTTTTGTT GTGGGACCAG ACCTTCATGC GTCTGCGGCC
4801 CCATGTGTGC CACCTGTGCC ATCCAAACTG CACCTACGGA TGCACTGGGC CAGGTCTTGA
     GGTACACACG GTGGACACGG TAGGTTTGAC GTGGATGCCT ACGTGACCCG GTCCAGAACT
4861 AGGCTGTCCA ACGAATGGGC CTAAGATCCC GTCCATCGCC ACTGGGATGG TGGGGCCCT
     TCCGACAGGT TGCTTACCCG GATTCTAGGG CAGGTAGCGG TGACCCTACC ACCCCCGGGA
4921 CCTCTTGCTG CTGGTGGTGG CCCTGGGGAT CGGCCTCTTC ATGTGAGCGG CCGCTCTAGA
     GGAGAACGAC GACCACCACC GGGACCCCTA GCCGGAGAAG TACACTCGCC GGCGAGATCT
4981 CCCGGGCTGC AGGAATTCGA TATCAAGCTT ATCGATAATC AACCTCTGGA TTACAAAATT
     GGGCCCGACG TCCTTAAGCT ATAGTTCGAA TAGCTATTAG TTGGAGACCT AATGTTTTAA
5041 TGTGAAAGAT TGACTGGTAT TCTTAACTAT GTTGCTCCTT TTACGCTATG TGGATACGCT
     ACACTTTCTA ACTGACCATA AGAATTGATA CAACGAGGAA AATGCGATAC ACCTATGCGA
5101 GCTTTAATGC CTTTGTATCA TGCTATTGCT TCCCGTATGG CTTTCATTTT CTCCTCCTTG
     CGAAATTACG GAAACATAGT ACGATAACGA AGGGCATACC GAAAGTAAAA GAGGAGGAAC
5161 TATAAATCCT GGTTGCTGTC TCTTTATGAG GAGTTGTGGC CCGTTGTCAG GCAACGTGGC
     ATATTTAGGA CCAACGACAG AGAAATACTC CTCAACACCG GGCAACAGTC CGTTGCACCG
5221 GTGGTGTGCA CTGTGTTTGC TGACGCAACC CCCACTGGTT GGGGCATTGC CACCACCTGT
     CACCACACGT GACACAAACG ACTGCGTTGG GGGTGACCAA CCCCGTAACG GTGGTGGACA
5281 CAGCTCCTTT CCGGGACTTT CGCTTTCCCC CTCCCTATTG CCACGGCGGA ACTCATCGCC
     GTCGAGGAAA GGCCCTGAAA GCGAAAGGGG GAGGGATAAC GGTGCCGCCT TGAGTAGCGG
5341 GCCTGCCTTG CCCGCTGCTG GACAGGGGCT CGGCTGTTGG GCACTGACAA TTCCGTGGTG
     CGGACGGAAC GGGCGACGAC CTGTCCCCGA GCCGACAACC CGTGACTGTT AAGGCACCAC
5401 TTGTCGGGGA AATCATCGTC CTTTCCTTGG CTGCTCGCCT GTGTTGCCAC CTGGATTCTG
     AACAGCCCCT TTAGTAGCAG GAAAGGAACC GACGAGCGGA CACAACGGTG GACCTAAGAC
5461 CGCGGGACGT CCTTCTGCTA CGTCCCTTCG CCCTCAATC CAGCGGACCT TCCTTCCCGC
     GCGCCCTGCA GGAAGACGAT GCAGGGAAGC GGGAGTTAG GTCGCCTGGA AGGAAGGGCG
5521 GGCCTGCTGC CGGCTCTGCG GCCTCTTCCG CGTCTTCGCC TTCGCCCTCA GACGAGTCGG
     CCGGACGACG GCCGAGACGC CGGAGAAGGC GCAGAAGCGG AAGCGGGAGT CTGCTCAGCC
5581 ATCTCCCTTT GGGCCGCCTC CCCGCATCGA TACCGTCGAC TAGCCGTACC TTTAAGACCA
     TAGAGGGAAA CCCGGCGGAG GGGCGTAGCT ATGCAGCTG ATCGGCATGG AAATTCTGGT
5641 ATGACTTACA AGGCAGCTGT AGATCTTAGC CACTTTTTAA AGAAAAGGG GGGACTGGAA
     TACTGAATGT TCCGTCGACA TCTAGAATCG GTGAAAAATT TCTTTTCCC CCCTGACCTT
5701 GGGCTAATTC ACTCCCAAAG AAGACAAGAT CTGCTTTTTG CCTGTACTGG GTCTCTCTGG
     CCCGATTAAG TGAGGGTTTC TTCTGTTCTA GACGAAAAAC GGACATGACC CAGAGAGACC
5761 TTAGACCAGA TCTGAGCCTG GGAGCTCTCT GGCTAACTAG GAACCCACT GCTTAAGCCT
     AATCTGGTCT AGACTCGGAC CCTCGAGAGA CCGATTGATC CCTTGGGTGA CGAATTCGGA
5821 CAATAAAGCT TGCCTTGAGT GCTTCAAGTA GTGTGTGCCC GTCTGTTGTG TGACTCTGGT
```

FIG. 11C

```
            GTTATTTCGA ACGGAACTCA CGAAGTTCAT CACACACGGG CAGACAACAC ACTGAGACCA
      5881  AACTAGAGAT CCCTCAGACC CTTTTAGTCA GTGTGGAAAA TCTCTAGCAG AATTCGATAT
            TTGATCTCTA GGGAGTCTGG GAAAATCAGT CACACCTTTT AGAGATCGTC TTAAGCTATA
      5941  CAAGCTTATC GATACCGTCG ACCTCGAGGG GGGGCCCGGT ACCCAATTCG CCCTATAGTG
            GTTCGAATAG CTATGGCAGC TGGAGCTCCC CCCCGGGCCA TGGGTTAAGC GGGATATCAC
      6001  AGTCGTATTA CAATTCACTG GCCGTCGTTT TACAACGTCG TGACTGGGAA AACCCTGGCG
            TCAGCATAAT GTTAAGTGAC CGGCAGCAAA ATGTTGCAGC ACTGACCCTT TTGGGACCGC
      6061  TTACCCAACT TAATCGCCTT GCAGCACATC CCCCTTTCGC CAGCTGGCGT AATAGCGAAG
            AATGGGTTGA ATTAGCGGAA CGTCGTGTAG GGGGAAAGCG GTCGACCGCA TTATCGCTTC
      6121  AGGCCCGCAC CGATCGCCCT TCCCAACAGT TGCGCAGCCT GAATGGCGAA TGGAAATTGT
            TCCGGGCGTG GCTAGCGGGA AGGGTTGTCA ACGCGTCGGA CTTACCGCTT ACCTTTAACA
      6181  AAGCGTTAAT ATTTTGTTAA AATTCGCGTT AAATTTTTGT TAAATCAGCT CATTTTTTAA
            TTCGCAATTA TAAAACAATT TTAAGCGCAA TTTAAAAACA ATTTAGTCGA GTAAAAAATT
      6241  CCAATAGGCC GAAATCGGCA AAATCCCTTA TAAATCAAAA GAATAGACCG AGATAGGGTT
            GGTTATCCGG CTTTAGCCGT TTTAGGGAAT ATTTAGTTTT CTTATCTGGC TCTATCCCAA
      6301  GAGTGTTGTT CCAGTTTGGA ACAAGAGTCC ACTATTAAAG AACGTGGACT CCAACGTCAA
            CTCACAACAA GGTCAAACCT TGTTCTCAGG TGATAATTTC TTGCACCTGA GGTTGCAGTT
      6361  AGGGCGAAAA ACCGTCTATC AGGGCGATGG CCCACTACGT GAACCATCAC CCTAATCAAG
            TCCCGCTTTT TGGCAGATAG TCCCGCTACC GGGTGATGCA CTTGGTAGTG GGATTAGTTC
      6421  TTTTTTGGGG TCGAGGTGCC GTAAAGCACT AAATCGGAAC CCTAAAGGGA GCCCCCGATT
            AAAAAACCCC AGCTCCACGG CATTTCGTGA TTTAGCCTTG GGATTTCCCT CGGGGGCTAA
      6481  TAGAGCTTGA CGGGGAAAGC CGGCGAACGT GGCGAGAAAG GAAGGGAAGA AAGCGAAAGG
            ATCTCGAACT GCCCCTTTCG GCCGCTTGCA CCGCTCTTTC CTTCCCTTCT TTCGCTTTCC
      6541  AGCGGGCGCT AGGGCGCTGG CAAGTGTAGC GGTCACGCTG CGCGTAACCA CCACACCCGC
            TCGCCCGCGA TCCCGCGACC GTTCACATCG CCAGTGCGAC GCGCATTGGT GGTGTGGGCG
      6601  CGCGCTTAAT GCGCCGCTAC AGGGCGCGTC AGGTGGCACT TTTCGGGGAA ATGTGCGCGG
            GCGCGAATTA CGCGGCGATG TCCCGCGCAG TCCACCGTGA AAAGCCCCTT TACACGCGCC
      6661  AACCCCTATT TGTTTATTTT TCTAAATACA TTCAAATATG TATCCGCTCA TGAGACAATA
            TTGGGGATAA ACAAATAAAA AGATTTATGT AAGTTTATAC ATAGGCGAGT ACTCTGTTAT
      6721  ACCCTGATAA ATGCTTCAAT AATATTGAAA AAGGAAGAGT ATGAGTATTC AACATTTCCG
            TGGGACTATT TACGAAGTTA TTATAACTTT TTCCTTCTCA TACTCATAAG TTGTAAAGGC
      6781  TGTCGCCCTT ATTCCCTTTT TTGCGGCATT TTGCCTTCCT GTTTTTGCTC ACCCAGAAAC
            ACAGCGGGAA TAAGGGAAAA AACGCCGTAA AACGGAAGGA CAAAAACGAG TGGGTCTTTG
      6841  GCTGGTGAAA GTAAAAGATG CTGAAGATCA GTTGGGTGCA CGAGTGGGTT ACATCGAACT
            CGACCACTTT CATTTTCTAC GACTTCTAGT CAACCCACGT GCTCACCCAA TGTAGCTTGA
      6901  GGATCTCAAC AGCGGTAAGA TCCTTGAGAG TTTTCGCCCC GAAGAACGTT TTCCAATGAT
            CCTAGAGTTG TCGCCATTCT AGGAACTCTC AAAAGCGGGG CTTCTTGCAA AAGGTTACTA
      6961  GAGCACTTTT AAAGTTCTGC TATGTGGCGC GGTATTATCC CGTATTGACG CCGGGCAAGA
            CTCGTGAAAA TTTCAAGACG ATACACCGCG CCATAATAGG GCATAACTGC GGCCCGTTCT
      7021  GCAACTCGGT CGCCGCATAC ACTATTCTCA GAATGACTTG GTTGAGTACT CACCAGTCAC
            CGTTGAGCCA GCGGCGTATG TGATAAGAGT CTTACTGAAC CAACTCATGA GTGGTCAGTG
      7081  AGAAAAGCAT CTTACGGATG GCATGACAGT AAGAGAATTA TGCAGTGCTG CCATAACCAT
            TCTTTTCGTA GAATGCCTAC CGTACTGTCA TTCTCTTAAT ACGTCACGAC GGTATTGGTA
      7141  GAGTGATAAC ACTGCGGCCA ACTTACTTCT GACAACGATC GGAGGACCGA AGGAGCTAAC
            CTCACTATTG TGACGCCGGT TGAATGAAGA CTGTTGCTAG CCTCCTGGCT TCCTCGATTG
      7201  CGCTTTTTTG CACAACATGG GGGATCATGT AACTCGCCTT GATCGTTGGG AACCGGAGCT
            GCGAAAAAAC GTGTTGTACC CCCTAGTACA TTGAGCGGAA CTAGCAACCC TTGGCCTCGA
      7261  GAATGAAGCC ATACCAAACG ACGAGCGTGA CACCACGATG CCTGTAGCAA TGGCAACAAC
            CTTACTTCGG TATGGTTTGC TGCTCGCACT GTGGTGCTAC GGACATGCGTT ACCGTTGTTG
      7321  GTTGCGCAAA CTATTAACTG GCGAACTACT TACTCTAGCT TCCCGGCAAC AATTAATAGA
            CAACGCGTTT GATAATTGAC CGCTTGATGA ATGAGATCGA AGGGCCGTTG TTAATTATCT
      7381  CTGGATGGAG GCGGATAAAG TTGCAGGACC ACTTCTGCGC TCGGCCCTTC CGGCTGGCTG
            GACCTACCTC CGCCTATTTC AACGTCCTGG TGAAGACGCG AGCCGGGAAG GCCGACCGAC
      7441  GTTTATTGCT GATAAATCTG GAGCCGGTGA GCGTGGGTCT CGCGGTATCA TTGCAGCACT
            CAAATAACGA CTATTTAGAC CTCGGCCACT CGCACCCAGA GCGCCATAGT AACGTCGTGA
      7501  GGGGCCAGAT GGTAAGCCCT CCCGTATCGT AGTTATCTAC ACGACGGGGA GTCAGGCAAC
            CCCCGGTCTA CCATTCGGGA GGGCATAGCA TCAATAGATG TGCTGCCCCT CAGTCCGTTG
      7561  TATGGATGAA CGAAATAGAC AGATCGCTGA GATAGGTGCC TCACTGATTA AGCATTGGTA
            ATACCTACTT GCTTTATCTG TCTAGCGACT CTATCCACGG AGTGACTAAT TCGTAACCAT
      7621  ACTGTCAGAC CAAGTTTACT CATATATACT TTAGATTGAT TTAAAACTTC ATTTTTAATT
            TGACAGTCTG GTTCAAATGA GTATATATGA AATCTAACTA AATTTTGAAG TAAAAATTAA
      7681  TAAAGGATC TAGGTGAAGA TCCTTTTTGA TAATCTCATG ACCAAAATCC CTTAACGTGA
            ATTTTCCTAG ATCCACTTCT AGGAAAAACT ATTAGAGTAC TGGTTTTAGG GAATTGCACT
      7741  GTTTTCGTTC CACTGAGCGT CAGACCCCGT AGAAAAGATC AAAGGATCTT CTTGAGATCC
            CAAAAGCAAG GTGACTCGCA GTCTGGGGCA TCTTTTCTAG TTTCCTAGAA GAACTCTAGG
```

FIG. 11D

```
7801 TTTTTTTCTG CGCGTAATCT GCTGCTTGCA AACAAAAAAA CCACCGCTAC CAGCGGTGGT
     AAAAAAAGAC GCGCATTAGA CGACGAACGT TTGTTTTTTT GGTGGCGATG GTCGCCACCA
7861 TTGTTTGCCG GATCAAGAGC TACCAACTCT TTTTCCGAAG GTAACTGGCT TCAGCAGAGC
     AACAAACGGC CTAGTTCTCG ATGGTTGAGA AAAAGGCTTC CATTGACCGA AGTCGTCTCG
7921 GCAGATACCA AATACTGTTC TTCTAGTGTA GCCGTAGTTA GGCCACCACT TCAAGAACTC
     CGTCTATGGT TTATGACAAG AAGATCACAT CGGCATCAAT CCGGTGGTGA AGTTCTTGAG
7981 TGTAGCACCG CCTACATACC TCGCTCTGCT AATCCTGTTA CCAGTGGCTG CTGCCAGTGG
     ACATCGTGGC GGATGTATGG AGCGAGACGA TTAGGACAAT GGTCACCGAC GACGGTCACC
8041 CGATAAGTCG TGTCTTACCG GGTTGGACTC AAGACGATAG TTACCGGATA AGGCGCAGCG
     GCTATTCAGC ACAGAATGGC CCAACCTGAG TTCTGCTATC AATGGCCTAT TCCGCGTCGC
8101 GTCGGGCTGA ACGGGGGGTT CGTGCACACA GCCCAGCTTG GAGCGAACGA CCTACACCGA
     CAGCCCGACT TGCCCCCCAA GCACGTGTGT CGGGTCGAAC CTCGCTTGCT GGATGTGGCT
8161 ACTGAGATAC CTACAGCGTG AGCTATGAGA AAGCGCCACG CTTCCCGAAG GGAGAAAGGC
     TGACTCTATG GATGTCGCAC TCGATACTCT TTCGCGGTGC GAAGGGCTTC CCTCTTTCCG
8221 GGACAGGTAT CCGGTAAGCG GCAGGGTCGG AACAGGAGAG CGCACGAGGG AGCTTCCAGG
     CCTGTCCATA GGCCATTCGC CGTCCCAGCC TTGTCCTCTC GCGTGCTCCC TCGAAGGTCC
8281 GGGAAACGCC TGGTATCTTT ATAGTCCTGT CGGGTTTCGC CACCTCTGAC TTGAGCGTCG
     CCCTTTGCGG ACCATAGAAA TATCAGGACA GCCCAAAGCG GTGGAGACTG AACTCGCAGC
8341 ATTTTTGTGA TGCTCGTCAG GGGGGCGGAG CCTATGGAAA AACGCCAGCA ACGCGGCCTT
     TAAAAACACT ACGAGCAGTC CCCCCGCCTC GGATACCTTT TTGCGGTCGT TGCGCCGGAA
8401 TTTACGGTTC CTGGCCTTTT GCTGGCCTTT TGCTCACATG TTCTTTCCTG CGTTATCCCC
     AAATGCCAAG GACCGGAAAA CGACCGGAAA ACGAGTGTAC AAGAAAGGAC GCAATAGGGG
8461 TGATTCTGTG GATAACCGTA TTACCGCCTT TGAGTGAGCT GATACCGCTC GCCGCAGCCG
     ACTAAGACAC CTATTGGCAT AATGGCGGAA ACTCACTCGA CTATGGCGAG CGGCGTCGGC
8521 AACGACCGAG CGCAGCGAGT CAGTGAGCGA GGAAGCGGAA GAGCGCCCAA TACGCAAACC
     TTGCTGGCTC GCGTCGCTCA GTCACTCGCT CCTTCGCCTT CTCGCGGGTT ATGCGTTTGG
8581 GCCTCTCCCC GCGCGTTGGC CGATTCATTA ATGCAGCTGG CACGACAGGT TTCCCGACTG
     CGGAGAGGGG CGCGCAACCG GCTAAGTAAT TACGTCGACC GTGCTGTCCA AAGGGCTGAC
8641 GAAAGCGGGC AGTGAGCGCA ACGCAATTAA TGTGAGTTAG CTCACTCATT AGGCACCCCA
     CTTTCGCCCG TCACTCGCGT TGCGTTAATT ACACTCAATC GAGTGAGTAA TCCGTGGGGT
8701 GGCTTTACAC TTTATGCTTC CGGCTCGTAT GTTGTGTGGA ATTGTGAGCG GATAACAATT
     CCGAAATGTG AAATACGAAG GCCGAGCATA CAACACACCT TAACACTCGC CTATTGTTAA
8761 TCACACAGGA AACAGCTATG ACCATGATTA CGCCAAGCTC GAAATTAACC CTCACTAAAG
     AGTGTGTCCT TTGTCGATAC TGGTACTAAT GCGGTTCGAG CTTTAATTGG GAGTGATTTC
8821 GGAACAAAAG CTGGAGCTCC ACCGCGGTGG CGGCCTCGAG GTCGAGATCC GGTCGACCAG
     CCTTGTTTTC GACCTCGAGG TGGCGCCACC GCCGGAGCTC CAGCTCTAGG CCAGCTGGTC
8881 CAACCATAGT CCCGCCCCTA ACTCCGCCCA TCCCGCCCCT AACTCCGCCC AGTTCCGCCC
     GTTGGTATCA GGGCGGGGAT TGAGGCGGGT AGGGCGGGGA TTGAGGCGGG TCAAGGCGGG
8941 ATTCTCCGCC CCATGGCTGA CTAATTTTTT TTATTTATGC AGAGGCCGAG GCCGCCTCGG
     TAAGAGGCGG GGTACCGACT GATTAAAAAA AATAAATACG TCTCCGGCTC CGGCGGAGCC
9001 CCTCTGAGCT ATTCCAGAAG TAGTGAGGAG GCTTTTTTGG AGGCCTAGGC TTTTGCAAAA
     GGAGACTCGA TAAGGTCTTC ATCACTCCTC CGAAAAAACC TCCGGATCCG AAAACGTTTT
9061 AGCTTCGACG GTATCGATTG GCTCATGTCC AACATTACCG CCATGTTGAC ATTGATTATT
     TCGAAGCTGC CATAGCTAAC CGAGTACAGG TTGTAATGGC GGTACAACTG TAACTAATAA
9121 GACTAGTTAT TAATAGTAAT CAATTACGGG GTCATTAGTT CATAGCCCAT ATATGGAGTT
     CTGATCAATA ATTATCATTA GTTAATGCCC CAGTAATCAA GTATCGGGTA TATACCTCAA
9181 CCGCGTTACA TAACTTACGG TAAATGGCCC GCCTGGCTGA CCGCCCAACG ACCCCCGCCC
     GGCGCAATGT ATTGAATGCC ATTTACCGGG CGGACCGACT GGCGGGTTGC TGGGGGCGGG
9241 ATTGACGTCA ATAATGACGT ATGTTCCCAT ATAGGGCATT TCCATTGACG
     TAACTGCAGT TATTACTGCA TACAAGGGTA TCATTGCGGT TATCCCTGAA AGGTAACTGC
9301 TCAATGGGTG GAGTATTTAC GGTAAACTGC CCACTTGGCA GTACATCAAG TGTATCATAT
     AGTTACCCAC CTCATAAATG CCATTTGACG GGTGAACCGT CATGTAGTTC ACATAGTATA
9361 GCCAAGTACG CCCCCTATTG ACGTCAATGA CGGTAAATGG CCCGCCTGGC ATTATGCCCA
     CGGTTCATGC GGGGGATAAC TGCAGTTACT GCCATTTACC GGGCGGACCG TAATACGGGT
9421 GTACATGACC TTATGGGACT TTCCTACTTG GCAGTACATC TACGTATTAG TCATCGCTAT
     CATGTACTGG AATACCCTGA AAGGATGAAC CGTCATGTAG ATGCATAATC AGTAGCGATA
9481 TACCATGTG ATGCGGTTTT GGCAGTACAT CAATGGGCGT GGATAGCGGT TTGACTCACG
     ATGGTACCAC TACGCCAAAA CCGTCATGTA GTTACCCGCA CCTATCGCCA AACTGAGTGC
9541 GGGATTTCCA AGTCTCCACC CCATTGACGT CAATGGGAGT TTGTTTTGGC ACCAAAATCA
     CCCTAAAGGT TCAGAGGTGG GGTAACTGCA GTTACCCTCA AACAAAACCG TGGTTTTAGT
9601 ACGGGACTTT CCAAAATGTC GTAACAACTC CGCCCCATTG ACGCAAATGG GCGGTAGGCG
     TGCCCTGAAA GGTTTTACAG CATTGTTGAG GCGGGGTAAC TGCGTTTACC CGCCATCCGC
9661 TGTACGGAAT TCGGAGTGGC GAGCCCTCAG ATCCTGCATA TAAGCAGCTG CTTTTTGCCT
     ACATGCCTTA AGCCTCACCG CTCGGGAGTC TAGGACGTAT ATTCGTCGAC GAAAACGGA
9721 GTACTGGGTC TCTCTG
     CATGACCCAG AGAGAC
```

FIG. 11E

SEQUENCE LISTING

```
<160> NUMBER OF SEQ ID NOS: 47

<210> SEQ ID NO 1
<211> LENGTH: 244
<212> TYPE: PRT
<213> ORGANISM: Homo sapiens

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
            100                 105                 110

Thr Leu Val Thr Val Ser Ser Gly Ser Thr Ser Gly Gly Gly Ser Gly
        115                 120                 125

Gly Gly Ser Gly Gly Gly Ser Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Lys Ala Ser Gln Asp Val Gly Ile Ala Val Ala Trp Tyr Gln Gln Lys
                165                 170                 175

Pro Gly Lys Val Pro Lys Leu Leu Ile Tyr Trp Ala Ser Thr Arg His
            180                 185                 190

Thr Gly Val Pro Asp Arg Phe Ser Gly Ser Gly Ser Gly Thr Asp Phe
        195                 200                 205

Thr Leu Thr Ile Ser Ser Leu Gln Pro Glu Asp Val Ala Thr Tyr Tyr
    210                 215                 220

Cys Gln Gln Tyr Ser Ser Tyr Pro Tyr Thr Phe Gly Gln Gly Thr Lys
225                 230                 235                 240

Val Glu Ile Lys

<210> SEQ ID NO 2
<211> LENGTH: 10
<212> TYPE: PRT
<213> ORGANISM: Artificial Sequence
<220> FEATURE:
<223> OTHER INFORMATION: linker

<400> SEQUENCE: 2
```

```
Gly Gly Gly Ser Ser Gly Gly Gly Ser Gly
1               5                  10

<210> SEQ ID NO 3
<211> LENGTH: 12
<212> TYPE: PRT
<213> ORGANISM: Artificial Sequence
<220> FEATURE:
<223> OTHER INFORMATION: IgG4 hinge S228P

<400> SEQUENCE: 3

Glu Ser Lys Tyr Gly Pro Pro Cys Pro Pro Cys Pro
1               5                  10

<210> SEQ ID NO 4
<211> LENGTH: 12
<212> TYPE: PRT
<213> ORGANISM: Artificial Sequence
<220> FEATURE:
<223> OTHER INFORMATION: IgG4 hinge

<400> SEQUENCE: 4

Glu Ser Lys Tyr Gly Pro Pro Cys Pro Ser Cys Pro
1               5                  10

<210> SEQ ID NO 5
<211> LENGTH: 22
<212> TYPE: PRT
<213> ORGANISM: Artificial Sequence
<220> FEATURE:
<223> OTHER INFORMATION: IgG4 hinge (S228P)+ linker

<400> SEQUENCE: 5

Glu Ser Lys Tyr Gly Pro Pro Cys Pro Cys Pro Gly Gly Gly Ser
1               5                  10                  15

Ser Gly Gly Gly Ser Gly
            20

<210> SEQ ID NO 6
<211> LENGTH: 39
<212> TYPE: PRT
<213> ORGANISM: Artificial Sequence
<220> FEATURE:
<223> OTHER INFORMATION: CD28 hinge

<400> SEQUENCE: 6

Ile Glu Val Met Tyr Pro Pro Pro Tyr Leu Asp Asn Glu Lys Ser Asn
1               5                  10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 7
<211> LENGTH: 48
<212> TYPE: PRT
<213> ORGANISM: Artificial Sequence
<220> FEATURE:
<223> OTHER INFORMATION: CD8 hinge

<400> SEQUENCE: 7

Ala Lys Pro Thr Thr Thr Pro Ala Pro Arg Pro Pro Thr Pro Ala Pro
1               5                  10                  15

Thr Ile Ala Ser Gln Pro Leu Ser Leu Arg Pro Glu Ala Cys Arg Pro
```

```
                  20                  25                  30

Ala Ala Gly Gly Ala Val His Thr Arg Gly Leu Asp Phe Ala Cys Asp
        35                  40                  45

<210> SEQ ID NO 8
<211> LENGTH: 45
<212> TYPE: PRT
<213> ORGANISM: Artificial Sequence
<220> FEATURE:
<223> OTHER INFORMATION: CD8 hinge

<400> SEQUENCE: 8

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 9
<211> LENGTH: 129
<212> TYPE: PRT
<213> ORGANISM: Artificial Sequence
<220> FEATURE:
<223> OTHER INFORMATION: IgG4(HL-CH3) includes S228P in hinge

<400> SEQUENCE: 9

Glu Ser Lys Tyr Gly Pro Pro Cys Pro Pro Cys Pro Gly Gly Gly Ser
1               5                   10                  15

Ser Gly Gly Gly Ser Gly Gly Gln Pro Arg Glu Pro Gln Val Tyr Thr
            20                  25                  30

Leu Pro Pro Ser Gln Glu Glu Met Thr Lys Asn Gln Val Ser Leu Thr
            35                  40                  45

Cys Leu Val Lys Gly Phe Tyr Pro Ser Asp Ile Ala Val Glu Trp Glu
        50                  55                  60

Ser Asn Gly Gln Pro Glu Asn Asn Tyr Lys Thr Thr Pro Pro Val Leu
65                  70                  75                  80

Asp Ser Asp Gly Ser Phe Phe Leu Tyr Ser Arg Leu Thr Val Asp Lys
                85                  90                  95

Ser Arg Trp Gln Glu Gly Asn Val Phe Ser Cys Ser Val Met His Glu
            100                 105                 110

Ala Leu His Asn His Tyr Thr Gln Lys Ser Leu Ser Leu Ser Leu Gly
        115                 120                 125

Lys

<210> SEQ ID NO 10
<211> LENGTH: 229
<212> TYPE: PRT
<213> ORGANISM: Artificial Sequence
<220> FEATURE:
<223> OTHER INFORMATION: IgG4(L235E,N297Q)

<400> SEQUENCE: 10

Glu Ser Lys Tyr Gly Pro Pro Cys Pro Ser Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45
```

-continued

Ser Gln Glu Asp Pro Glu Val Gln Phe Asn Trp Tyr Val Asp Gly Val
    50                  55                  60

Glu Val His Gln Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 11
<211> LENGTH: 229
<212> TYPE: PRT
<213> ORGANISM: Artificial Sequence
<220> FEATURE:
<223> OTHER INFORMATION: IgG4(S228P, L235E, N297Q)

<400> SEQUENCE: 11

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Gln Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

-continued

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 12
<211> LENGTH: 107
<212> TYPE: PRT
<213> ORGANISM: Homo sapiens

<400> SEQUENCE: 12

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 13
<211> LENGTH: 21
<212> TYPE: PRT
<213> ORGANISM: Artificial Sequence
<220> FEATURE:
<223> OTHER INFORMATION: CD3z transmembrane Domain

<400> SEQUENCE: 13

Leu Cys Tyr Leu Leu Asp Gly Ile Leu Phe Ile Tyr Gly Val Ile Leu
1               5                   10                  15

Thr Ala Leu Phe Leu
            20

<210> SEQ ID NO 14
<211> LENGTH: 27
<212> TYPE: PRT
<213> ORGANISM: Artificial Sequence
<220> FEATURE:
<223> OTHER INFORMATION: CD28 transmembrane Domain

<400> SEQUENCE: 14

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 15
<211> LENGTH: 28
<212> TYPE: PRT
<213> ORGANISM: Artificial Sequence
<220> FEATURE:

-continued

<223> OTHER INFORMATION: CD28M transmembrane Domain

<400> SEQUENCE: 15

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25

<210> SEQ ID NO 16
<211> LENGTH: 22
<212> TYPE: PRT
<213> ORGANISM: Artificial Sequence
<220> FEATURE:
<223> OTHER INFORMATION: CD4 transmembrane Domain

<400> SEQUENCE: 16

Met Ala Leu Ile Val Leu Gly Gly Val Ala Gly Leu Leu Leu Phe Ile
1               5                   10                  15

Gly Leu Gly Ile Phe Phe
            20

<210> SEQ ID NO 17
<211> LENGTH: 21
<212> TYPE: PRT
<213> ORGANISM: Artificial Sequence
<220> FEATURE:
<223> OTHER INFORMATION: CD8tm transmembrane Domain

<400> SEQUENCE: 17

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 18
<211> LENGTH: 23
<212> TYPE: PRT
<213> ORGANISM: Artificial Sequence
<220> FEATURE:
<223> OTHER INFORMATION: CD8tm2 transmembrane Domain

<400> SEQUENCE: 18

Ile Tyr Ile Trp Ala Pro Leu Ala Gly Thr Cys Gly Val Leu Leu Leu
1               5                   10                  15

Ser Leu Val Ile Thr Leu Tyr
            20

<210> SEQ ID NO 19
<211> LENGTH: 24
<212> TYPE: PRT
<213> ORGANISM: Artificial Sequence
<220> FEATURE:
<223> OTHER INFORMATION: CD8tm3 transmembrane Domain

<400> SEQUENCE: 19

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 20
<211> LENGTH: 27
<212> TYPE: PRT
<213> ORGANISM: Artificial Sequence

```
<220> FEATURE:
<223> OTHER INFORMATION: 41BB transmembrane Domain

<400> SEQUENCE: 20

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 21
<211> LENGTH: 112
<212> TYPE: PRT
<213> ORGANISM: Artificial Sequence
<220> FEATURE:
<223> OTHER INFORMATION: CD3 costimulatory domain

<400> SEQUENCE: 21

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 22
<211> LENGTH: 41
<212> TYPE: PRT
<213> ORGANISM: Artificial Sequence
<220> FEATURE:
<223> OTHER INFORMATION: CD28 costimulatory domain

<400> SEQUENCE: 22

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 23
<211> LENGTH: 41
<212> TYPE: PRT
<213> ORGANISM: Artificial Sequence
<220> FEATURE:
<223> OTHER INFORMATION: CD28gg* costimulatory domain

<400> SEQUENCE: 23

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

```
<210> SEQ ID NO 24
<211> LENGTH: 42
<212> TYPE: PRT
<213> ORGANISM: Artificial Sequence
<220> FEATURE:
<223> OTHER INFORMATION: 41BB costimulatory domain

<400> SEQUENCE: 24

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 25
<211> LENGTH: 42
<212> TYPE: PRT
<213> ORGANISM: Artificial Sequence
<220> FEATURE:
<223> OTHER INFORMATION: OX40, costimulatory domain

<400> SEQUENCE: 25

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile
        35                  40

<210> SEQ ID NO 26
<211> LENGTH: 22
<212> TYPE: PRT
<213> ORGANISM: Homo sapiens

<400> SEQUENCE: 26

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 27
<211> LENGTH: 24
<212> TYPE: PRT
<213> ORGANISM: Artificial Sequence
<220> FEATURE:
<223> OTHER INFORMATION: CD3z signaling domain

<400> SEQUENCE: 27

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 28
<211> LENGTH: 354
<212> TYPE: PRT
<213> ORGANISM: Artificial Sequence
<220> FEATURE:
<223> OTHER INFORMATION: truncated EGVF

<400> SEQUENCE: 28
```

```
Leu Val Thr Ser Leu Leu Cys Glu Leu Pro His Pro Ala Phe Leu
1               5                   10                  15

Leu Ile Pro Arg Lys Val Cys Asn Gly Ile Gly Ile Gly Glu Phe Lys
            20                  25                  30

Asp Ser Leu Ser Ile Asn Ala Thr Asn Ile Lys His Phe Lys Asn Cys
            35                  40                  45

Thr Ser Ile Ser Gly Asp Leu His Ile Leu Pro Val Ala Phe Arg Gly
        50                  55                  60

Asp Ser Phe Thr His Thr Pro Pro Leu Asp Pro Gln Glu Leu Asp Ile
65                  70                  75                  80

Leu Lys Thr Val Lys Glu Ile Thr Gly Phe Leu Leu Ile Gln Ala Trp
                85                  90                  95

Pro Glu Asn Arg Thr Asp Leu His Ala Phe Glu Asn Leu Glu Ile Ile
            100                 105                 110

Arg Gly Arg Thr Lys Gln His Gly Gln Phe Ser Leu Ala Val Val Ser
            115                 120                 125

Leu Asn Ile Thr Ser Leu Gly Leu Arg Ser Leu Lys Glu Ile Ser Asp
        130                 135                 140

Gly Asp Val Ile Ile Ser Gly Asn Lys Asn Leu Cys Tyr Ala Asn Thr
145                 150                 155                 160

Ile Asn Trp Lys Lys Leu Phe Gly Thr Ser Gly Gln Lys Thr Lys Ile
                165                 170                 175

Ile Ser Asn Arg Gly Glu Asn Ser Cys Lys Ala Thr Gly Gln Val Cys
            180                 185                 190

His Ala Leu Cys Ser Pro Glu Gly Cys Trp Gly Pro Glu Pro Arg Asp
        195                 200                 205

Cys Val Ser Cys Arg Asn Val Ser Arg Gly Arg Glu Cys Val Asp Lys
210                 215                 220

Cys Asn Leu Leu Glu Gly Glu Pro Arg Glu Phe Val Glu Asn Ser Glu
225                 230                 235                 240

Cys Ile Gln Cys His Pro Glu Cys Leu Pro Gln Ala Met Asn Ile Thr
                245                 250                 255

Cys Thr Gly Arg Gly Pro Asp Asn Cys Ile Gln Cys Ala His Tyr Ile
            260                 265                 270

Asp Gly Pro His Cys Val Lys Thr Cys Pro Ala Gly Val Met Gly Glu
        275                 280                 285

Asn Asn Thr Leu Val Trp Lys Tyr Ala Asp Ala Gly His Val Cys His
        290                 295                 300

Leu Cys His Pro Asn Cys Thr Tyr Gly Cys Thr Gly Pro Gly Leu Glu
305                 310                 315                 320

Gly Cys Pro Thr Asn Gly Pro Lys Ile Pro Ser Ile Ala Thr Gly Met
                325                 330                 335

Val Gly Ala Leu Leu Leu Leu Val Ala Leu Gly Ile Gly Leu
            340                 345                 350

Phe Met
```

<210> SEQ ID NO 29
<211> LENGTH: 960
<212> TYPE: PRT
<213> ORGANISM: Artificial Sequence
<220> FEATURE:
<223> OTHER INFORMATION: CS1 CAR

<400> SEQUENCE: 29

Met Leu Leu Leu Val Thr Ser Leu Leu Leu Cys Glu Leu Pro His Pro

-continued

```
1               5                   10                  15
Ala Phe Leu Leu Ile Pro Glu Val Gln Leu Val Glu Ser Gly Gly Gly
                20                  25                  30
Leu Val Gln Pro Gly Gly Ser Leu Arg Leu Ser Cys Ala Ala Ser Gly
                35                  40                  45
Phe Asp Phe Ser Arg Tyr Trp Met Ser Trp Val Arg Gln Ala Pro Gly
                50                  55                  60
Lys Gly Leu Glu Trp Ile Gly Glu Ile Asn Pro Asp Ser Ser Thr Ile
 65                 70                  75                  80
Asn Tyr Ala Pro Ser Leu Lys Asp Lys Phe Ile Ile Ser Arg Asp Asn
                85                  90                  95
Ala Lys Asn Ser Leu Tyr Leu Gln Met Asn Ser Leu Arg Ala Glu Asp
                100                 105                 110
Thr Ala Val Tyr Tyr Cys Ala Arg Pro Asp Gly Asn Tyr Trp Tyr Phe
                115                 120                 125
Asp Val Trp Gly Gln Gly Thr Leu Val Thr Val Ser Ser Gly Ser Thr
                130                 135                 140
Ser Gly Gly Gly Ser Gly Gly Gly Ser Gly Gly Gly Ser Ser Asp
145                 150                 155                 160
Ile Gln Met Thr Gln Ser Pro Ser Ser Leu Ser Ala Ser Val Gly Asp
                165                 170                 175
Arg Val Thr Ile Thr Cys Lys Ala Ser Gln Asp Val Gly Ile Ala Val
                180                 185                 190
Ala Trp Tyr Gln Gln Lys Pro Gly Lys Val Pro Lys Leu Leu Ile Tyr
                195                 200                 205
Trp Ala Ser Thr Arg His Thr Gly Val Pro Asp Arg Phe Ser Gly Ser
                210                 215                 220
Gly Ser Gly Thr Asp Phe Thr Leu Thr Ile Ser Ser Leu Gln Pro Glu
225                 230                 235                 240
Asp Val Ala Thr Tyr Tyr Cys Gln Gln Tyr Ser Ser Tyr Pro Tyr Thr
                245                 250                 255
Phe Gly Gln Gly Thr Lys Val Glu Ile Lys Glu Ser Lys Tyr Gly Pro
                260                 265                 270
Pro Cys Pro Pro Cys Pro Gly Gly Ser Gly Gly Gly Ser Gly
                275                 280                 285
Gly Gln Pro Arg Glu Pro Gln Val Tyr Thr Leu Pro Pro Ser Gln Glu
                290                 295                 300
Glu Met Thr Lys Asn Gln Val Ser Leu Thr Cys Leu Val Lys Gly Phe
305                 310                 315                 320
Tyr Pro Ser Asp Ile Ala Val Glu Trp Glu Ser Asn Gly Gln Pro Glu
                325                 330                 335
Asn Asn Tyr Lys Thr Thr Pro Pro Val Leu Asp Ser Asp Gly Ser Phe
                340                 345                 350
Phe Leu Tyr Ser Arg Leu Thr Val Asp Lys Ser Arg Trp Gln Glu Gly
                355                 360                 365
Asn Val Phe Ser Cys Ser Val Met His Glu Ala Leu His Asn His Tyr
                370                 375                 380
Thr Gln Lys Ser Leu Ser Leu Ser Leu Gly Lys Met Phe Trp Val Leu
385                 390                 395                 400
Val Val Val Gly Gly Val Leu Ala Cys Tyr Ser Leu Leu Val Thr Val
                405                 410                 415
Ala Phe Ile Ile Phe Trp Val Arg Ser Lys Arg Ser Arg Gly Gly His
                420                 425                 430
```

-continued

```
Ser Asp Tyr Met Asn Met Thr Pro Arg Arg Pro Gly Pro Thr Arg Lys
        435                 440                 445

His Tyr Gln Pro Tyr Ala Pro Pro Arg Asp Phe Ala Ala Tyr Arg Ser
    450                 455                 460

Gly Gly Gly Arg Val Lys Phe Ser Arg Ser Ala Asp Ala Pro Ala Tyr
465                 470                 475                 480

Gln Gln Gly Gln Asn Gln Leu Tyr Asn Glu Leu Asn Leu Gly Arg Arg
                485                 490                 495

Glu Glu Tyr Asp Val Leu Asp Lys Arg Gly Arg Asp Pro Glu Met
                500                 505                 510

Gly Gly Lys Pro Arg Arg Lys Asn Pro Gln Glu Gly Leu Tyr Asn Glu
                515                 520                 525

Leu Gln Lys Asp Lys Met Ala Glu Ala Tyr Ser Glu Ile Gly Met Lys
    530                 535                 540

Gly Glu Arg Arg Arg Gly Lys Gly His Asp Gly Leu Tyr Gln Gly Leu
545                 550                 555                 560

Ser Thr Ala Thr Lys Asp Thr Tyr Asp Ala Leu His Met Gln Ala Leu
                565                 570                 575

Pro Pro Arg Leu Glu Gly Gly Gly Glu Gly Arg Gly Ser Leu Leu Thr
            580                 585                 590

Cys Gly Asp Val Glu Glu Asn Pro Gly Pro Arg Met Leu Leu Leu Val
                595                 600                 605

Thr Ser Leu Leu Leu Cys Glu Leu Pro His Pro Ala Phe Leu Leu Ile
            610                 615                 620

Pro Arg Lys Val Cys Asn Gly Ile Gly Ile Gly Glu Phe Lys Asp Ser
625                 630                 635                 640

Leu Ser Ile Asn Ala Thr Asn Ile Lys His Phe Lys Asn Cys Thr Ser
                645                 650                 655

Ile Ser Gly Asp Leu His Ile Leu Pro Val Ala Phe Arg Gly Asp Ser
                660                 665                 670

Phe Thr His Thr Pro Pro Leu Asp Pro Gln Glu Leu Asp Ile Leu Lys
            675                 680                 685

Thr Val Lys Glu Ile Thr Gly Phe Leu Leu Ile Gln Ala Trp Pro Glu
            690                 695                 700

Asn Arg Thr Asp Leu His Ala Phe Glu Asn Leu Glu Ile Ile Arg Gly
705                 710                 715                 720

Arg Thr Lys Gln His Gly Gln Phe Ser Leu Ala Val Val Ser Leu Asn
                725                 730                 735

Ile Thr Ser Leu Gly Leu Arg Ser Leu Lys Glu Ile Ser Asp Gly Asp
            740                 745                 750

Val Ile Ile Ser Gly Asn Lys Asn Leu Cys Tyr Ala Asn Thr Ile Asn
            755                 760                 765

Trp Lys Lys Leu Phe Gly Thr Ser Gly Gln Lys Thr Lys Ile Ile Ser
    770                 775                 780

Asn Arg Gly Glu Asn Ser Cys Lys Ala Thr Gly Gln Val Cys His Ala
785                 790                 795                 800

Leu Cys Ser Pro Glu Gly Cys Trp Gly Pro Glu Pro Arg Asp Cys Val
                805                 810                 815

Ser Cys Arg Asn Val Ser Arg Gly Arg Glu Cys Val Asp Lys Cys Asn
                820                 825                 830

Leu Leu Glu Gly Glu Pro Arg Glu Phe Val Glu Asn Ser Glu Cys Ile
            835                 840                 845
```

Gln Cys His Pro Glu Cys Leu Pro Gln Ala Met Asn Ile Thr Cys Thr
             850                 855                 860

Gly Arg Gly Pro Asp Asn Cys Ile Gln Cys Ala His Tyr Ile Asp Gly
865                 870                 875                 880

Pro His Cys Val Lys Thr Cys Pro Ala Gly Val Met Gly Glu Asn Asn
                885                 890                 895

Thr Leu Val Trp Lys Tyr Ala Asp Ala Gly His Val Cys His Leu Cys
                900                 905                 910

His Pro Asn Cys Thr Tyr Gly Cys Thr Gly Pro Gly Leu Glu Gly Cys
            915                 920                 925

Pro Thr Asn Gly Pro Lys Ile Pro Ser Ile Ala Thr Gly Met Val Gly
        930                 935                 940

Ala Leu Leu Leu Leu Val Ala Leu Gly Ile Gly Leu Phe Met
945                 950                 955                 960

<210> SEQ ID NO 30
<211> LENGTH: 579
<212> TYPE: PRT
<213> ORGANISM: Artificial Sequence
<220> FEATURE:
<223> OTHER INFORMATION: CS1 CAR excluding T2A and EGFRt

<400> SEQUENCE: 30

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Asp Phe Ser Arg Tyr Trp Met Ser Trp Val Arg Gln Ala Pro Gly
    50                  55                  60

Lys Gly Leu Glu Trp Ile Gly Glu Ile Asn Pro Asp Ser Ser Thr Ile
65                  70                  75                  80

Asn Tyr Ala Pro Ser Leu Lys Asp Lys Phe Ile Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Pro Asp Gly Asn Tyr Trp Tyr Phe
        115                 120                 125

Asp Val Trp Gly Gln Gly Thr Leu Val Thr Val Ser Ser Gly Ser Thr
    130                 135                 140

Ser Gly Gly Gly Ser Gly Gly Gly Gly Gly Gly Ser Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ala Ser Gln Asp Val Gly Ile Ala Val
            180                 185                 190

Ala Trp Tyr Gln Gln Lys Pro Gly Lys Val Pro Lys Leu Leu Ile Tyr
        195                 200                 205

Trp Ala Ser Thr Arg His Thr Gly Val Pro Asp Arg Phe Ser Gly Ser
    210                 215                 220

Gly Ser Gly Thr Asp Phe Thr Leu Thr Ile Ser Ser Leu Gln Pro Glu
225                 230                 235                 240

Asp Val Ala Thr Tyr Tyr Cys Gln Gln Tyr Ser Ser Tyr Pro Tyr Thr
                245                 250                 255

-continued

```
Phe Gly Gln Gly Thr Lys Val Glu Ile Lys Glu Ser Lys Tyr Gly Pro
            260                 265                 270

Pro Cys Pro Pro Cys Pro Gly Gly Ser Gly Gly Gly Ser Gly
        275                 280                 285

Gly Gln Pro Arg Glu Pro Gln Val Tyr Thr Leu Pro Pro Ser Gln Glu
    290                 295                 300

Glu Met Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
                325                 330                 335

Asn Asn Tyr Lys Thr Thr Pro Pro Val Leu Asp Ser Asp Gly Ser Phe
            340                 345                 350

Phe Leu Tyr Ser Arg Leu Thr Val Asp Lys Ser Arg Trp Gln Glu Gly
        355                 360                 365

Asn Val Phe Ser Cys Ser Val Met His Glu Ala Leu His Asn His Tyr
    370                 375                 380

Thr Gln Lys Ser Leu Ser Leu Ser Leu Gly Lys Met Phe Trp Val Leu
385                 390                 395                 400

Val Val Val Gly Gly Val Leu Ala Cys Tyr Ser Leu Leu Val Thr Val
                405                 410                 415

Ala Phe Ile Ile Phe Trp Val Arg Ser Lys Arg Ser Arg Gly Gly His
            420                 425                 430

Ser Asp Tyr Met Asn Met Thr Pro Arg Arg Pro Gly Pro Thr Arg Lys
        435                 440                 445

His Tyr Gln Pro Tyr Ala Pro Pro Arg Asp Phe Ala Ala Tyr Arg Ser
    450                 455                 460

Gly Gly Gly Arg Val Lys Phe Ser Arg Ser Ala Asp Ala Pro Ala Tyr
465                 470                 475                 480

Gln Gln Gly Gln Asn Gln Leu Tyr Asn Glu Leu Asn Leu Gly Arg Arg
                485                 490                 495

Glu Glu Tyr Asp Val Leu Asp Lys Arg Arg Gly Arg Asp Pro Glu Met
            500                 505                 510

Gly Gly Lys Pro Arg Arg Lys Asn Pro Gln Glu Gly Leu Tyr Asn Glu
        515                 520                 525

Leu Gln Lys Asp Lys Met Ala Glu Ala Tyr Ser Glu Ile Gly Met Lys
    530                 535                 540

Gly Glu Arg Arg Arg Gly Lys Gly His Asp Gly Leu Tyr Gln Gly Leu
545                 550                 555                 560

Ser Thr Ala Thr Lys Asp Thr Tyr Asp Ala Leu His Met Gln Ala Leu
                565                 570                 575

Pro Pro Arg
```

```
<210> SEQ ID NO 31
<211> LENGTH: 557
<212> TYPE: PRT
<213> ORGANISM: Artificial Sequence
<220> FEATURE:
<223> OTHER INFORMATION: CS1 CAR excluding GMCSFRa signal, T2A and EGFRt

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
```

```
                35                  40                  45
Gly Glu Ile Asn Pro Asp Ser Ser Thr Ile Asn Tyr Ala Pro Ser Leu
 50                  55                  60

Lys Asp Lys Phe Ile Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Pro Asp Gly Asn Tyr Trp Tyr Phe Asp Val Trp Gly Gln Gly
                100                 105                 110

Thr Leu Val Thr Val Ser Ser Gly Ser Thr Gly Gly Ser Gly
                115                 120                 125

Gly Gly Ser Gly Gly Gly Ser Asp Ile Gln Met Thr Gln Ser
130                 135                 140

Pro Ser Ser Leu Ser Ala Ser Val Gly Asp Arg Val Thr Ile Thr Cys
145                 150                 155                 160

Lys Ala Ser Gln Asp Val Gly Ile Ala Val Ala Trp Tyr Gln Gln Lys
                165                 170                 175

Pro Gly Lys Val Pro Lys Leu Leu Ile Tyr Trp Ala Ser Thr Arg His
                180                 185                 190

Thr Gly Val Pro Asp Arg Phe Ser Gly Ser Gly Ser Gly Thr Asp Phe
                195                 200                 205

Thr Leu Thr Ile Ser Ser Leu Gln Pro Glu Asp Val Ala Thr Tyr Tyr
210                 215                 220

Cys Gln Gln Tyr Ser Ser Tyr Pro Tyr Thr Phe Gly Gln Gly Thr Lys
225                 230                 235                 240

Val Glu Ile Lys Glu Ser Lys Tyr Gly Pro Pro Cys Pro Pro Cys Pro
                245                 250                 255

Gly Gly Gly Ser Ser Gly Gly Gly Ser Gly Gly Gln Pro Arg Glu Pro
                260                 265                 270

Gln Val Tyr Thr Leu Pro Pro Ser Gln Glu Glu Met Thr Lys Asn Gln
                275                 280                 285

Val Ser Leu Thr Cys Leu Val Lys Gly Phe Tyr Pro Ser Asp Ile Ala
290                 295                 300

Val Glu Trp Glu Ser Asn Gly Gln Pro Glu Asn Asn Tyr Lys Thr Thr
305                 310                 315                 320

Pro Pro Val Leu Asp Ser Asp Gly Ser Phe Phe Leu Tyr Ser Arg Leu
                325                 330                 335

Thr Val Asp Lys Ser Arg Trp Gln Glu Gly Asn Val Phe Ser Cys Ser
                340                 345                 350

Val Met His Glu Ala Leu His Asn His Tyr Thr Gln Lys Ser Leu Ser
                355                 360                 365

Leu Ser Leu Gly Lys Met Phe Trp Val Leu Val Val Val Gly Gly Val
                370                 375                 380

Leu Ala Cys Tyr Ser Leu Leu Val Thr Val Ala Phe Ile Ile Phe Trp
385                 390                 395                 400

Val Arg Ser Lys Arg Ser Arg Gly Gly His Ser Asp Tyr Met Asn Met
                405                 410                 415

Thr Pro Arg Arg Pro Gly Pro Thr Arg Lys His Tyr Gln Pro Tyr Ala
                420                 425                 430

Pro Pro Arg Asp Phe Ala Ala Tyr Arg Ser Gly Gly Gly Arg Val Lys
                435                 440                 445

Phe Ser Arg Ser Ala Asp Ala Pro Ala Tyr Gln Gln Gly Gln Asn Gln
450                 455                 460
```

```
Leu Tyr Asn Glu Leu Asn Leu Gly Arg Arg Glu Tyr Asp Val Leu
465                 470                 475                 480

Asp Lys Arg Arg Gly Arg Asp Pro Glu Met Gly Gly Lys Pro Arg Arg
                485                 490                 495

Lys Asn Pro Gln Glu Gly Leu Tyr Asn Glu Leu Gln Lys Asp Lys Met
            500                 505                 510

Ala Glu Ala Tyr Ser Glu Ile Gly Met Lys Gly Glu Arg Arg Arg Gly
        515                 520                 525

Lys Gly His Asp Gly Leu Tyr Gln Gly Leu Ser Thr Ala Thr Lys Asp
    530                 535                 540

Thr Tyr Asp Ala Leu His Met Gln Ala Leu Pro Pro Arg
545                 550                 555
```

<210> SEQ ID NO 32
<211> LENGTH: 955
<212> TYPE: PRT
<213> ORGANISM: Artificial Sequence
<220> FEATURE:
<223> OTHER INFORMATION: CS1scFv-IgG4(HL-CH3)-CD4tm-41BB-Zeta-T2A-EGFRt

<400> SEQUENCE: 32

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Asp Phe Ser Arg Tyr Trp Met Ser Trp Val Arg Gln Ala Pro Gly
    50                  55                  60

Lys Gly Leu Glu Trp Ile Gly Glu Ile Asn Pro Asp Ser Ser Thr Ile
65                  70                  75                  80

Asn Tyr Ala Pro Ser Leu Lys Asp Lys Phe Ile Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Pro Asp Gly Asn Tyr Trp Tyr Phe
        115                 120                 125

Asp Val Trp Gly Gln Gly Thr Leu Val Thr Val Ser Ser Gly Ser Thr
    130                 135                 140

Ser Gly Gly Gly Ser Gly Gly Gly Ser Gly Gly Gly Ser Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ala Ser Gln Asp Val Gly Ile Ala Val
            180                 185                 190

Ala Trp Tyr Gln Gln Lys Pro Gly Lys Val Pro Lys Leu Leu Ile Tyr
        195                 200                 205

Trp Ala Ser Thr Arg His Thr Gly Val Pro Asp Arg Phe Ser Gly Ser
    210                 215                 220

Gly Ser Gly Thr Asp Phe Thr Leu Thr Ile Ser Ser Leu Gln Pro Glu
225                 230                 235                 240

Asp Val Ala Thr Tyr Tyr Cys Gln Gln Tyr Ser Ser Tyr Pro Tyr Thr
                245                 250                 255

Phe Gly Gln Gly Thr Lys Val Glu Ile Lys Glu Ser Lys Tyr Gly Pro
            260                 265                 270
```

```
Pro Cys Pro Cys Pro Gly Gly Gly Ser Ser Gly Gly Gly Ser Gly
        275                 280                 285

Gly Gln Pro Arg Glu Pro Gln Val Tyr Thr Leu Pro Pro Ser Gln Glu
    290                 295                 300

Glu Met Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
                325                 330                 335

Asn Asn Tyr Lys Thr Thr Pro Pro Val Leu Asp Ser Asp Gly Ser Phe
            340                 345                 350

Phe Leu Tyr Ser Arg Leu Thr Val Asp Lys Ser Arg Trp Gln Glu Gly
        355                 360                 365

Asn Val Phe Ser Cys Ser Val Met His Glu Ala Leu His Asn His Tyr
    370                 375                 380

Thr Gln Lys Ser Leu Ser Leu Ser Leu Gly Lys Met Ala Leu Ile Val
385                 390                 395                 400

Leu Gly Gly Val Ala Gly Leu Leu Leu Phe Ile Gly Leu Gly Ile Phe
                405                 410                 415

Phe Lys Arg Gly Arg Lys Lys Leu Leu Tyr Ile Phe Lys Gln Pro Phe
            420                 425                 430

Met Arg Pro Val Gln Thr Thr Gln Glu Glu Asp Gly Cys Ser Cys Arg
        435                 440                 445

Phe Pro Glu Glu Glu Glu Gly Gly Cys Glu Leu Gly Gly Gly Arg Val
    450                 455                 460

Lys Phe Ser Arg Ser Ala Asp Ala Pro Ala Tyr Gln Gln Gly Gln Asn
465                 470                 475                 480

Gln Leu Tyr Asn Glu Leu Asn Leu Gly Arg Arg Glu Glu Tyr Asp Val
                485                 490                 495

Leu Asp Lys Arg Arg Gly Arg Asp Pro Glu Met Gly Gly Lys Pro Arg
            500                 505                 510

Arg Lys Asn Pro Gln Glu Gly Leu Tyr Asn Glu Leu Gln Lys Asp Lys
        515                 520                 525

Met Ala Glu Ala Tyr Ser Glu Ile Gly Met Lys Gly Glu Arg Arg Arg
    530                 535                 540

Gly Lys Gly His Asp Gly Leu Tyr Gln Gly Leu Ser Thr Ala Thr Lys
545                 550                 555                 560

Asp Thr Tyr Asp Ala Leu His Met Gln Ala Leu Pro Pro Arg Leu Glu
                565                 570                 575

Gly Gly Gly Glu Gly Arg Gly Ser Leu Leu Thr Cys Gly Asp Val Glu
            580                 585                 590

Glu Asn Pro Gly Pro Arg Met Leu Leu Leu Val Thr Ser Leu Leu Leu
        595                 600                 605

Cys Glu Leu Pro His Pro Ala Phe Leu Leu Ile Pro Arg Lys Val Cys
    610                 615                 620

Asn Gly Ile Gly Ile Gly Glu Phe Lys Asp Ser Leu Ser Ile Asn Ala
625                 630                 635                 640

Thr Asn Ile Lys His Phe Lys Asn Cys Thr Ser Ile Ser Gly Asp Leu
                645                 650                 655

His Ile Leu Pro Val Ala Phe Arg Gly Asp Ser Phe Thr His Thr Pro
            660                 665                 670

Pro Leu Asp Pro Gln Glu Leu Asp Ile Leu Lys Thr Val Lys Glu Ile
        675                 680                 685
```

Thr Gly Phe Leu Leu Ile Gln Ala Trp Pro Glu Asn Arg Thr Asp Leu
            690                 695                 700

His Ala Phe Glu Asn Leu Glu Ile Ile Arg Gly Arg Thr Lys Gln His
705                 710                 715                 720

Gly Gln Phe Ser Leu Ala Val Val Ser Leu Asn Ile Thr Ser Leu Gly
                725                 730                 735

Leu Arg Ser Leu Lys Glu Ile Ser Asp Gly Asp Val Ile Ile Ser Gly
            740                 745                 750

Asn Lys Asn Leu Cys Tyr Ala Asn Thr Ile Asn Trp Lys Lys Leu Phe
                755                 760                 765

Gly Thr Ser Gly Gln Lys Thr Lys Ile Ile Ser Asn Arg Gly Glu Asn
770                 775                 780

Ser Cys Lys Ala Thr Gly Gln Val Cys His Ala Leu Cys Ser Pro Glu
785                 790                 795                 800

Gly Cys Trp Gly Pro Glu Pro Arg Asp Cys Val Ser Cys Arg Asn Val
                805                 810                 815

Ser Arg Gly Arg Glu Cys Val Asp Lys Cys Asn Leu Leu Glu Gly Glu
            820                 825                 830

Pro Arg Glu Phe Val Glu Asn Ser Glu Cys Ile Gln Cys His Pro Glu
                835                 840                 845

Cys Leu Pro Gln Ala Met Asn Ile Thr Cys Thr Gly Arg Gly Pro Asp
850                 855                 860

Asn Cys Ile Gln Cys Ala His Tyr Ile Asp Gly Pro His Cys Val Lys
865                 870                 875                 880

Thr Cys Pro Ala Gly Val Met Gly Glu Asn Asn Thr Leu Val Trp Lys
                885                 890                 895

Tyr Ala Asp Ala Gly His Val Cys His Leu Cys His Pro Asn Cys Thr
            900                 905                 910

Tyr Gly Cys Thr Gly Pro Gly Leu Glu Gly Cys Pro Thr Asn Gly Pro
                915                 920                 925

Lys Ile Pro Ser Ile Ala Thr Gly Met Val Gly Ala Leu Leu Leu Leu
930                 935                 940

Leu Val Val Ala Leu Gly Ile Gly Leu Phe Met
945                 950                 955

<210> SEQ ID NO 33
<211> LENGTH: 574
<212> TYPE: PRT
<213> ORGANISM: Artificial Sequence
<220> FEATURE:
<223> OTHER INFORMATION: CS1scFv-IgG4(HL-CH3)-CD4tm-41BB-Zeta

<400> SEQUENCE: 33

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
                20                  25                  30

Leu Val Gln Pro Gly Gly Ser Leu Arg Leu Ser Cys Ala Ala Ser Gly
            35                  40                  45

Phe Asp Phe Ser Arg Tyr Trp Met Ser Trp Val Arg Gln Ala Pro Gly
        50                  55                  60

Lys Gly Leu Glu Trp Ile Gly Glu Ile Asn Pro Asp Ser Ser Thr Ile
65                  70                  75                  80

Asn Tyr Ala Pro Ser Leu Lys Asp Lys Phe Ile Ile Ser Arg Asp Asn
                85                  90                  95

```
Ala Lys Asn Ser Leu Tyr Leu Gln Met Asn Ser Leu Arg Ala Glu Asp
             100                 105                 110

Thr Ala Val Tyr Tyr Cys Ala Arg Pro Asp Gly Asn Tyr Trp Tyr Phe
         115                 120                 125

Asp Val Trp Gly Gln Gly Thr Leu Val Thr Val Ser Ser Gly Ser Thr
     130                 135                 140

Ser Gly Gly Gly Ser Gly Gly Gly Ser Gly Gly Gly Ser Ser Asp
145                 150                 155                 160

Ile Gln Met Thr Gln Ser Pro Ser Ser Leu Ser Ala Ser Val Gly Asp
                 165                 170                 175

Arg Val Thr Ile Thr Cys Lys Ala Ser Gln Asp Val Gly Ile Ala Val
             180                 185                 190

Ala Trp Tyr Gln Gln Lys Pro Gly Lys Val Pro Lys Leu Leu Ile Tyr
         195                 200                 205

Trp Ala Ser Thr Arg His Thr Gly Val Pro Asp Arg Phe Ser Gly Ser
     210                 215                 220

Gly Ser Gly Thr Asp Phe Thr Leu Thr Ile Ser Ser Leu Gln Pro Glu
225                 230                 235                 240

Asp Val Ala Thr Tyr Tyr Cys Gln Gln Tyr Ser Ser Tyr Pro Tyr Thr
                 245                 250                 255

Phe Gly Gln Gly Thr Lys Val Glu Ile Lys Glu Ser Lys Tyr Gly Pro
             260                 265                 270

Pro Cys Pro Pro Cys Pro Gly Gly Ser Ser Gly Gly Ser Gly
         275                 280                 285

Gly Gln Pro Arg Glu Pro Gln Val Tyr Thr Leu Pro Pro Ser Gln Glu
     290                 295                 300

Glu Met Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
                 325                 330                 335

Asn Asn Tyr Lys Thr Thr Pro Pro Val Leu Asp Ser Asp Gly Ser Phe
             340                 345                 350

Phe Leu Tyr Ser Arg Leu Thr Val Asp Lys Ser Arg Trp Gln Glu Gly
         355                 360                 365

Asn Val Phe Ser Cys Ser Val Met His Glu Ala Leu His Asn His Tyr
     370                 375                 380

Thr Gln Lys Ser Leu Ser Leu Ser Leu Gly Lys Met Ala Leu Ile Val
385                 390                 395                 400

Leu Gly Gly Val Ala Gly Leu Leu Leu Phe Ile Gly Leu Gly Ile Phe
                 405                 410                 415

Phe Lys Arg Gly Arg Lys Lys Leu Leu Tyr Ile Phe Lys Gln Pro Phe
             420                 425                 430

Met Arg Pro Val Gln Thr Thr Gln Glu Glu Asp Gly Cys Ser Cys Arg
         435                 440                 445

Phe Pro Glu Glu Glu Glu Gly Gly Cys Glu Leu Gly Gly Gly Arg Val
     450                 455                 460

Lys Phe Ser Arg Ser Ala Asp Ala Pro Ala Tyr Gln Gln Gly Gln Asn
465                 470                 475                 480

Gln Leu Tyr Asn Glu Leu Asn Leu Gly Arg Arg Glu Glu Tyr Asp Val
                 485                 490                 495

Leu Asp Lys Arg Arg Gly Arg Asp Pro Glu Met Gly Gly Lys Pro Arg
             500                 505                 510

Arg Lys Asn Pro Gln Glu Gly Leu Tyr Asn Glu Leu Gln Lys Asp Lys
```

```
              515                 520                 525
Met Ala Glu Ala Tyr Ser Glu Ile Gly Met Lys Gly Glu Arg Arg
    530                 535                 540

Gly Lys Gly His Asp Gly Leu Tyr Gln Gly Leu Ser Thr Ala Thr Lys
545                 550                 555                 560

Asp Thr Tyr Asp Ala Leu His Met Gln Ala Leu Pro Pro Arg
                565                 570
```

<210> SEQ ID NO 34
<211> LENGTH: 552
<212> TYPE: PRT
<213> ORGANISM: Artificial Sequence
<220> FEATURE:
<223> OTHER INFORMATION: CS1scFv-IgG4(HL-CH3)-CD4tm-41BB-Zeta excluding
    GMCSFRa signal

<400> SEQUENCE: 34

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
            100                 105                 110

Thr Leu Val Thr Val Ser Ser Gly Ser Thr Ser Gly Gly Gly Ser Gly
        115                 120                 125

Gly Gly Ser Gly Gly Gly Ser Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Lys Ala Ser Gln Asp Val Gly Ile Ala Val Ala Trp Tyr Gln Gln Lys
                165                 170                 175

Pro Gly Lys Val Pro Lys Leu Leu Ile Tyr Trp Ala Ser Thr Arg His
            180                 185                 190

Thr Gly Val Pro Asp Arg Phe Ser Gly Ser Gly Ser Gly Thr Asp Phe
        195                 200                 205

Thr Leu Thr Ile Ser Ser Leu Gln Pro Glu Asp Val Ala Thr Tyr Tyr
    210                 215                 220

Cys Gln Gln Tyr Ser Ser Tyr Pro Tyr Thr Phe Gly Gln Gly Thr Lys
225                 230                 235                 240

Val Glu Ile Lys Glu Ser Lys Tyr Gly Pro Pro Cys Pro Pro Cys Pro
                245                 250                 255

Gly Gly Gly Ser Ser Gly Gly Gly Ser Gly Gly Gln Pro Arg Glu Pro
            260                 265                 270

Gln Val Tyr Thr Leu Pro Pro Ser Gln Glu Glu Met Thr Lys Asn Gln
        275                 280                 285

Val Ser Leu Thr Cys Leu Val Lys Gly Phe Tyr Pro Ser Asp Ile Ala
    290                 295                 300
```

```
Val Glu Trp Glu Ser Asn Gly Gln Pro Glu Asn Asn Tyr Lys Thr Thr
305                 310                 315                 320

Pro Pro Val Leu Asp Ser Asp Gly Ser Phe Phe Leu Tyr Ser Arg Leu
            325                 330                 335

Thr Val Asp Lys Ser Arg Trp Gln Glu Gly Asn Val Phe Ser Cys Ser
        340                 345                 350

Val Met His Glu Ala Leu His Asn His Tyr Thr Gln Lys Ser Leu Ser
    355                 360                 365

Leu Ser Leu Gly Lys Met Ala Leu Ile Val Leu Gly Gly Val Ala Gly
370                 375                 380

Leu Leu Leu Phe Ile Gly Leu Gly Ile Phe Phe Lys Arg Gly Arg Lys
385                 390                 395                 400

Lys Leu Leu Tyr Ile Phe Lys Gln Pro Phe Met Arg Pro Val Gln Thr
                405                 410                 415

Thr Gln Glu Glu Asp Gly Cys Ser Cys Arg Phe Pro Glu Glu Glu Glu
            420                 425                 430

Gly Gly Cys Glu Leu Gly Gly Arg Val Lys Phe Ser Arg Ser Ala
                435                 440                 445

Asp Ala Pro Ala Tyr Gln Gln Gly Gln Asn Gln Leu Tyr Asn Glu Leu
450                 455                 460

Asn Leu Gly Arg Arg Glu Glu Tyr Asp Val Leu Asp Lys Arg Arg Gly
465                 470                 475                 480

Arg Asp Pro Glu Met Gly Gly Lys Pro Arg Arg Lys Asn Pro Gln Glu
                485                 490                 495

Gly Leu Tyr Asn Glu Leu Gln Lys Asp Lys Met Ala Glu Ala Tyr Ser
            500                 505                 510

Glu Ile Gly Met Lys Gly Glu Arg Arg Arg Gly Lys Gly His Asp Gly
                515                 520                 525

Leu Tyr Gln Gly Leu Ser Thr Ala Thr Lys Asp Thr Tyr Asp Ala Leu
530                 535                 540

His Met Gln Ala Leu Pro Pro Arg
545                 550

<210> SEQ ID NO 35
<211> LENGTH: 1055
<212> TYPE: PRT
<213> ORGANISM: Artificial Sequence
<220> FEATURE:
<223> OTHER INFORMATION: CS1scFv-IgG4(L235E,N297Q)-CD4tm-41BB-Zeta-T2A-
      EGFRt

<400> SEQUENCE: 35

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
                20                  25                  30

Leu Val Gln Pro Gly Gly Ser Leu Arg Leu Ser Cys Ala Ala Ser Gly
            35                  40                  45

Phe Asp Phe Ser Arg Tyr Trp Met Ser Trp Val Arg Gln Ala Pro Gly
        50                  55                  60

Lys Gly Leu Glu Trp Ile Gly Glu Ile Asn Pro Asp Ser Ser Thr Ile
65                  70                  75                  80

Asn Tyr Ala Pro Ser Leu Lys Asp Lys Phe Ile Ile Ser Arg Asp Asn
                85                  90                  95

Ala Lys Asn Ser Leu Tyr Leu Gln Met Asn Ser Leu Arg Ala Glu Asp
            100                 105                 110
```

```
Thr Ala Val Tyr Tyr Cys Ala Arg Pro Asp Gly Asn Tyr Trp Tyr Phe
            115                 120                 125

Asp Val Trp Gly Gln Gly Thr Leu Val Thr Val Ser Ser Gly Ser Thr
    130                 135                 140

Ser Gly Gly Gly Ser Gly Gly Gly Ser Gly Gly Gly Ser Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ala Ser Gln Asp Val Gly Ile Ala Val
                180                 185                 190

Ala Trp Tyr Gln Gln Lys Pro Gly Lys Val Pro Lys Leu Leu Ile Tyr
        195                 200                 205

Trp Ala Ser Thr Arg His Thr Gly Val Pro Asp Arg Phe Ser Gly Ser
    210                 215                 220

Gly Ser Gly Thr Asp Phe Thr Leu Thr Ile Ser Ser Leu Gln Pro Glu
225                 230                 235                 240

Asp Val Ala Thr Tyr Tyr Cys Gln Gln Tyr Ser Ser Tyr Pro Tyr Thr
                245                 250                 255

Phe Gly Gln Gly Thr Lys Val Glu Ile Lys Glu Ser Lys Tyr Gly Pro
            260                 265                 270

Pro Cys Pro Pro Cys Pro Ala Pro Glu Phe Glu Gly Gly Pro Ser Val
        275                 280                 285

Phe Leu Phe Pro Pro Lys Pro Lys Asp Thr Leu Met Ile Ser Arg Thr
    290                 295                 300

Pro Glu Val Thr Cys Val Val Val Asp Val Ser Gln Glu Asp Pro Glu
305                 310                 315                 320

Val Gln Phe Asn Trp Tyr Val Asp Gly Val Glu Val His Asn Ala Lys
                325                 330                 335

Thr Lys Pro Arg Glu Glu Gln Phe Gln Ser Thr Tyr Arg Val Val Ser
            340                 345                 350

Val Leu Thr Val Leu His Gln Asp Trp Leu Asn Gly Lys Glu Tyr Lys
        355                 360                 365

Cys Lys Val Ser Asn Lys Gly Leu Pro Ser Ser Ile Glu Lys Thr Ile
    370                 375                 380

Ser Lys Ala Lys Gly Gln Pro Arg Glu Pro Gln Val Tyr Thr Leu Pro
385                 390                 395                 400

Pro Ser Gln Glu Glu Met Thr Lys Asn Gln Val Ser Leu Thr Cys Leu
                405                 410                 415

Val Lys Gly Phe Tyr Pro Ser Asp Ile Ala Val Glu Trp Glu Ser Asn
            420                 425                 430

Gly Gln Pro Glu Asn Asn Tyr Lys Thr Thr Pro Pro Val Leu Asp Ser
        435                 440                 445

Asp Gly Ser Phe Phe Leu Tyr Ser Arg Leu Thr Val Asp Lys Ser Arg
    450                 455                 460

Trp Gln Glu Gly Asn Val Phe Ser Cys Ser Val Met His Glu Ala Leu
465                 470                 475                 480

His Asn His Tyr Thr Gln Lys Ser Leu Ser Leu Ser Leu Gly Lys Met
                485                 490                 495

Ala Leu Ile Val Leu Gly Gly Val Ala Gly Leu Leu Leu Phe Ile Gly
            500                 505                 510

Leu Gly Ile Phe Phe Lys Arg Gly Arg Lys Lys Leu Leu Tyr Ile Phe
        515                 520                 525
```

```
Lys Gln Pro Phe Met Arg Pro Val Gln Thr Thr Gln Glu Glu Asp Gly
    530                 535                 540
Cys Ser Cys Arg Phe Pro Glu Glu Glu Gly Gly Cys Glu Leu Gly
545                 550                 555                 560
Gly Gly Arg Val Lys Phe Ser Arg Ser Ala Asp Ala Pro Ala Tyr Gln
                565                 570                 575
Gln Gly Gln Asn Gln Leu Tyr Asn Glu Leu Asn Leu Gly Arg Arg Glu
                580                 585                 590
Glu Tyr Asp Val Leu Asp Lys Arg Arg Gly Arg Asp Pro Glu Met Gly
        595                 600                 605
Gly Lys Pro Arg Arg Lys Asn Pro Gln Glu Gly Leu Tyr Asn Glu Leu
    610                 615                 620
Gln Lys Asp Lys Met Ala Glu Ala Tyr Ser Glu Ile Gly Met Lys Gly
625                 630                 635                 640
Glu Arg Arg Arg Gly Lys Gly His Asp Gly Leu Tyr Gln Gly Leu Ser
                645                 650                 655
Thr Ala Thr Lys Asp Thr Tyr Asp Ala Leu His Met Gln Ala Leu Pro
                660                 665                 670
Pro Arg Leu Glu Gly Gly Gly Glu Gly Arg Gly Ser Leu Leu Thr Cys
        675                 680                 685
Gly Asp Val Glu Glu Asn Pro Gly Pro Arg Met Leu Leu Leu Val Thr
    690                 695                 700
Ser Leu Leu Leu Cys Glu Leu Pro His Pro Ala Phe Leu Leu Ile Pro
705                 710                 715                 720
Arg Lys Val Cys Asn Gly Ile Gly Ile Gly Glu Phe Lys Asp Ser Leu
                725                 730                 735
Ser Ile Asn Ala Thr Asn Ile Lys His Phe Lys Asn Cys Thr Ser Ile
                740                 745                 750
Ser Gly Asp Leu His Ile Leu Pro Val Ala Phe Arg Gly Asp Ser Phe
        755                 760                 765
Thr His Thr Pro Pro Leu Asp Pro Gln Glu Leu Asp Ile Leu Lys Thr
    770                 775                 780
Val Lys Glu Ile Thr Gly Phe Leu Leu Ile Gln Ala Trp Pro Glu Asn
785                 790                 795                 800
Arg Thr Asp Leu His Ala Phe Glu Asn Leu Glu Ile Ile Arg Gly Arg
                805                 810                 815
Thr Lys Gln His Gly Gln Phe Ser Leu Ala Val Val Ser Leu Asn Ile
                820                 825                 830
Thr Ser Leu Gly Leu Arg Ser Leu Lys Glu Ile Ser Asp Gly Asp Val
        835                 840                 845
Ile Ile Ser Gly Asn Lys Asn Leu Cys Tyr Ala Asn Thr Ile Asn Trp
    850                 855                 860
Lys Lys Leu Phe Gly Thr Ser Gly Gln Lys Thr Lys Ile Ile Ser Asn
865                 870                 875                 880
Arg Gly Glu Asn Ser Cys Lys Ala Thr Gly Gln Val Cys His Ala Leu
                885                 890                 895
Cys Ser Pro Glu Gly Cys Trp Gly Pro Glu Pro Arg Asp Cys Val Ser
                900                 905                 910
Cys Arg Asn Val Ser Arg Gly Arg Glu Cys Val Asp Lys Cys Asn Leu
        915                 920                 925
Leu Glu Gly Glu Pro Arg Glu Phe Val Glu Asn Ser Glu Cys Ile Gln
    930                 935                 940
Cys His Pro Glu Cys Leu Pro Gln Ala Met Asn Ile Thr Cys Thr Gly
```

```
                945                 950                 955                 960
Arg Gly Pro Asp Asn Cys Ile Gln Cys Ala His Tyr Ile Asp Gly Pro
                    965                 970                 975

His Cys Val Lys Thr Cys Pro Ala Gly Val Met Gly Glu Asn Asn Thr
                    980                 985                 990

Leu Val Trp Lys Tyr Ala Asp Ala Gly His Val Cys His Leu Cys His
                    995                 1000                1005

Pro Asn Cys Thr Tyr Gly Cys Thr Gly Pro Gly Leu Glu Gly Cys
    1010                1015                1020

Pro Thr Asn Gly Pro Lys Ile Pro Ser Ile Ala Thr Gly Met Val
    1025                1030                1035

Gly Ala Leu Leu Leu Leu Leu Val Val Ala Leu Gly Ile Gly Leu
    1040                1045                1050

Phe Met
    1055

<210> SEQ ID NO 36
<211> LENGTH: 674
<212> TYPE: PRT
<213> ORGANISM: Artificial Sequence
<220> FEATURE:
<223> OTHER INFORMATION: CS1scFv-IgG4(L235E,N297Q)-CD4tm-41BB-Zeta

<400> SEQUENCE: 36

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
                20                  25                  30

Leu Val Gln Pro Gly Gly Ser Leu Arg Leu Ser Cys Ala Ala Ser Gly
            35                  40                  45

Phe Asp Phe Ser Arg Tyr Trp Met Ser Trp Val Arg Gln Ala Pro Gly
        50                  55                  60

Lys Gly Leu Glu Trp Ile Gly Glu Ile Asn Pro Asp Ser Ser Thr Ile
65                  70                  75                  80

Asn Tyr Ala Pro Ser Leu Lys Asp Lys Phe Ile Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Pro Asp Gly Asn Tyr Trp Tyr Phe
        115                 120                 125

Asp Val Trp Gly Gln Gly Thr Leu Val Thr Val Ser Ser Gly Ser Thr
    130                 135                 140

Ser Gly Gly Gly Ser Gly Gly Gly Ser Gly Gly Gly Ser Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ala Ser Gln Asp Val Gly Ile Ala Val
            180                 185                 190

Ala Trp Tyr Gln Gln Lys Pro Gly Lys Val Pro Lys Leu Leu Ile Tyr
        195                 200                 205

Trp Ala Ser Thr Arg His Thr Gly Val Pro Asp Arg Phe Ser Gly Ser
    210                 215                 220

Gly Ser Gly Thr Asp Phe Thr Leu Thr Ile Ser Ser Leu Gln Pro Glu
225                 230                 235                 240

Asp Val Ala Thr Tyr Tyr Cys Gln Gln Tyr Ser Ser Tyr Pro Tyr Thr
```

```
                245                 250                 255
Phe Gly Gln Gly Thr Lys Val Glu Ile Lys Glu Ser Lys Tyr Gly Pro
                260                 265                 270
Pro Cys Pro Cys Pro Ala Pro Glu Phe Glu Gly Gly Pro Ser Val
            275                 280                 285
Phe Leu Phe Pro Pro Lys Pro Lys Asp Thr Leu Met Ile Ser Arg Thr
            290                 295                 300
Pro Glu Val Thr Cys Val Val Asp Val Ser Gln Glu Asp Pro Glu
305                 310                 315                 320
Val Gln Phe Asn Trp Tyr Val Asp Gly Val Glu Val His Asn Ala Lys
                325                 330                 335
Thr Lys Pro Arg Glu Glu Gln Phe Gln Ser Thr Tyr Arg Val Val Ser
            340                 345                 350
Val Leu Thr Val Leu His Gln Asp Trp Leu Asn Gly Lys Glu Tyr Lys
            355                 360                 365
Cys Lys Val Ser Asn Lys Gly Leu Pro Ser Ser Ile Glu Lys Thr Ile
            370                 375                 380
Ser Lys Ala Lys Gly Gln Pro Arg Glu Pro Gln Val Tyr Thr Leu Pro
385                 390                 395                 400
Pro Ser Gln Glu Glu Met Thr Lys Asn Gln Val Ser Leu Thr Cys Leu
                405                 410                 415
Val Lys Gly Phe Tyr Pro Ser Asp Ile Ala Val Glu Trp Glu Ser Asn
            420                 425                 430
Gly Gln Pro Glu Asn Asn Tyr Lys Thr Thr Pro Pro Val Leu Asp Ser
            435                 440                 445
Asp Gly Ser Phe Phe Leu Tyr Ser Arg Leu Thr Val Asp Lys Ser Arg
            450                 455                 460
Trp Gln Glu Gly Asn Val Phe Ser Cys Ser Val Met His Glu Ala Leu
465                 470                 475                 480
His Asn His Tyr Thr Gln Lys Ser Leu Ser Leu Ser Leu Gly Lys Met
                485                 490                 495
Ala Leu Ile Val Leu Gly Gly Val Ala Gly Leu Leu Leu Phe Ile Gly
            500                 505                 510
Leu Gly Ile Phe Phe Lys Arg Gly Arg Lys Lys Leu Leu Tyr Ile Phe
            515                 520                 525
Lys Gln Pro Phe Met Arg Pro Val Gln Thr Thr Gln Glu Glu Asp Gly
            530                 535                 540
Cys Ser Cys Arg Phe Pro Glu Glu Glu Gly Gly Cys Glu Leu Gly
545                 550                 555                 560
Gly Gly Arg Val Lys Phe Ser Arg Ser Ala Asp Ala Pro Ala Tyr Gln
                565                 570                 575
Gln Gly Gln Asn Gln Leu Tyr Asn Glu Leu Asn Leu Gly Arg Arg Glu
                580                 585                 590
Glu Tyr Asp Val Leu Asp Lys Arg Arg Gly Arg Asp Pro Glu Met Gly
            595                 600                 605
Gly Lys Pro Arg Arg Lys Asn Pro Gln Glu Gly Leu Tyr Asn Glu Leu
            610                 615                 620
Gln Lys Asp Lys Met Ala Glu Ala Tyr Ser Glu Ile Gly Met Lys Gly
625                 630                 635                 640
Glu Arg Arg Arg Gly Lys Gly His Asp Gly Leu Tyr Gln Gly Leu Ser
                645                 650                 655
Thr Ala Thr Lys Asp Thr Tyr Asp Ala Leu His Met Gln Ala Leu Pro
            660                 665                 670
```

Pro Arg

<210> SEQ ID NO 37
<211> LENGTH: 652
<212> TYPE: PRT
<213> ORGANISM: Artificial Sequence
<220> FEATURE:
<223> OTHER INFORMATION: CS1scFv-IgG4(L235E,N297Q)-CD4tm-41BB-Zeta
      excluding GMCSFRa signal

<400> SEQUENCE: 37

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
            100                 105                 110

Thr Leu Val Thr Val Ser Ser Gly Ser Thr Ser Gly Gly Gly Ser Gly
        115                 120                 125

Gly Gly Ser Gly Gly Gly Ser Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Lys Ala Ser Gln Asp Val Gly Ile Ala Val Ala Trp Tyr Gln Gln Lys
                165                 170                 175

Pro Gly Lys Val Pro Lys Leu Leu Ile Tyr Trp Ala Ser Thr Arg His
            180                 185                 190

Thr Gly Val Pro Asp Arg Phe Ser Gly Ser Gly Ser Gly Thr Asp Phe
        195                 200                 205

Thr Leu Thr Ile Ser Ser Leu Gln Pro Glu Asp Val Ala Thr Tyr Tyr
    210                 215                 220

Cys Gln Gln Tyr Ser Ser Tyr Pro Tyr Thr Phe Gly Gln Gly Thr Lys
225                 230                 235                 240

Val Glu Ile Lys Glu Ser Lys Tyr Gly Pro Pro Cys Pro Pro Cys Pro
                245                 250                 255

Ala Pro Glu Phe Glu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser Gln Glu Asp Pro Glu Val Gln Phe Asn Trp Tyr
    290                 295                 300

Val Asp Gly Val Glu Val His Asn Ala Lys Thr Lys Pro Arg Glu Glu
305                 310                 315                 320

Gln Phe Gln Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350
```

```
Gly Leu Pro Ser Ser Ile Glu Lys Thr Ile Ser Lys Ala Lys Gly Gln
            355                 360                 365

Pro Arg Glu Pro Gln Val Tyr Thr Leu Pro Pro Ser Gln Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Arg Leu Thr Val Asp Lys Ser Arg Trp Gln Glu Gly Asn Val
        435                 440                 445

Phe Ser Cys Ser Val Met His Glu Ala Leu His Asn His Tyr Thr Gln
    450                 455                 460

Lys Ser Leu Ser Leu Ser Leu Gly Lys Met Ala Leu Ile Val Leu Gly
465                 470                 475                 480

Gly Val Ala Gly Leu Leu Leu Phe Ile Gly Leu Gly Ile Phe Phe Lys
                485                 490                 495

Arg Gly Arg Lys Lys Leu Leu Tyr Ile Phe Lys Gln Pro Phe Met Arg
            500                 505                 510

Pro Val Gln Thr Thr Gln Glu Glu Asp Gly Cys Ser Cys Arg Phe Pro
        515                 520                 525

Glu Glu Glu Glu Gly Gly Cys Glu Leu Gly Gly Gly Arg Val Lys Phe
    530                 535                 540

Ser Arg Ser Ala Asp Ala Pro Ala Tyr Gln Gln Gly Gln Asn Gln Leu
545                 550                 555                 560

Tyr Asn Glu Leu Asn Leu Gly Arg Arg Glu Glu Tyr Asp Val Leu Asp
                565                 570                 575

Lys Arg Arg Gly Arg Asp Pro Glu Met Gly Gly Lys Pro Arg Arg Lys
            580                 585                 590

Asn Pro Gln Glu Gly Leu Tyr Asn Glu Leu Gln Lys Asp Lys Met Ala
        595                 600                 605

Glu Ala Tyr Ser Glu Ile Gly Met Lys Gly Glu Arg Arg Arg Gly Lys
    610                 615                 620

Gly His Asp Gly Leu Tyr Gln Gly Leu Ser Thr Ala Thr Lys Asp Thr
625                 630                 635                 640

Tyr Asp Ala Leu His Met Gln Ala Leu Pro Pro Arg
                645                 650

<210> SEQ ID NO 38
<211> LENGTH: 1060
<212> TYPE: PRT
<213> ORGANISM: Artificial Sequence
<220> FEATURE:
<223> OTHER INFORMATION: CS1scFv-IgG4(L235E, N297Q)-CD28tm-CD28gg-Zeta-
      T2A-EGFRt

<400> SEQUENCE: 38

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
                20                  25                  30

Leu Val Gln Pro Gly Gly Ser Leu Arg Leu Ser Cys Ala Ala Ser Gly
            35                  40                  45

Phe Asp Phe Ser Arg Tyr Trp Met Ser Trp Val Arg Gln Ala Pro Gly
```

```
                50                  55                  60
Lys Gly Leu Glu Trp Ile Gly Glu Ile Asn Pro Asp Ser Ser Thr Ile
 65                  70                  75                  80

Asn Tyr Ala Pro Ser Leu Lys Asp Lys Phe Ile Ile Ser Arg Asp Asn
                 85                  90                  95

Ala Lys Asn Ser Leu Tyr Leu Gln Met Asn Ser Leu Arg Ala Glu Asp
                100                 105                 110

Thr Ala Val Tyr Tyr Cys Ala Arg Pro Asp Gly Asn Tyr Trp Tyr Phe
                115                 120                 125

Asp Val Trp Gly Gln Gly Thr Leu Val Thr Val Ser Ser Gly Ser Thr
130                 135                 140

Ser Gly Gly Gly Ser Gly Gly Gly Ser Gly Gly Gly Gly Ser Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ala Ser Gln Asp Val Gly Ile Ala Val
                180                 185                 190

Ala Trp Tyr Gln Gln Lys Pro Gly Lys Val Pro Lys Leu Leu Ile Tyr
                195                 200                 205

Trp Ala Ser Thr Arg His Thr Gly Val Pro Asp Arg Phe Ser Gly Ser
210                 215                 220

Gly Ser Gly Thr Asp Phe Thr Leu Thr Ile Ser Ser Leu Gln Pro Glu
225                 230                 235                 240

Asp Val Ala Thr Tyr Tyr Cys Gln Gln Tyr Ser Ser Tyr Pro Tyr Thr
                245                 250                 255

Phe Gly Gln Gly Thr Lys Val Glu Ile Lys Glu Ser Lys Tyr Gly Pro
                260                 265                 270

Pro Cys Pro Pro Cys Pro Ala Pro Glu Phe Glu Gly Gly Pro Ser Val
                275                 280                 285

Phe Leu Phe Pro Pro Lys Pro Lys Asp Thr Leu Met Ile Ser Arg Thr
                290                 295                 300

Pro Glu Val Thr Cys Val Val Val Asp Val Ser Gln Glu Asp Pro Glu
305                 310                 315                 320

Val Gln Phe Asn Trp Tyr Val Asp Gly Val Glu Val His Asn Ala Lys
                325                 330                 335

Thr Lys Pro Arg Glu Glu Gln Phe Gln Ser Thr Tyr Arg Val Val Ser
                340                 345                 350

Val Leu Thr Val Leu His Gln Asp Trp Leu Asn Gly Lys Glu Tyr Lys
                355                 360                 365

Cys Lys Val Ser Asn Lys Gly Leu Pro Ser Ser Ile Glu Lys Thr Ile
                370                 375                 380

Ser Lys Ala Lys Gly Gln Pro Arg Glu Pro Gln Val Tyr Thr Leu Pro
385                 390                 395                 400

Pro Ser Gln Glu Glu Met Thr Lys Asn Gln Val Ser Leu Thr Cys Leu
                405                 410                 415

Val Lys Gly Phe Tyr Pro Ser Asp Ile Ala Val Glu Trp Glu Ser Asn
                420                 425                 430

Gly Gln Pro Glu Asn Asn Tyr Lys Thr Thr Pro Pro Val Leu Asp Ser
                435                 440                 445

Asp Gly Ser Phe Phe Leu Tyr Ser Arg Leu Thr Val Asp Lys Ser Arg
                450                 455                 460

Trp Gln Glu Gly Asn Val Phe Ser Cys Ser Val Met His Glu Ala Leu
465                 470                 475                 480
```

```
His Asn His Tyr Thr Gln Lys Ser Leu Ser Leu Ser Leu Gly Lys Met
            485                 490                 495
Phe Trp Val Leu Val Val Val Gly Gly Val Leu Ala Cys Tyr Ser Leu
            500                 505                 510
Leu Val Thr Val Ala Phe Ile Ile Phe Trp Val Arg Ser Lys Arg Ser
            515                 520                 525
Arg Gly Gly His Ser Asp Tyr Met Asn Met Thr Pro Arg Arg Pro Gly
            530                 535                 540
Pro Thr Arg Lys His Tyr Gln Pro Tyr Ala Pro Pro Arg Asp Phe Ala
545                 550                 555                 560
Ala Tyr Arg Ser Gly Gly Arg Val Lys Phe Ser Arg Ser Ala Asp
            565                 570                 575
Ala Pro Ala Tyr Gln Gln Gly Gln Asn Gln Leu Tyr Asn Glu Leu Asn
            580                 585                 590
Leu Gly Arg Arg Glu Glu Tyr Asp Val Leu Asp Lys Arg Arg Gly Arg
            595                 600                 605
Asp Pro Glu Met Gly Gly Lys Pro Arg Arg Lys Asn Pro Gln Glu Gly
            610                 615                 620
Leu Tyr Asn Glu Leu Gln Lys Asp Lys Met Ala Glu Ala Tyr Ser Glu
625                 630                 635                 640
Ile Gly Met Lys Gly Glu Arg Arg Arg Gly Lys Gly His Asp Gly Leu
            645                 650                 655
Tyr Gln Gly Leu Ser Thr Ala Thr Lys Asp Thr Tyr Asp Ala Leu His
            660                 665                 670
Met Gln Ala Leu Pro Pro Arg Leu Glu Gly Gly Gly Glu Gly Arg Gly
            675                 680                 685
Ser Leu Leu Thr Cys Gly Asp Val Glu Glu Asn Pro Gly Pro Arg Met
            690                 695                 700
Leu Leu Leu Val Thr Ser Leu Leu Leu Cys Glu Leu Pro His Pro Ala
705                 710                 715                 720
Phe Leu Leu Ile Pro Arg Lys Val Cys Asn Gly Ile Gly Ile Gly Glu
            725                 730                 735
Phe Lys Asp Ser Leu Ser Ile Asn Ala Thr Asn Ile Lys His Phe Lys
            740                 745                 750
Asn Cys Thr Ser Ile Ser Gly Asp Leu His Ile Leu Pro Val Ala Phe
            755                 760                 765
Arg Gly Asp Ser Phe Thr His Thr Pro Pro Leu Asp Pro Gln Glu Leu
            770                 775                 780
Asp Ile Leu Lys Thr Val Lys Glu Ile Thr Gly Phe Leu Leu Ile Gln
785                 790                 795                 800
Ala Trp Pro Glu Asn Arg Thr Asp Leu His Ala Phe Glu Asn Leu Glu
            805                 810                 815
Ile Ile Arg Gly Arg Thr Lys Gln His Gly Gln Phe Ser Leu Ala Val
            820                 825                 830
Val Ser Leu Asn Ile Thr Ser Leu Gly Leu Arg Ser Leu Lys Glu Ile
            835                 840                 845
Ser Asp Gly Asp Val Ile Ile Ser Gly Asn Lys Asn Leu Cys Tyr Ala
            850                 855                 860
Asn Thr Ile Asn Trp Lys Lys Leu Phe Gly Thr Ser Gly Gln Lys Thr
865                 870                 875                 880
Lys Ile Ile Ser Asn Arg Gly Glu Asn Ser Cys Lys Ala Thr Gly Gln
            885                 890                 895
```

Val Cys His Ala Leu Cys Ser Pro Glu Gly Cys Trp Gly Pro Glu Pro
                900                 905                 910

Arg Asp Cys Val Ser Cys Arg Asn Val Ser Arg Gly Arg Glu Cys Val
            915                 920                 925

Asp Lys Cys Asn Leu Leu Glu Gly Glu Pro Arg Glu Phe Val Glu Asn
        930                 935                 940

Ser Glu Cys Ile Gln Cys His Pro Glu Cys Leu Pro Gln Ala Met Asn
945                 950                 955                 960

Ile Thr Cys Thr Gly Arg Gly Pro Asp Asn Cys Ile Gln Cys Ala His
                965                 970                 975

Tyr Ile Asp Gly Pro His Cys Val Lys Thr Cys Pro Ala Gly Val Met
            980                 985                 990

Gly Glu Asn Asn Thr Leu Val Trp Lys Tyr Ala Asp Ala Gly His Val
        995                 1000                1005

Cys His Leu Cys His Pro Asn Cys Thr Tyr Gly Cys Thr Gly Pro
    1010                1015                1020

Gly Leu Glu Gly Cys Pro Thr Asn Gly Pro Lys Ile Pro Ser Ile
    1025                1030                1035

Ala Thr Gly Met Val Gly Ala Leu Leu Leu Leu Leu Val Val Ala
    1040                1045                1050

Leu Gly Ile Gly Leu Phe Met
    1055                1060

<210> SEQ ID NO 39
<211> LENGTH: 679
<212> TYPE: PRT
<213> ORGANISM: Artificial Sequence
<220> FEATURE:
<223> OTHER INFORMATION: CS1scFv-IgG4(L235E, N297Q)-CD28tm-CD28gg-Zeta

<400> SEQUENCE: 39

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Asp Phe Ser Arg Tyr Trp Met Ser Trp Val Arg Gln Ala Pro Gly
    50                  55                  60

Lys Gly Leu Glu Trp Ile Gly Glu Ile Asn Pro Asp Ser Ser Thr Ile
65                  70                  75                  80

Asn Tyr Ala Pro Ser Leu Lys Asp Lys Phe Ile Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Pro Asp Gly Asn Tyr Trp Tyr Phe
        115                 120                 125

Asp Val Trp Gly Gln Gly Thr Leu Val Thr Val Ser Gly Ser Thr
    130                 135                 140

Ser Gly Gly Gly Ser Gly Gly Gly Ser Gly Gly Gly Ser Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ala Ser Gln Asp Val Gly Ile Ala Val
            180                 185                 190

-continued

```
Ala Trp Tyr Gln Gln Lys Pro Gly Lys Val Pro Lys Leu Leu Ile Tyr
            195                 200                 205
Trp Ala Ser Thr Arg His Thr Gly Val Pro Asp Arg Phe Ser Gly Ser
210                 215                 220
Gly Ser Gly Thr Asp Phe Thr Leu Thr Ile Ser Ser Leu Gln Pro Glu
225                 230                 235                 240
Asp Val Ala Thr Tyr Tyr Cys Gln Gln Tyr Ser Ser Tyr Pro Tyr Thr
                245                 250                 255
Phe Gly Gln Gly Thr Lys Val Glu Ile Lys Glu Ser Lys Tyr Gly Pro
            260                 265                 270
Pro Cys Pro Pro Cys Pro Ala Pro Glu Phe Glu Gly Gly Pro Ser Val
            275                 280                 285
Phe Leu Phe Pro Pro Lys Pro Lys Asp Thr Leu Met Ile Ser Arg Thr
290                 295                 300
Pro Glu Val Thr Cys Val Val Val Asp Val Ser Gln Glu Asp Pro Glu
305                 310                 315                 320
Val Gln Phe Asn Trp Tyr Val Asp Gly Val Glu Val His Asn Ala Lys
                325                 330                 335
Thr Lys Pro Arg Glu Glu Gln Phe Gln Ser Thr Tyr Arg Val Val Ser
            340                 345                 350
Val Leu Thr Val Leu His Gln Asp Trp Leu Asn Gly Lys Glu Tyr Lys
            355                 360                 365
Cys Lys Val Ser Asn Lys Gly Leu Pro Ser Ser Ile Glu Lys Thr Ile
            370                 375                 380
Ser Lys Ala Lys Gly Gln Pro Arg Glu Pro Gln Val Tyr Thr Leu Pro
385                 390                 395                 400
Pro Ser Gln Glu Glu Met Thr Lys Asn Gln Val Ser Leu Thr Cys Leu
                405                 410                 415
Val Lys Gly Phe Tyr Pro Ser Asp Ile Ala Val Glu Trp Glu Ser Asn
            420                 425                 430
Gly Gln Pro Glu Asn Asn Tyr Lys Thr Thr Pro Pro Val Leu Asp Ser
            435                 440                 445
Asp Gly Ser Phe Phe Leu Tyr Ser Arg Leu Thr Val Asp Lys Ser Arg
450                 455                 460
Trp Gln Glu Gly Asn Val Phe Ser Cys Ser Val Met His Glu Ala Leu
465                 470                 475                 480
His Asn His Tyr Thr Gln Lys Ser Leu Ser Leu Ser Leu Gly Lys Met
                485                 490                 495
Phe Trp Val Leu Val Val Val Gly Gly Val Leu Ala Cys Tyr Ser Leu
            500                 505                 510
Leu Val Thr Val Ala Phe Ile Ile Phe Trp Val Arg Ser Lys Arg Ser
            515                 520                 525
Arg Gly Gly His Ser Asp Tyr Met Asn Met Thr Pro Arg Arg Pro Gly
            530                 535                 540
Pro Thr Arg Lys His Tyr Gln Pro Tyr Ala Pro Pro Arg Asp Phe Ala
545                 550                 555                 560
Ala Tyr Arg Ser Gly Gly Gly Arg Val Lys Phe Ser Arg Ser Ala Asp
                565                 570                 575
Ala Pro Ala Tyr Gln Gln Gly Gln Asn Gln Leu Tyr Asn Glu Leu Asn
            580                 585                 590
Leu Gly Arg Arg Glu Glu Tyr Asp Val Leu Asp Lys Arg Arg Gly Arg
            595                 600                 605
Asp Pro Glu Met Gly Gly Lys Pro Arg Arg Lys Asn Pro Gln Glu Gly
```

```
           610                 615                 620

Leu Tyr Asn Glu Leu Gln Lys Asp Lys Met Ala Glu Ala Tyr Ser Glu
625                 630                 635                 640

Ile Gly Met Lys Gly Glu Arg Arg Arg Gly Lys Gly His Asp Gly Leu
                645                 650                 655

Tyr Gln Gly Leu Ser Thr Ala Thr Lys Asp Thr Tyr Asp Ala Leu His
                660                 665                 670

Met Gln Ala Leu Pro Pro Arg
        675

<210> SEQ ID NO 40
<211> LENGTH: 657
<212> TYPE: PRT
<213> ORGANISM: Artificial Sequence
<220> FEATURE:
<223> OTHER INFORMATION: CS1scFv-IgG4(L235E, N297Q)-CD28tm-CD28gg-Zeta
      excluding GMCSFRa signal

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
                20                  25                  30

Trp Met Ser Trp Val Arg Gln Ala Pro Gly Lys Gly Leu Glu Trp Ile
            35                  40                  45

Gly Glu Ile Asn Pro Asp Ser Ser Thr Ile Asn Tyr Ala Pro Ser Leu
        50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
                100                 105                 110

Thr Leu Val Thr Val Ser Ser Gly Ser Thr Ser Gly Gly Gly Ser Gly
            115                 120                 125

Gly Gly Ser Gly Gly Gly Ser Ser Asp Ile Gln Met Thr Gln Ser
        130                 135                 140

Pro Ser Ser Leu Ser Ala Ser Val Gly Asp Arg Val Thr Ile Thr Cys
145                 150                 155                 160

Lys Ala Ser Gln Asp Val Gly Ile Ala Val Ala Trp Tyr Gln Gln Lys
                165                 170                 175

Pro Gly Lys Val Pro Lys Leu Leu Ile Tyr Trp Ala Ser Thr Arg His
                180                 185                 190

Thr Gly Val Pro Asp Arg Phe Ser Gly Ser Gly Ser Gly Thr Asp Phe
            195                 200                 205

Thr Leu Thr Ile Ser Ser Leu Gln Pro Glu Asp Val Ala Thr Tyr Tyr
        210                 215                 220

Cys Gln Gln Tyr Ser Ser Tyr Pro Tyr Thr Phe Gly Gln Gly Thr Lys
225                 230                 235                 240

Val Glu Ile Lys Glu Ser Lys Tyr Gly Pro Pro Cys Pro Pro Cys Pro
                245                 250                 255

Ala Pro Glu Phe Glu Gly Gly Pro Ser Val Phe Leu Phe Pro Pro Lys
                260                 265                 270

Pro Lys Asp Thr Leu Met Ile Ser Arg Thr Pro Glu Val Thr Cys Val
            275                 280                 285
```

```
Val Val Asp Val Ser Gln Glu Asp Pro Glu Val Gln Phe Asn Trp Tyr
290                 295                 300

Val Asp Gly Val Glu Val His Asn Ala Lys Thr Lys Pro Arg Glu Glu
305                 310                 315                 320

Gln Phe Gln Ser Thr Tyr Arg Val Val Ser Val Leu Thr Val Leu His
            325                 330                 335

Gln Asp Trp Leu Asn Gly Lys Glu Tyr Lys Cys Lys Val Ser Asn Lys
        340                 345                 350

Gly Leu Pro Ser Ser Ile Glu Thr Ile Ser Lys Ala Lys Gly Gln
    355                 360                 365

Pro Arg Glu Pro Gln Val Tyr Thr Leu Pro Pro Ser Gln Glu Glu Met
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Arg Leu Thr Val Asp Lys Ser Arg Trp Gln Glu Gly Asn Val
        435                 440                 445

Phe Ser Cys Ser Val Met His Glu Ala Leu His Asn His Tyr Thr Gln
450                 455                 460

Lys Ser Leu Ser Leu Ser Leu Gly Lys Met Phe Trp Val Leu Val Val
465                 470                 475                 480

Val Gly Gly Val Leu Ala Cys Tyr Ser Leu Leu Val Thr Val Ala Phe
                485                 490                 495

Ile Ile Phe Trp Val Arg Ser Lys Arg Ser Arg Gly Gly His Ser Asp
            500                 505                 510

Tyr Met Asn Met Thr Pro Arg Arg Pro Gly Pro Thr Arg Lys His Tyr
        515                 520                 525

Gln Pro Tyr Ala Pro Pro Arg Asp Phe Ala Ala Tyr Arg Ser Gly Gly
530                 535                 540

Gly Arg Val Lys Phe Ser Arg Ser Ala Asp Ala Pro Ala Tyr Gln Gln
545                 550                 555                 560

Gly Gln Asn Gln Leu Tyr Asn Glu Leu Asn Leu Gly Arg Arg Glu Glu
                565                 570                 575

Tyr Asp Val Leu Asp Lys Arg Arg Gly Arg Asp Pro Glu Met Gly Gly
            580                 585                 590

Lys Pro Arg Arg Lys Asn Pro Gln Glu Gly Leu Tyr Asn Glu Leu Gln
        595                 600                 605

Lys Asp Lys Met Ala Glu Ala Tyr Ser Glu Ile Gly Met Lys Gly Glu
610                 615                 620

Arg Arg Arg Gly Lys Gly His Asp Gly Leu Tyr Gln Gly Leu Ser Thr
625                 630                 635                 640

Ala Thr Lys Asp Thr Tyr Asp Ala Leu His Met Gln Ala Leu Pro Pro
                645                 650                 655

Arg

<210> SEQ ID NO 41
<211> LENGTH: 836
<212> TYPE: PRT
<213> ORGANISM: Artificial Sequence
<220> FEATURE:
<223> OTHER INFORMATION: CS1scFv-Linker-CD4tm-41BB-Zeta-T2A-EGFRt
```

```
<400> SEQUENCE: 41

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
                20                  25                  30

Leu Val Gln Pro Gly Gly Ser Leu Arg Leu Ser Cys Ala Ala Ser Gly
            35                  40                  45

Phe Asp Phe Ser Arg Tyr Trp Met Ser Trp Val Arg Gln Ala Pro Gly
        50                  55                  60

Lys Gly Leu Glu Trp Ile Gly Glu Ile Asn Pro Asp Ser Ser Thr Ile
65                  70                  75                  80

Asn Tyr Ala Pro Ser Leu Lys Asp Lys Phe Ile Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Pro Asp Gly Asn Tyr Trp Tyr Phe
        115                 120                 125

Asp Val Trp Gly Gln Gly Thr Leu Val Thr Val Ser Ser Gly Ser Thr
    130                 135                 140

Ser Gly Gly Gly Ser Gly Gly Gly Ser Gly Gly Gly Ser Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ala Ser Gln Asp Val Gly Ile Ala Val
            180                 185                 190

Ala Trp Tyr Gln Gln Lys Pro Gly Lys Val Pro Lys Leu Leu Ile Tyr
        195                 200                 205

Trp Ala Ser Thr Arg His Thr Gly Val Pro Asp Arg Phe Ser Gly Ser
    210                 215                 220

Gly Ser Gly Thr Asp Phe Thr Leu Thr Ile Ser Ser Leu Gln Pro Glu
225                 230                 235                 240

Asp Val Ala Thr Tyr Tyr Cys Gln Gln Tyr Ser Ser Tyr Pro Tyr Thr
                245                 250                 255

Phe Gly Gln Gly Thr Lys Val Glu Ile Lys Gly Gly Gly Ser Ser Gly
            260                 265                 270

Gly Gly Ser Gly Met Ala Leu Ile Val Leu Gly Gly Val Ala Gly Leu
        275                 280                 285

Leu Leu Phe Ile Gly Leu Gly Ile Phe Phe Lys Arg Gly Arg Lys Lys
    290                 295                 300

Leu Leu Tyr Ile Phe Lys Gln Pro Phe Met Arg Pro Val Gln Thr Thr
305                 310                 315                 320

Gln Glu Glu Asp Gly Cys Ser Cys Arg Phe Pro Glu Glu Glu Glu Gly
                325                 330                 335

Gly Cys Glu Leu Gly Gly Arg Val Lys Phe Ser Arg Ser Ala Asp
            340                 345                 350

Ala Pro Ala Tyr Gln Gln Gly Gln Asn Gln Leu Tyr Asn Glu Leu Asn
        355                 360                 365

Leu Gly Arg Arg Glu Glu Tyr Asp Val Leu Asp Lys Arg Arg Gly Arg
    370                 375                 380

Asp Pro Glu Met Gly Gly Lys Pro Arg Arg Lys Asn Pro Gln Glu Gly
385                 390                 395                 400

Leu Tyr Asn Glu Leu Gln Lys Asp Lys Met Ala Glu Ala Tyr Ser Glu
                405                 410                 415
```

```
Ile Gly Met Lys Gly Glu Arg Arg Gly Lys Gly His Asp Gly Leu
            420                 425                 430
Tyr Gln Gly Leu Ser Thr Ala Thr Lys Asp Thr Tyr Asp Ala Leu His
            435                 440                 445
Met Gln Ala Leu Pro Pro Arg Leu Gly Gly Glu Gly Arg Gly
            450                 455                 460
Ser Leu Leu Thr Cys Gly Asp Val Glu Glu Asn Pro Gly Pro Arg Met
465                 470                 475                 480
Leu Leu Leu Val Thr Ser Leu Leu Cys Glu Leu Pro His Pro Ala
                485                 490                 495
Phe Leu Leu Ile Pro Arg Lys Val Cys Asn Gly Ile Gly Ile Gly Glu
                500                 505                 510
Phe Lys Asp Ser Leu Ser Ile Asn Ala Thr Asn Ile Lys His Phe Lys
                515                 520                 525
Asn Cys Thr Ser Ile Ser Gly Asp Leu His Ile Leu Pro Val Ala Phe
                530                 535                 540
Arg Gly Asp Ser Phe Thr His Thr Pro Pro Leu Asp Pro Gln Glu Leu
545                 550                 555                 560
Asp Ile Leu Lys Thr Val Lys Glu Ile Thr Gly Phe Leu Leu Ile Gln
                565                 570                 575
Ala Trp Pro Glu Asn Arg Thr Asp Leu His Ala Phe Glu Asn Leu Glu
                580                 585                 590
Ile Ile Arg Gly Arg Thr Lys Gln His Gly Gln Phe Ser Leu Ala Val
                595                 600                 605
Val Ser Leu Asn Ile Thr Ser Leu Gly Leu Arg Ser Leu Lys Glu Ile
                610                 615                 620
Ser Asp Gly Asp Val Ile Ile Ser Gly Asn Lys Asn Leu Cys Tyr Ala
625                 630                 635                 640
Asn Thr Ile Asn Trp Lys Lys Leu Phe Gly Thr Ser Gly Gln Lys Thr
                645                 650                 655
Lys Ile Ile Ser Asn Arg Gly Glu Asn Ser Cys Lys Ala Thr Gly Gln
                660                 665                 670
Val Cys His Ala Leu Cys Ser Pro Glu Gly Cys Trp Gly Pro Glu Pro
                675                 680                 685
Arg Asp Cys Val Ser Cys Arg Asn Val Ser Arg Gly Arg Glu Cys Val
690                 695                 700
Asp Lys Cys Asn Leu Leu Glu Gly Glu Pro Arg Glu Phe Val Glu Asn
705                 710                 715                 720
Ser Glu Cys Ile Gln Cys His Pro Glu Cys Leu Pro Gln Ala Met Asn
                725                 730                 735
Ile Thr Cys Thr Gly Arg Gly Pro Asp Asn Cys Ile Gln Cys Ala His
                740                 745                 750
Tyr Ile Asp Gly Pro His Cys Val Lys Thr Cys Pro Ala Gly Val Met
                755                 760                 765
Gly Glu Asn Asn Thr Leu Val Trp Lys Tyr Ala Asp Ala Gly His Val
                770                 775                 780
Cys His Leu Cys His Pro Asn Cys Thr Tyr Gly Cys Thr Gly Pro Gly
785                 790                 795                 800
Leu Glu Gly Cys Pro Thr Asn Gly Pro Lys Ile Pro Ser Ile Ala Thr
                805                 810                 815
Gly Met Val Gly Ala Leu Leu Leu Leu Val Val Ala Leu Gly Ile
                820                 825                 830
```

Gly Leu Phe Met
         835

<210> SEQ ID NO 42
<211> LENGTH: 455
<212> TYPE: PRT
<213> ORGANISM: Artificial Sequence
<220> FEATURE:
<223> OTHER INFORMATION: CS1scFv-Linker-CD4tm-41BB-Zeta

<400> SEQUENCE: 42

Met Leu Leu Leu Val Thr Ser Leu Leu Cys Glu Leu Pro His Pro
1               5                   10                  15

Ala Phe Leu Leu Ile Pro Glu Val Gln Leu Val Glu Ser Gly Gly
            20                  25                  30

Leu Val Gln Pro Gly Gly Ser Leu Arg Leu Ser Cys Ala Ala Ser Gly
        35                  40                  45

Phe Asp Phe Ser Arg Tyr Trp Met Ser Trp Val Arg Gln Ala Pro Gly
    50                  55                  60

Lys Gly Leu Glu Trp Ile Gly Glu Ile Asn Pro Asp Ser Ser Thr Ile
65                  70                  75                  80

Asn Tyr Ala Pro Ser Leu Lys Asp Lys Phe Ile Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Pro Asp Gly Asn Tyr Trp Tyr Phe
        115                 120                 125

Asp Val Trp Gly Gln Gly Thr Leu Val Thr Val Ser Ser Gly Ser Thr
    130                 135                 140

Ser Gly Gly Gly Ser Gly Gly Gly Ser Gly Gly Gly Ser Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ala Ser Gln Asp Val Gly Ile Ala Val
            180                 185                 190

Ala Trp Tyr Gln Gln Lys Pro Gly Lys Val Pro Lys Leu Leu Ile Tyr
        195                 200                 205

Trp Ala Ser Thr Arg His Thr Gly Val Pro Asp Arg Phe Ser Gly Ser
    210                 215                 220

Gly Ser Gly Thr Asp Phe Thr Leu Thr Ile Ser Ser Leu Gln Pro Glu
225                 230                 235                 240

Asp Val Ala Thr Tyr Tyr Cys Gln Gln Tyr Ser Ser Tyr Pro Tyr Thr
                245                 250                 255

Phe Gly Gln Gly Thr Lys Val Glu Ile Lys Gly Gly Gly Ser Ser Gly
            260                 265                 270

Gly Gly Ser Gly Met Ala Leu Ile Val Leu Gly Gly Val Ala Gly Leu
        275                 280                 285

Leu Leu Phe Ile Gly Leu Gly Ile Phe Phe Lys Arg Gly Arg Lys Lys
    290                 295                 300

Leu Leu Tyr Ile Phe Lys Gln Pro Phe Met Arg Pro Val Gln Thr Thr
305                 310                 315                 320

Gln Glu Glu Asp Gly Cys Ser Cys Arg Phe Pro Glu Glu Glu Gly
                325                 330                 335

Gly Cys Glu Leu Gly Gly Arg Val Lys Phe Ser Arg Ser Ala Asp
            340                 345                 350

```
Ala Pro Ala Tyr Gln Gln Gly Gln Asn Gln Leu Tyr Asn Glu Leu Asn
            355                 360                 365

Leu Gly Arg Arg Glu Glu Tyr Asp Val Leu Asp Lys Arg Arg Gly Arg
        370                 375                 380

Asp Pro Glu Met Gly Gly Lys Pro Arg Arg Lys Asn Pro Gln Glu Gly
385                 390                 395                 400

Leu Tyr Asn Glu Leu Gln Lys Asp Lys Met Ala Glu Ala Tyr Ser Glu
                405                 410                 415

Ile Gly Met Lys Gly Glu Arg Arg Arg Gly Lys Gly His Asp Gly Leu
            420                 425                 430

Tyr Gln Gly Leu Ser Thr Ala Thr Lys Asp Thr Tyr Asp Ala Leu His
        435                 440                 445

Met Gln Ala Leu Pro Pro Arg
    450                 455

<210> SEQ ID NO 43
<211> LENGTH: 433
<212> TYPE: PRT
<213> ORGANISM: Artificial Sequence
<220> FEATURE:
<223> OTHER INFORMATION: CS1scFv-Linker-CD4tm-41BB-Zeta excluding
      GMCSFRa signal

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
            100                 105                 110

Thr Leu Val Thr Val Ser Ser Gly Ser Thr Ser Gly Gly Gly Ser Gly
        115                 120                 125

Gly Gly Ser Gly Gly Gly Ser Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Lys Ala Ser Gln Asp Val Gly Ile Ala Val Ala Trp Tyr Gln Gln Lys
                165                 170                 175

Pro Gly Lys Val Pro Lys Leu Leu Ile Tyr Trp Ala Ser Thr Arg His
            180                 185                 190

Thr Gly Val Pro Asp Arg Phe Ser Gly Ser Gly Ser Gly Thr Asp Phe
        195                 200                 205

Thr Leu Thr Ile Ser Ser Leu Gln Pro Glu Asp Val Ala Thr Tyr Tyr
    210                 215                 220

Cys Gln Gln Tyr Ser Ser Tyr Pro Tyr Thr Phe Gly Gln Gly Thr Lys
225                 230                 235                 240

Val Glu Ile Lys Gly Gly Gly Ser Gly Gly Gly Ser Gly Met Ala
                245                 250                 255
```

```
Leu Ile Val Leu Gly Gly Val Ala Gly Leu Leu Phe Ile Gly Leu
            260                 265                 270

Gly Ile Phe Phe Lys Arg Gly Arg Lys Lys Leu Leu Tyr Ile Phe Lys
            275                 280                 285

Gln Pro Phe Met Arg Pro Val Gln Thr Thr Gln Glu Glu Asp Gly Cys
            290                 295                 300

Ser Cys Arg Phe Pro Glu Glu Glu Glu Gly Gly Cys Glu Leu Gly Gly
305                 310                 315                 320

Gly Arg Val Lys Phe Ser Arg Ser Ala Asp Ala Pro Ala Tyr Gln Gln
                325                 330                 335

Gly Gln Asn Gln Leu Tyr Asn Glu Leu Asn Leu Gly Arg Arg Glu Glu
            340                 345                 350

Tyr Asp Val Leu Asp Lys Arg Arg Gly Arg Asp Pro Glu Met Gly Gly
            355                 360                 365

Lys Pro Arg Arg Lys Asn Pro Gln Glu Gly Leu Tyr Asn Glu Leu Gln
            370                 375                 380

Lys Asp Lys Met Ala Glu Ala Tyr Ser Glu Ile Gly Met Lys Gly Glu
385                 390                 395                 400

Arg Arg Arg Gly Lys Gly His Asp Gly Leu Tyr Gln Gly Leu Ser Thr
                405                 410                 415

Ala Thr Lys Asp Thr Tyr Asp Ala Leu His Met Gln Ala Leu Pro Pro
            420                 425                 430

Arg

<210> SEQ ID NO 44
<211> LENGTH: 841
<212> TYPE: PRT
<213> ORGANISM: Artificial Sequence
<220> FEATURE:
<223> OTHER INFORMATION: CS1scFv-Linker-CD28tm-CD28gg-Zeta-T2A-EGFRt

<400> SEQUENCE: 44

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Asp Phe Ser Arg Tyr Trp Met Ser Trp Val Arg Gln Ala Pro Gly
    50                  55                  60

Lys Gly Leu Glu Trp Ile Gly Glu Ile Asn Pro Asp Ser Ser Thr Ile
65                  70                  75                  80

Asn Tyr Ala Pro Ser Leu Lys Asp Lys Phe Ile Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Pro Asp Gly Asn Tyr Trp Tyr Phe
            115                 120                 125

Asp Val Trp Gly Gln Gly Thr Leu Val Thr Val Ser Ser Gly Ser Thr
    130                 135                 140

Ser Gly Gly Gly Ser Gly Gly Gly Ser Gly Gly Gly Ser Ser Asp
145                 150                 155                 160

Ile Gln Met Thr Gln Ser Pro Ser Ser Leu Ser Ala Ser Val Gly Asp
                165                 170                 175
```

```
Arg Val Thr Ile Thr Cys Lys Ala Ser Gln Asp Val Gly Ile Ala Val
                180                 185                 190

Ala Trp Tyr Gln Gln Lys Pro Gly Lys Val Pro Lys Leu Leu Ile Tyr
        195                 200                 205

Trp Ala Ser Thr Arg His Thr Gly Val Pro Asp Arg Phe Ser Gly Ser
        210                 215                 220

Gly Ser Gly Thr Asp Phe Thr Leu Thr Ile Ser Ser Leu Gln Pro Glu
225                 230                 235                 240

Asp Val Ala Thr Tyr Tyr Cys Gln Gln Tyr Ser Ser Tyr Pro Tyr Thr
                245                 250                 255

Phe Gly Gln Gly Thr Lys Val Glu Ile Lys Gly Gly Ser Ser Gly
            260                 265                 270

Gly Gly Ser Gly Met Phe Trp Val Leu Val Val Val Gly Gly Val Leu
        275                 280                 285

Ala Cys Tyr Ser Leu Leu Val Thr Val Ala Phe Ile Ile Phe Trp Val
        290                 295                 300

Arg Ser Lys Arg Ser Arg Gly Gly His Ser Asp Tyr Met Asn Met Thr
305                 310                 315                 320

Pro Arg Arg Pro Gly Pro Thr Arg Lys His Tyr Gln Pro Tyr Ala Pro
                325                 330                 335

Pro Arg Asp Phe Ala Ala Tyr Arg Ser Gly Gly Gly Arg Val Lys Phe
                340                 345                 350

Ser Arg Ser Ala Asp Ala Pro Ala Tyr Gln Gln Gly Gln Asn Gln Leu
            355                 360                 365

Tyr Asn Glu Leu Asn Leu Gly Arg Arg Glu Glu Tyr Asp Val Leu Asp
370                 375                 380

Lys Arg Arg Gly Arg Asp Pro Glu Met Gly Gly Lys Pro Arg Arg Lys
385                 390                 395                 400

Asn Pro Gln Glu Gly Leu Tyr Asn Glu Leu Gln Lys Asp Lys Met Ala
                405                 410                 415

Glu Ala Tyr Ser Glu Ile Gly Met Lys Gly Glu Arg Arg Arg Gly Lys
            420                 425                 430

Gly His Asp Gly Leu Tyr Gln Gly Leu Ser Thr Ala Thr Lys Asp Thr
        435                 440                 445

Tyr Asp Ala Leu His Met Gln Ala Leu Pro Pro Arg Leu Glu Gly Gly
450                 455                 460

Gly Glu Gly Arg Gly Ser Leu Leu Thr Cys Gly Asp Val Glu Glu Asn
465                 470                 475                 480

Pro Gly Pro Arg Met Leu Leu Leu Val Thr Ser Leu Leu Leu Cys Glu
                485                 490                 495

Leu Pro His Pro Ala Phe Leu Leu Ile Pro Arg Lys Val Cys Asn Gly
            500                 505                 510

Ile Gly Ile Gly Glu Phe Lys Asp Ser Leu Ser Ile Asn Ala Thr Asn
        515                 520                 525

Ile Lys His Phe Lys Asn Cys Thr Ser Ile Ser Gly Asp Leu His Ile
        530                 535                 540

Leu Pro Val Ala Phe Arg Gly Asp Ser Phe Thr His Thr Pro Pro Leu
545                 550                 555                 560

Asp Pro Gln Glu Leu Asp Ile Leu Lys Thr Val Lys Glu Ile Thr Gly
                565                 570                 575

Phe Leu Leu Ile Gln Ala Trp Pro Glu Asn Arg Thr Asp Leu His Ala
            580                 585                 590

Phe Glu Asn Leu Glu Ile Ile Arg Gly Arg Thr Lys Gln His Gly Gln
```

```
                595                 600                 605
Phe Ser Leu Ala Val Val Ser Leu Asn Ile Thr Ser Leu Gly Leu Arg
    610                 615                 620
Ser Leu Lys Glu Ile Ser Asp Gly Asp Val Ile Ile Ser Gly Asn Lys
625                 630                 635                 640
Asn Leu Cys Tyr Ala Asn Thr Ile Asn Trp Lys Lys Leu Phe Gly Thr
                645                 650                 655
Ser Gly Gln Lys Thr Lys Ile Ile Ser Asn Arg Gly Glu Asn Ser Cys
            660                 665                 670
Lys Ala Thr Gly Gln Val Cys His Ala Leu Cys Ser Pro Glu Gly Cys
            675                 680                 685
Trp Gly Pro Glu Pro Arg Asp Cys Val Ser Cys Arg Asn Val Ser Arg
            690                 695                 700
Gly Arg Glu Cys Val Asp Lys Cys Asn Leu Leu Glu Gly Glu Pro Arg
705                 710                 715                 720
Glu Phe Val Glu Asn Ser Glu Cys Ile Gln Cys His Pro Glu Cys Leu
                725                 730                 735
Pro Gln Ala Met Asn Ile Thr Cys Thr Gly Arg Gly Pro Asp Asn Cys
            740                 745                 750
Ile Gln Cys Ala His Tyr Ile Asp Gly Pro His Cys Val Lys Thr Cys
            755                 760                 765
Pro Ala Gly Val Met Gly Glu Asn Asn Thr Leu Val Trp Lys Tyr Ala
            770                 775                 780
Asp Ala Gly His Val Cys His Leu Cys His Pro Asn Cys Thr Tyr Gly
785                 790                 795                 800
Cys Thr Gly Pro Gly Leu Glu Gly Cys Pro Thr Asn Gly Pro Lys Ile
                805                 810                 815
Pro Ser Ile Ala Thr Gly Met Val Gly Ala Leu Leu Leu Leu Leu Val
            820                 825                 830
Val Ala Leu Gly Ile Gly Leu Phe Met
            835                 840

<210> SEQ ID NO 45
<211> LENGTH: 460
<212> TYPE: PRT
<213> ORGANISM: Artificial Sequence
<220> FEATURE:
<223> OTHER INFORMATION: CS1scFv-Linker-CD28tm-CD28gg-Zeta

<400> SEQUENCE: 45

Met Leu Leu Leu Val Thr Ser Leu Leu Leu Cys Glu Leu Pro His Pro
1               5                   10                  15
Ala Phe Leu Leu Ile Pro Glu Val Gln Leu Val Glu Ser Gly Gly Gly
            20                  25                  30
Leu Val Gln Pro Gly Gly Ser Leu Arg Leu Ser Cys Ala Ala Ser Gly
        35                  40                  45
Phe Asp Phe Ser Arg Tyr Trp Met Ser Trp Val Arg Gln Ala Pro Gly
    50                  55                  60
Lys Gly Leu Glu Trp Ile Gly Glu Ile Asn Pro Asp Ser Ser Thr Ile
65                  70                  75                  80
Asn Tyr Ala Pro Ser Leu Lys Asp Lys Phe Ile Ile Ser Arg Asp Asn
                85                  90                  95
Ala Lys Asn Ser Leu Tyr Leu Gln Met Asn Ser Leu Arg Ala Glu Asp
            100                 105                 110
Thr Ala Val Tyr Tyr Cys Ala Arg Pro Asp Gly Asn Tyr Trp Tyr Phe
```

```
            115                 120                 125
Asp Val Trp Gly Gln Gly Thr Leu Val Thr Val Ser Ser Gly Ser Thr
    130                 135                 140

Ser Gly Gly Gly Ser Gly Gly Gly Ser Gly Gly Gly Ser Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ala Ser Gln Asp Val Gly Ile Ala Val
            180                 185                 190

Ala Trp Tyr Gln Gln Lys Pro Gly Lys Val Pro Lys Leu Leu Ile Tyr
        195                 200                 205

Trp Ala Ser Thr Arg His Thr Gly Val Pro Asp Arg Phe Ser Gly Ser
    210                 215                 220

Gly Ser Gly Thr Asp Phe Thr Leu Thr Ile Ser Ser Leu Gln Pro Glu
225                 230                 235                 240

Asp Val Ala Thr Tyr Tyr Cys Gln Gln Tyr Ser Ser Tyr Pro Tyr Thr
                245                 250                 255

Phe Gly Gln Gly Thr Lys Val Glu Ile Lys Gly Gly Gly Ser Ser Gly
            260                 265                 270

Gly Gly Ser Gly Met Phe Trp Val Leu Val Val Val Gly Gly Val Leu
        275                 280                 285

Ala Cys Tyr Ser Leu Leu Val Thr Val Ala Phe Ile Ile Phe Trp Val
    290                 295                 300

Arg Ser Lys Arg Ser Arg Gly Gly His Ser Asp Tyr Met Asn Met Thr
305                 310                 315                 320

Pro Arg Arg Pro Gly Pro Thr Arg Lys His Tyr Gln Pro Tyr Ala Pro
                325                 330                 335

Pro Arg Asp Phe Ala Ala Tyr Arg Ser Gly Gly Arg Val Lys Phe
            340                 345                 350

Ser Arg Ser Ala Asp Ala Pro Ala Tyr Gln Gln Gly Gln Asn Gln Leu
        355                 360                 365

Tyr Asn Glu Leu Asn Leu Gly Arg Arg Glu Glu Tyr Asp Val Leu Asp
    370                 375                 380

Lys Arg Arg Gly Arg Asp Pro Glu Met Gly Gly Lys Pro Arg Arg Lys
385                 390                 395                 400

Asn Pro Gln Glu Gly Leu Tyr Asn Glu Leu Gln Lys Asp Lys Met Ala
                405                 410                 415

Glu Ala Tyr Ser Glu Ile Gly Met Lys Gly Glu Arg Arg Arg Gly Lys
            420                 425                 430

Gly His Asp Gly Leu Tyr Gln Gly Leu Ser Thr Ala Thr Lys Asp Thr
        435                 440                 445

Tyr Asp Ala Leu His Met Gln Ala Leu Pro Pro Arg
    450                 455                 460

<210> SEQ ID NO 46
<211> LENGTH: 438
<212> TYPE: PRT
<213> ORGANISM: Artificial Sequence
<220> FEATURE:
<223> OTHER INFORMATION: CS1scFv-Linker-CD28tm-CD28gg-Zeta excluding
      GMCSFRa signal

<400> SEQUENCE: 46

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Asp Phe Ser Arg Tyr
             20                  25                  30
Trp Met Ser Trp Val Arg Gln Ala Pro Gly Lys Gly Leu Glu Trp Ile
         35                  40                  45
Gly Glu Ile Asn Pro Asp Ser Ser Thr Ile Asn Tyr Ala Pro Ser Leu
     50                  55                  60
Lys Asp Lys Phe Ile Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Pro Asp Gly Asn Tyr Trp Tyr Phe Asp Val Trp Gly Gln Gly
             100                 105                 110
Thr Leu Val Thr Val Ser Ser Gly Ser Thr Ser Gly Gly Gly Ser Gly
         115                 120                 125
Gly Gly Ser Gly Gly Gly Ser Ser Asp Ile Gln Met Thr Gln Ser
     130                 135                 140
Pro Ser Ser Leu Ser Ala Ser Val Gly Asp Arg Val Thr Ile Thr Cys
145                 150                 155                 160
Lys Ala Ser Gln Asp Val Gly Ile Ala Val Ala Trp Tyr Gln Gln Lys
                 165                 170                 175
Pro Gly Lys Val Pro Lys Leu Leu Ile Tyr Trp Ala Ser Thr Arg His
             180                 185                 190
Thr Gly Val Pro Asp Arg Phe Ser Gly Ser Gly Ser Gly Thr Asp Phe
         195                 200                 205
Thr Leu Thr Ile Ser Ser Leu Gln Pro Glu Asp Val Ala Thr Tyr Tyr
     210                 215                 220
Cys Gln Gln Tyr Ser Ser Tyr Pro Tyr Thr Phe Gly Gln Gly Thr Lys
225                 230                 235                 240
Val Glu Ile Lys Gly Gly Gly Ser Ser Gly Gly Ser Gly Met Phe
                 245                 250                 255
Trp Val Leu Val Val Val Gly Gly Val Leu Ala Cys Tyr Ser Leu Leu
             260                 265                 270
Val Thr Val Ala Phe Ile Ile Phe Trp Val Arg Ser Lys Arg Ser Arg
         275                 280                 285
Gly Gly His Ser Asp Tyr Met Asn Met Thr Pro Arg Arg Pro Gly Pro
     290                 295                 300
Thr Arg Lys His Tyr Gln Pro Tyr Ala Pro Pro Arg Asp Phe Ala Ala
305                 310                 315                 320
Tyr Arg Ser Gly Gly Gly Arg Val Lys Phe Ser Arg Ser Ala Asp Ala
                 325                 330                 335
Pro Ala Tyr Gln Gln Gly Gln Asn Gln Leu Tyr Asn Glu Leu Asn Leu
             340                 345                 350
Gly Arg Arg Glu Glu Tyr Asp Val Leu Asp Lys Arg Gly Arg Asp
         355                 360                 365
Pro Glu Met Gly Gly Lys Pro Arg Arg Lys Asn Pro Gln Glu Gly Leu
     370                 375                 380
Tyr Asn Glu Leu Gln Lys Asp Lys Met Ala Glu Ala Tyr Ser Glu Ile
385                 390                 395                 400
Gly Met Lys Gly Glu Arg Arg Arg Gly Lys Gly His Asp Gly Leu Tyr
                 405                 410                 415
Gln Gly Leu Ser Thr Ala Thr Lys Asp Thr Tyr Asp Ala Leu His Met
             420                 425                 430
Gln Ala Leu Pro Pro Arg
```

435

<210> SEQ ID NO 47
<211> LENGTH: 9796
<212> TYPE: DNA
<213> ORGANISM: Artificial Sequence
<220> FEATURE:
<223> OTHER INFORMATION: CS1scFv-IgG4(HL-CH3)-CD28gg-Zeta-T2A-
      EGFRt_epHIV7

<400> SEQUENCE: 47

| | |
|---|---|
| gttagaccag atctgagcct gggagctctc tggctaacta gggaacccac tgcttaagcc | 60 |
| tcaataaagc ttgccttgag tgcttcaagt agtgtgtgcc cgtctgttgt gtgactctgg | 120 |
| taactagaga tccctcagac ccttttagtc agtgtggaaa atctctagca gtggcgcccg | 180 |
| aacagggact tgaaagcgaa agggaaacca gaggagctct ctcgacgcag gactcggctt | 240 |
| gctgaagcgc gcacggcaag aggcgagggg cggcgactgg tgagtacgcc aaaaattttg | 300 |
| actagcggag gctagaagga gagagatggg tgcgagagcg tcagtattaa gcgggggaga | 360 |
| attagatcga tgggaaaaaa ttcggttaag gccagggggga agaaaaaat ataaattaaa | 420 |
| acatatagta tgggcaagca gggagctaga acgattcgca gttaatcctg gcctgttaga | 480 |
| aacatcagaa ggctgtagac aaatactggg acagctacaa ccatcccttc agacaggatc | 540 |
| agaagaactt agatcattat ataatacagt agcaaccctc tattgtgtgc atcaaaggat | 600 |
| agagataaaa gacaccaagg aagctttaga caagatagag aagagcaaaa caaaagtaa | 660 |
| gaaaaagca cagcaagcag cagctgacac aggacacagc aatcaggtca gccaaaatta | 720 |
| ccctatagtg cagaacatcc aggggcaaat ggtacatcag gccatatcac ctagaacttt | 780 |
| aaatgcatgg gtaaaagtag tagaagagaa ggctttcagc ccagaagtga tacccatgtt | 840 |
| ttcagcatta tcagaaggag ccaccccaca agatttaaac accatgctaa acacagtggg | 900 |
| gggacatcaa gcagccatgc aaatgttaaa agagaccatc aatgaggaag ctgcaggcaa | 960 |
| agagaagagt ggtgcagaga gaaaaaagag cagtgggaat aggagctttg ttccttgggt | 1020 |
| tcttgggagc agcaggaagc actatgggcg cagcgtcaat gacgctgacg gtacaggcca | 1080 |
| gacaattatt gtctggtata gtgcagcagc agaacaattt gctgagggct attgaggcgc | 1140 |
| aacagcatct gttgcaactc acagtctggg gcatcaagca gctccaggca agaatcctgg | 1200 |
| ctgtggaaag atacctaaag gatcaacagc tcctggggat ttggggttgc tctggaaaac | 1260 |
| tcatttgcac cactgctgtg ccttggatct acaaatggca gtattcatcc acaattttaa | 1320 |
| aagaaaaggg gggattgggg ggtacagtgc aggggaaaga atagtagaca taatagcaac | 1380 |
| agacatacaa actaaagaat tacaaaaaca aattacaaaa attcaaaatt ttcgggttta | 1440 |
| ttacagggac agcagagatc cagtttgggg atcaattgca tgaagaatct gcttagggtt | 1500 |
| aggcgttttg cgctgcttcg cgaggatctg cgatcgctcc ggtgcccgtc agtgggcaga | 1560 |
| gcgcacatcg cccacagtcc ccgagaagtt ggggggaggg gtcggcaatt gaaccggtgc | 1620 |
| ctagagaagg tggcgcgggg taaactggga aagtgatgtc gtgtactggc tccgcctttt | 1680 |
| tcccgagggt gggggagaac cgtatataag tgcagtagtc gccgtgaacg ttctttttcg | 1740 |
| caacgggttt gccgccagaa cacagctgaa gcttcgaggg gctcgcatct ctccttcacg | 1800 |
| cgcccgccgc cctacctgag gccgccatcc acgccggttg agtcgcgttc tgccgcctcc | 1860 |
| cgcctgtggt gcctcctgaa ctgcgtccgc cgtctaggta agtttaaagc tcaggtcgag | 1920 |
| accgggcctt tgtccggcgc tcccttggag cctacctaga ctcagccggc tctccacgct | 1980 |

```
ttgcctgacc ctgcttgctc aactctacgt ctttgtttcg ttttctgttc tgcgccgtta    2040
cagatccaag ctgtgaccgg cgcctacggc tagcgccgcc accatgctgc tgctcgtgac    2100
atctctgctg ctgtgcgagc tgccccaccc cgcctttctg ctgattcctg aggtgcagct    2160
ggtggaaagc ggcggaggac tggtgcagcc tggcggatct ctgagactga gctgtgccgc    2220
cagcggcttc gacttcagcc ggtactggat gagctgggtg cgccaggccc ctggcaaagg    2280
cctggaatgg atcggcgaga tcaaccccga cagcagcacc atcaactacg cccccagcct    2340
gaaggacaag ttcatcatca gccgggacaa cgccaagaac agcctgtacc tgcagatgaa    2400
ctccctgcgg gccgaggaca ccgccgtgta ctattgcgcc agacccgacg gcaactactg    2460
gtacttcgac gtgtggggcc agggcaccct cgtgacagtg tctagcggca gcacaagcgg    2520
aggcggatct ggcggaggat caggcggggg aggatccagc gatatccaga tgacccagag    2580
ccccagcagc ctgtctgcca cgtgggcga cagagtgacc atcacatgca aggccagcca    2640
ggacgtggga atcgccgtgg cctggtatca gcagaaaccc ggcaaggtgc ccaagctgct    2700
gatctactgg gccagcacca gacacaccgg cgtgcccgat agattttccg gcagcggctc    2760
cggcaccgac ttcaccctga caatcagctc cctgcagcct gaggacgtgg ccacctacta    2820
ctgccagcag tacagcagct acccctacac cttcggacag ggcaccaagg tggaaatcaa    2880
agagtctaag tacggccctc cctgcccccc ttgtccaggc ggcggatctt ccggaggagg    2940
aagcggaggc cagcccagag aacctcaggt gtacacactg cccccctagcc aggaagagat    3000 gaccaagaat caggtgtccc tgacatgcct cgtgaagggc ttctacccct ccgatatcgc    3060
cgtggaatgg gagagcaacg gccagcctga gaacaactac aagaccaccc cccctgtgct    3120
ggacagcgac ggctcattct tcctgtacag caggctgacc gtggacaaga gccggtggca    3180
ggaaggcaac gtgttcagct gctccgtgat gcacgaggcc ctgcacaacc actacaccca    3240
gaagtccctg agcctgtccc tgggcaagat gttctgggtg ctggtggtcg tgggcggcgt    3300 gctgcctgt tatagcctgc tcgtgaccgt ggccttcatc atctttttggg tgcgcagcaa    3360 gcggagcaga ggcggccaca cgcgactacat gaacatgacc cccagacggc caggccccac    3420
ccggaaacac tatcagcctt acgccctcc cagagacttc gccgcttatc ggtccggcgg    3480
agggcgggtg aagttcagca gaagcgccga cgcccctgcc taccagcagg gccagaatca    3540
gctgtacaac gagctgaacc tgggcagaag ggaagagtac gacgtcctgg ataagcggag    3600
aggccgggac cctgagatgg gcggcaagcc tcggcggaag aaccccccagg aaggcctgta    3660 taacgaactg cagaaagaca agatggccga ggcctacagc gagatcggca tgaagggcga    3720
gcggaggcgg ggcaagggcc acgacggcct gtatcagggc ctgtccaccg ccaccaagga    3780
tacctacgac gccctgcaca tgcaggccct gccccaagg ctcgagggcg gcggagaggg    3840
cagaggaagt cttctaacat gcggtgacgt ggaggagaat cccggcccta ggatgcttct    3900
cctggtgaca agccttctgc tctgtgagtt accacaccca gcattcctcc tgatcccacg    3960
caaagtgtgt aacggaatag gtattggtga atttaaagac tcactctcca taaatgctac    4020
gaatattaaa cacttcaaaa actgcacctc catcagtggc gatctccaca tcctgccggt    4080
ggcatttagg ggtgactcct tcacacatac tcctcctctg gatccacagg aactggatat    4140
tctgaaaacc gtaaaggaaa tcacagggtt tttgctgatt caggcttggc ctgaaaacag    4200
agacttttgg cattccttt agtgtcccaa aaacgactaa gtccgaaccg acttttgtc    4260 gacgacctc catgcctttg agaacctaga aatcatacgc ggcaggacca agcaacatgg    4320
tcagttttct cttgcagtcg tcagcctgaa cataacatcc ttgggattac gctccctcaa    4380
```

```
ggagataagt gatggagatg tgataatttc aggaaacaaa aatttgtgct atgcaaatac   4440
aataaactgg aaaaaactgt ttgggacctc cggtcagaaa accaaaatta taagcaacag   4500
aggtgaaaac agctgcaagg ccacaggcca ggtctgccat gccttgtgct cccccgaggg   4560 ctgctgggc ccggagccca gggactgcgt ctcttgccgg aatgtcagcc gaggcaggga    4620
atgcgtggac aagtgcaacc ttctggaggg tgagccaagg gagtttgtgg agaactctga   4680
gtgcatacag tgccacccag agtgcctgcc tcaggccatg aacatcacct gcacaggacg   4740
gggaccagac aactgtatcc agtgtgccca ctacattgac ggcccccact gcgtcaagac   4800
ctgcccggca ggagtcatgg gagaaaacaa caccctggtc tggaagtacg cagacgccgg   4860
ccatgtgtgc cacctgtgcc atccaaactg cacctacgga tgcactgggc caggtcttga   4920
aggctgtcca acgaatgggc ctaagatccc gtccatcgcc actgggatgg tgggggccct   4980
cctcttgctg ctggtggtgg ccctggggat cggcctcttc atgtgagcgg ccgctctaga   5040
cccgggctgc aggaattcga tatcaagctt atcgataatc aacctctgga ttacaaaatt   5100
tgtgaaagat tgactggtat tcttaactat gttgctcctt ttacgctatg tggatacgct   5160
gctttaatgc ctttgtatca tgctattgct tcccgtatgg ctttcatttt ctcctccttg   5220
tataaatcct ggttgctgtc tctttatgag gagttgtggc ccgttgtcag gcaacgtggc   5280
gtggtgtgca ctgtgtttgc tgacgcaacc cccactggtt ggggcattgc caccacctgt   5340
cagctccttt ccgggacttt cgctttcccc ctccctattg ccacggcgga actcatcgcc   5400
gcctgccttg cccgctgctg gacagggggct cggctgttgg gcactgacaa ttccgtggtg   5460
ttgtcgggga atcatcgtc ctttccttgg ctgctcgcct gtgttgccac ctggattctg   5520
cgcgggacgt ccttctgcta cgtcccttcg gccctcaatc cagcggacct tccttcccgc   5580
ggcctgctgc cggctctgcg gcctcttccg cgtcttcgcc ttcgccctca gacgagtcgg   5640
atctcccttt gggccgcctc cccgcatcga taccgtcgac tagccgtacc tttaagacca   5700
atgacttaca aggcagctgt agatcttagc cactttttaa agaaaaggg gggactggaa   5760 gggctaattc actcccaaag aagacaagat ctgcttttg cctgtactgg gtctctctgg   5820
ttagaccaga tctgagcctg ggagctctct ggctaactag ggaacccact gcttaagcct   5880
caataaagct tgccttgagt gcttcaagta gtgtgtgccc gtctgttgtg tgactctggt   5940
aactagagat ccctcagacc cttttagtca gtgtggaaaa tctctagcag aattcgatat   6000
caagcttatc gataccgtcg acctcgaggg ggggcccggt acccaattcg ccctatagtg   6060
agtcgtatta caattcactg gccgtcgttt tacaacgtcg tgactgggaa aaccctggcg   6120
ttacccaact taatcgcctt gcagcacatc cccctttcgc cagctggcgt aatagcgaag   6180
aggcccgcac cgatcgccct tcccaacagt tgcgcagcct gaatggcgaa tggaaattgt   6240
aagcgttaat attttgttaa aattcgcgtt aaattttgt taaatcagct catttttaa    6300 ccaataggcc gaaatcggca aaatccctta taaatcaaaa gaatagaccg agatagggtt   6360
gagtgttgtt ccagtttgga acaagagtcc actattaaag aacgtggact ccaacgtcaa   6420
agggcgaaaa accgtctatc agggcgatgg cccactacgt gaaccatcac cctaatcaag   6480
ttttttgggg tcgaggtgcc gtaaagcact aaatcggaac cctaaaggga gcccccgatt   6540
tagagcttga cggggaaagc cggcgaacgt ggcgagaaag gaagggaaga aagcgaaagg   6600
agcgggcgct agggcgctgg caagtgtagc ggtcacgctg cgcgtaacca ccacacccgc   6660
cgcgcttaat gcgccgctac agggcgcgtc aggtggcact tttcggggaa atgtgcgcgg   6720
```

```
aacccctatt tgtttatttt tctaaataca ttcaaatatg tatccgctca tgagacaata    6780
accctgataa atgcttcaat aatattgaaa aggaagagt atgagtattc aacatttccg     6840
tgtcgccctt attccttttt tgcggcatt ttgccttcct gttttgctc acccagaaac     6900 gctggtgaaa gtaaaagatg ctgaagatca gttgggtgca cgagtgggtt acatcgaact   6960
ggatctcaac agcggtaaga tccttgagag ttttcgcccc gaagaacgtt ttccaatgat   7020
gagcactttt aaagttctgc tatgtggcgc ggtattatcc cgtattgacg ccgggcaaga   7080
gcaactcggt cgccgcatac actattctca gaatgacttg gttgagtact caccagtcac   7140
agaaaagcat cttacggatg gcatgacagt aagagaatta tgcagtgctg ccataaccat   7200
gagtgataac actgcggcca acttacttct gacaacgatc ggaggaccga aggagctaac   7260
cgcttttttg cacaacatgg gggatcatgt aactcgcctt gatcgttggg aaccggagct   7320
gaatgaagcc ataccaaacg acgagcgtga caccacgatg cctgtagcaa tggcaacaac   7380
gttgcgcaaa ctattaactg gcgaactact tactctagct tcccggcaac aattaataga   7440
ctggatggag gcggataaag ttgcaggacc acttctgcgc tcggcccttc cggctggctg   7500
gtttattgct gataaatctg gagccggtga gcgtgggtct cgcggtatca ttgcagcact   7560
ggggccagat ggtaagccct cccgtatcgt agttatctac acgacgggga gtcaggcaac   7620
tatggatgaa cgaaatagac agatcgctga gataggtgcc tcactgatta agcattggta   7680
actgtcagac caagtttact catatatact ttagattgat ttaaaacttc atttttaatt   7740
taaaaggatc taggtgaaga tcctttttga atctcatg accaaaatcc cttaacgtga    7800
gttttcgttc cactgagcgt cagaccccgt agaaaagatc aaaggatctt cttgagatcc   7860 ttttttttctg cgcgtaatct gctgcttgca acaaaaaaa ccaccgctac cagcggtggt   7920
ttgtttgccg gatcaagagc taccaactct ttttccgaag gtaactggct tcagcagagc   7980
gcagatacca atactgttc ttctagtgta gccgtagtta ggccaccact tcaagaactc    8040
tgtagcaccg cctacatacc tcgctctgct aatcctgtta ccagtggctg ctgccagtgg   8100
cgataagtcg tgtcttaccg ggttggactc aagacgatag ttaccggata aggcgcagcg   8160
gtcgggctga acggggggtt cgtgcacaca gcccagcttg gagcgaacga cctacaccga   8220
actgagatac ctacagcgtg agctatgaga aagcgccacg cttcccgaag ggagaaaggc   8280
ggacaggtat ccggtaagcg gcagggtcgg aacaggagag cgcacgaggg agcttccagg   8340
gggaaacgcc tggtatcttt atagtcctgt cgggtttcgc cacctctgac ttgagcgtcg   8400
atttttgtga tgctcgtcag gggggcggag cctatggaaa aacgccagca acgcggcctt   8460
tttacggttc ctggccttt gctggccttt tgctcacatg ttctttcctg cgttatcccc     8520
tgattctgtg gataaccgta ttaccgcctt tgagtgagct gataccgctc gccgcagccg   8580
aacgaccgag cgcagcgagt cagtgagcga ggaagcggaa gagcgcccaa tacgcaaacc   8640
gcctctcccc gcgcgttggc cgattcatta atgcagctgg cacgacaggt ttcccgactg   8700
gaaagcgggc agtgagcgca acgcaattaa tgtgagttag ctcactcatt aggcacccca   8760
ggctttacac tttatgcttc cggctcgtat gttgtgtgga attgtgagcg ataacaatt    8820 tcacacagga aacagctatg accatgatta cgccaagctc gaaattaacc ctcactaaag   8880
ggaacaaaag ctggagctcc accgcggtgg cggcctcgag gtcgagatcc ggtcgaccag   8940
caaccatagt cccgccccta actccgccca tccgcccct aactccgccc agttccgccc    9000 attccgcc ccatggctga ctaatttttt ttatttatgc agaggccgag gccgcctcgg     9060
cctctgagct attccagaag tagtgaggag gcttttttgg aggcctaggc ttttgcaaaa   9120
```

```
agcttcgacg gtatcgattg gctcatgtcc aacattaccg ccatgttgac attgattatt    9180
gactagttat taatagtaat caattacggg gtcattagtt catagcccat atatggagtt    9240
ccgcgttaca taacttacgg taaatggccc gcctggctga ccgcccaacg acccccgccc    9300
attgacgtca ataatgacgt atgttcccat agtaacgcca atagggactt tccattgacg    9360
tcaatgggtg gagtatttac ggtaaactgc ccacttggca gtacatcaag tgtatcatat    9420
gccaagtacg cccctattg acgtcaatga cggtaaatgg cccgcctggc attatgccca     9480
gtacatgacc ttatgggact ttcctacttg gcagtacatc tacgtattag tcatcgctat    9540
taccatggtg atgcggtttt ggcagtacat caatgggcgt ggatagcggt ttgactcacg    9600
gggatttcca agtctccacc ccattgacgt caatgggagt ttgttttggc accaaaatca    9660
acgggacttt ccaaaatgtc gtaacaactc cgccccattg acgcaaatgg gcggtaggcg    9720
tgtacggaat cggagtggc gagccctcag atcctgcata taagcagctg cttttttgcct   9780
gtactgggtc tctctg                                                    9796
```

CS1 TARGETED CHIMERIC ANTIGEN RECEPTOR-MODIFIED T CELLS

CROSS-REFERENCE TO RELATED APPLICATIONS

This application is a Continuation Application of U.S. application Ser. No. 15/533,153, filed Jun. 5, 2017, now U.S. Pat. No. 10,821,161, which is a 371 National Stage Application of PCT/US2015/064303, filed Dec. 7, 2015, which claims the benefit of U.S. Non-Provisional Application No. 62/088,423, filed Dec. 5, 2014, entitled "USE OF CENTRAL MEMORY DERIVED-CS1 CHIMERIC ANTIGEN RECEPTOR-MODIFIED T CELLS TO TREAT MULTIPLE MYELOMA", the entire contents of each of which are incorporated herein by reference.

SEQUENCE LISTING

This application contains a Sequence Listing which has been submitted electronically in ASCII format and is hereby incorporated by reference in its entirety. Said ASCII copy, created on Aug. 4, 2020, is named "0006002SequenceListing.txt" and is 141,700 bytes in size.

FEDERALLY SPONSORED RESEARCH OR DEVELOPMENT

This invention was made with government support under Grant Numbers P50 CA107399 and P01 CA030206, awarded by the National Institutes of Health. The government has certain rights in the invention.

BACKGROUND

Tumor-specific T cell based immunotherapies, including therapies employing engineered T cells, have been investigated for anti-tumor treatment. In some cases the T cells used in such therapies do not remain active in vivo for a long enough period. In some cases, the antitumor activity of the T cells is relatively low. Therefore, there is a need in the art for tumor-specific cancer therapies with longer term antitumor functioning.

Adoptive T cell therapy (ACT) utilizing chimeric antigen receptor (CAR) engineered T cells may provide a safe and effective way to reduce recurrence rates of various cancers, since CAR T cells can be engineered to specifically recognize antigenically-distinct tumor populations in an WIC-independent manner.

Multiple myeloma (MM) is a B cell malignancy characterized by clonal expansion of plasma cells. MM accounts for approximately 1 percent of all cancers and slightly more than 10 percent of hematologic malignancies in the United States. In the United States alone, approximately 20,000 new cases will be diagnosed this year and over 11,000 people will die from this disease. Current therapies for MM often induce remission, but nearly all patients eventually relapse and die.

CS1 is a cell surface glycoprotein of the signaling lymphocyte activation molecule (SLAM) receptor family that is highly and selectively expressed on normal plasma cells and MM cells, with lower expression on NK cells and little or no expression on normal tissues. Elotuzumabc (HuLuc63), a humanized CS1 monoclonal antibody given together with bortezomib in patients with relapsed MM produces ≥PR in 48% of patients. The high expression of CS1 on MM cells, coupled with its restriction to plasma cells in normal tissue, makes CS1 a reasonable target for CAR T cell therapy (Hsi et al. 2008 *Clin Cancer Res* 14:2775).

SUMMARY

Described herein are CARs which comprise an extracellular domain, a transmembrane domain and an intracellular signaling domain. The extracellular domain includes a CS1-specific scFv region or a variant thereof and, optionally, a spacer, comprising, for example, a portion of human Fc domain. The extracellular domain enables the CAR, when expressed on the surface of a T cell, to direct T cell activity to cells expressing CS1, a receptor expressed on the surface of MM. The transmembrane domain includes, for example, a CD4 transmembrane domain, a CD8 transmembrane domain, a CD28 transmembrane domain, or a CD3 transmembrane domain. The intracellular signaling domain includes the signaling domain from the zeta chain of the human CD3 complex (CD3) and one or more costimulatory domains, for example, a 4-1BB costimulatory domain. The inclusion of a costimulatory domain, such as the 4-1BB (CD137) costimulatory domain in series with CD3 in the intracellular region enables the T cell to receive co-stimulatory signals. T cells, for example, patient-specific, autologous T cells can be engineered to express the CARs described herein, and the engineered cells can be expanded and used in ACT. Various T cell subsets, including both alpha beta T cells and gamma delta T cells, can be used. In addition, the CAR can be expressed in other immune cells such as NK cells. Where a patient is treated with an immune cell expressing a CAR described herein the cell can be an autologous T cell or an allogenic T cell. In some cases the cells used are a cell population that includes both CD4+ and CD8+ central memory T cells ($T_{CM}$), which are CD62L+, CCR7+, CD45RO+, and CD45RA−. The cell population can include other types of T cells as well.

The CS1 CAR described herein has certain beneficial characteristics, e.g., persistence and enhanced antitumor activity following adoptive transfer.

T cells expressing a CAR targeting CS1 can be useful in treatment of cancers such as MM, as well as other cancers that express CS1. Thus, this disclosure includes methods for treating CS1 expressing cancer using T cells expressing a CAR described herein.

Described herein is a nucleic acid molecule encoding a CAR comprising: a CS1 scFv (e.g., EVQLVESGGGLVQPGGSLRLSCAASGFDFSRYWMSWVRQAPGKGLEWIGEINP DSSTINYAPSLKDKFIISRDNAKNSLYLQMNSLRAEDTAVYYCARPDGNYWYFDVWGQGTLVTVSSGST-SGGGSGGGSGGGGSSDIQMTQSPSSL-SASVGDRVTITCK ASQDVGIA-VAWYQQKPGKVPKWYWASTRHTGVPDRFSGSGSGT DFTLTISSLQ PEDVATYYCQQYSSYPY-TFGQGTKVEIK; SEQ ID NO:1) or a variant thereof having 1-5 (e.g., 1 or 2) amino acid modifications (e.g., substitutions); a transmembrane domain selected from: a CD4 transmembrane domain or variant thereof having 1-5 (e.g., 1 or 2) amino acid modifications (e.g., substitutions), a CD8 transmembrane domain or variant thereof having 1-5 (e.g., 1 or 2) amino acid modifications (e.g., substitutions), a CD28 transmembrane domain or a variant thereof having 1-5 (e.g., 1 or 2) amino acid modifications (e.g., substitutions), and a CD3ζ transmembrane domain or a variant thereof having 1-5 (e.g., 1 or 2) amino acid modifications (e.g., substitutions); a costimulatory domain (e.g., a CD28 co-stimulatory domain or a variant thereof having 1-5 (e.g., 1 or 2) amino acid modifications (e.g., substitutions); or a 4-1BB co-stimulatory domain or a variant thereof having 1-5 (e.g., 1 or 2) amino acid modifications (e.g., substitutions); or both a CD28 co-stimulatory domain or a variant thereof having 1-5 (e.g., 1 or 2) amino acid modifications (e.g., substitutions) and a 4-1BB co-stimulatory domain or a variant thereof having 1-5 (e.g., 1 or 2) amino acid modifications (e.g., substitutions); and a CD3 signaling domain or a variant thereof having 1-5 (e.g., 1 or 2) amino acid modifications.

This disclosure also nucleic acid molecules that encode any of the CARs described herein (e.g., vectors that include a nucleic acid sequence encoding one of the CARs) and isolated T cells that express any of the CARs described herein.

Described herein is a nucleic acid molecule encoding a chimeric antigen receptor, wherein chimeric antigen receptor comprises: a CS1 scFv; a spacer region; a CD28 or CD4 transmembrane domain, a CD28 costimulatory domain or a 4-IBB costimulatory domain, an optional GlyGlyGly linker, and a CD3 ζ signaling domain.

In one embodiment, the CS1 CAR consists of or comprises the amino acid sequence of any of SEQ ID NOs:31, 34, 37, 40, 43, and 46 (mature CAR lacking a signal sequence) or the CS1 CAR consists of or comprises the amino acid sequence of any of SEQ ID NOs:30, 33, 36, 39, 42, and 45 (immature CAR having a GMCSFRa signal sequence). The CAR and can be expressed in a form that includes a signal sequence, e.g., a human GM-CSF receptor alpha signal sequence (MLLLVTSLLLCELPHPAFLLIP; SEQ ID NO:26). The CAR can be expressed with additional sequences that are useful for monitoring expression, for example a T2A skip sequence and a truncated EGFRt. Thus, the CAR can comprise or consist of the amino acid sequence of any of SEQ ID Nos: 29-46 or can comprise or consist of an amino acid sequence that is at least 95%, 96%, 97%, 98% or 99% identical to any of SEQ ID Nos: 29-46. The CAR can comprise or consist of the amino acid sequence of any of SEQ ID Nos: 29-46 with up to 1, 2, 3, 4 or 5 amino acid changes (preferably conservative amino acid changes).

Also disclosed is a population of human T cells transduced by a vector comprising an expression cassette encoding a CS1 chimeric antigen receptor described herein (e.g., a CAR that comprises or consists of the amino acid sequence of any of SEQ ID Nos: 29-46 or an amino acid sequence that is at least 95%, 96%, 97%, 98% or 99% identical to any of SEQ ID Nos: 29-46 or the amino acid sequence of any of SEQ ID Nos: 29-46 with up to 1, 2, 3, 4 or 5 amino acid changes (preferably conservative amino acid changes).

In various embodiments: the population of human T cells are central memory T cells (Tcm), e.g., CD8+/CD4+ Tcm.

An "amino acid modification" refers to an amino acid substitution, insertion, and/or deletion in a protein or peptide sequence. An "amino acid substitution" or "substitution" refers to replacement of an amino acid at a particular position in a parent peptide or protein sequence with another amino acid. A substitution can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The following are examples of various groupings of amino acids: 1) Amino acids with nonpolar R groups: Alanine, Valine, Leucine, Isoleucine, Proline, Phenylalanine, Tryptophan, Methionine; 2) Amino acids with uncharged polar R groups: Glycine, Serine, Threonine, Cysteine, Tyrosine, Asparagine, Glutamine; 3) Amino acids with charged polar R groups (negatively charged at pH 6.0): Aspartic acid, Glutamic acid; 4) Basic amino acids (positively charged at pH 6.0): Lysine, Arginine, Histidine (at pH 6.0). Another grouping may be those amino acids with phenyl groups: Phenylalanine, Tryptophan, and Tyrosine.

CS1 ScFv Domain

The CS1 ScFv domain can be any ScFv that binds CS1. In some cases the CS1 ScFv domain includes a sequence that is at least 90%, at least 95%, at least 98% identical to or identical to SEQ ID NO:1. In some cases the CS1 scFv has 1, 2, 3, 4 of 5 amino acid changes (preferably conservative) compared to SEQ ID NO:1. The ScFv can be a humanized ScFv.

Spacer Region

The CAR described herein can include a spacer region located between the CS1targeting domain (i.e., a CS1 ScFv or variant thereof) and the transmembrane domain. A variety of different spacers can be used. Some of them include at least portion of a human Fc region, for example a hinge portion of a human Fc region or a CH3 domain or variants thereof. Table 1 below provides various spacers that can be used in the CARs described herein.

TABLE 1

Examples of Spacers

| Name | Length | Sequence |
| --- | --- | --- |
| a3 | 3 aa | AAA |
| linker | 10 aa | GGGSSGGGSG (SEQ ID NO: 2) |
| IgG4 hinge (S→P) (S228P) | 12 aa | ESKYGPPCPPCP (SEQ ID NO: 3) |
| IgG4 hinge | 12 aa | ESKYGPPCPSCP (SEQ ID NO: 4) |
| IgG4 hinge (S228P) + linker | 22 aa | ESKYGPPCPPCPGGGSSGGGSG (SEQ ID NO: 5) |
| CD28 hinge | 39 aa | IEVMYPPPYLDNEKSNGTIIHVKGKHL CPSPLFPGPSKP (SEQ ID NO: 6) |
| CD8 hinge-48 aa | 48 aa | AKPTTTPAPRPPTPAPTIASQPLSLRPE ACRPAAGGAVHTRGLDFACD (SEQ ID NO: 7) |
| CD8 hinge-45 aa | 45 aa | TTTPAPRPPTPAPTIASQPLSLRPEACR PAAGGAVHTRGLDFACD (SEQ ID NO: 8) |
| IgG4 (HL-CH3) (includes S228P in hinge) | 129 aa | ESKYGPPCPPCPGGGSSGGGSGGQPR EPQVYTLPPSQEEMTKNQVSLTCLVK GFYPSDIAVEWESNGQPENNYKTTPP VLDSDGSFFLYSRLTVDKSRWQEGNV FSCSVMHEALHNHYTQKSLSLSLGK (SEQ ID NO: 9) |
| IgG4 (L235E, N297Q) | 229 aa | ESKYGPPCPSCPAPEFEGGPSVFLFPPK PKDTLMISRTPEVTCVVVDVSQEDPE VQFNWYVDGVEVHQAKTKPREEQFQ STYRVVSVLTVLHQDWLNGKEYKCK VSNKGLPSSIEKTISKAKGQPREPQVY TLPPSQEEMTKNQVSLTCLVKGFYPS DIAVEWESNGQPENNYKTTPPVLDSD GSFFLYSRLTVDKSRWQEGNVFSCSV MHEALHNHYTQKSLSLSLGK (SEQ ID NO: 10) |

TABLE 1-continued

Examples of Spacers

| Name | Length | Sequence |
|---|---|---|
| IgG4(S228P, L235E, N297Q) | 229 aa | ESKYGPPCPPCPAPEFEGGPSVFLFPPK PKDTLMISRTPEVTCVVVDVSQEDPE VQFNWYVDGVEVHQAKTKPREEQFQ STYRVVSVLTVLHQDWLNGKEYKCK VSNKGLPSSIEKTISKAKGQPREPQVY TLPPSQEEMTKNQVSLTCLVKGFYPS DIAVEWESNGQPENNYKTTPPVLDSD GSFFLYSRLTVDKSRWQEGNVFSCSV MHEALHNHYTQKSLSLSLGK (SEQ ID NO: 11) |
| IgG4(CH3) | 107 aa | GQPREPQVYTLPPSQEEMTKNQVSLT CLVKGFYPSDIAVEWESNGQPENNYK TTPPVLDSDGSFFLYSRLTVDKSRWQ EGNVFSCSVMHEALHNHYTQKSLSLS LGK (SEQ ID NO: 12) |

Some spacer regions include all or part of an immunoglobulin (e.g., IgG1, IgG2, IgG3, IgG4) hinge region, i.e., the sequence that falls between the CH1 and CH2 domains of an immunoglobulin, e.g., an IgG4 Fc hinge or a CD8 hinge. Some spacer regions include an immunoglobulin CH3 domain or both a CH3 domain and a CH2 domain. The immunoglobulin derived sequences can include one ore more amino acid modifications, for example, 1, 2, 3, 4 or 5 substitutions, e.g., substitutions that reduce off-target binding.

In certain embodiments the spacer is a hinge/linger derived from an IgG1, IgG2, IgG3, or IgG4 that includes one or more amino acid residues substituted with an amino acid residue different from that present in an unmodified hinge. The one or more substituted amino acid residues are selected from, but not limited to one or more amino acid residues at positions 220, 226, 228, 229, 230, 233, 234, 235, 234, 237, 238, 239, 243, 247, 267, 268, 280, 290, 292, 297, 298, 299, 300, 305, 309, 218, 326, 330, 331, 332, 333, 334, 336, 339, or a combination thereof.

In some embodiments, the modified hinge of the hinge/liker is derived from an IgG1, IgG2, IgG3, or IgG4 that includes, but is not limited to, one or more of the following amino acid residue substitutions: C220S, C226S, S228P, C229S, P230S, E233P, V234A, L234V, L234F, L234A, L235A, L235E, G236A, G237A, P238S, S239D, F243L, P247I, S267E, H268Q, S280H, K290S, K290E, K290N, R292P, N297A, N297Q, S298A, S298G, S298D, S298V, T299A, Y300L, V305I, V309L, E318A, K326A, K326W, K326E, L328F, A330L, A330S, A331S, P331S, I332E, E333A, E333S, E333S, K334A, A339D, A339Q, P396L, or a combination thereof.

In some embodiments, the modified hinge is derived from a human IgG4 hinge/CH2/CH3 region having the amino acid sequence of SEQ ID NO: 10 or 11 or an amino acid sequence that is at least 90%, at least 95%, at least 98% identical to SEQ ID NO:10 or 11.

In certain embodiments, the modified hinge is derived from IgG4 that includes one or more amino acid residues substituted with an amino acid residue different from that present in an unmodified hinge. The one or more substituted amino acid residues are selected from, but not limited to one or more amino acid residues at positions 220, 226, 228, 229, 230, 233, 234, 235, 234, 237, 238, 239, 243, 247, 267, 268, 280, 290, 292, 297, 298, 299, 300, 305, 309, 218, 326, 330, 331, 332, 333, 334, 336, 339, or a combination thereof.

In some embodiments, the modified hinge is derived from an IgG4 that includes, but is not limited to, one or more of the following amino acid residue substitutions: 220S, 226S, 228P, 229S, 230S, 233P, 234A, 234V, 234F, 234A, 235A, 235E, 236A, 237A, 238S, 239D, 243L, 247I, 267E, 268Q, 280H, 290S, 290E, 290N, 292P, 297A, 297Q, 298A, 298G, 298D, 298V, 299A, 300L, 305I, 309L, 318A, 326A, 326W, 326E, 328F, 330L, 330S, 331S, 331S, 332E, 333A, 333S, 333S, 334A, 339D, 339Q, 396L, or a combination thereof, wherein the amino acid in the unmodified hinge is substituted with the above identified amino acids at the indicated position. In one instance the sequence includes the following amino acid changes S228P, L235E and N297Q.

For amino acid positions in immunoglobulin discussed herein, numbering is according to the EU index or EU numbering scheme (Kabat et al. 1991 Sequences of Proteins of Immunological Interest, 5th Ed., United States Public Health Service, National Institutes of Health, Bethesda, hereby entirely incorporated by reference). The EU index or EU index as in Kabat or EU numbering scheme refers to the numbering of the EU antibody (Edelman et al. 1969 Proc Natl Acad Sci USA 63:78-85).

The hinge/linker region can also comprise a IgG4 hinge region having the sequence ESKYGPPCPSCP (SEQ ID NO:4) or ESKYGPPCPPCP (SEQ ID NO:3).

The hinge/linger region can also comprise the sequence ESKYGPPCPPCP (SEQ ID NO:3) followed by the linker sequence GGGSSGGGSG (SEQ ID NO:2) followed by IgG4 CH3 sequence GQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO:12). Thus, the entire linker/spacer region can comprise the sequence: ESKYGPPCPPCPGGGSSGGGSGGQPREPQVYTLPPSQEEMTKNQVSLTCLVKGFY PSDIAVEWESNGQPENNYKTTPPVLDSDGSFFLYSRLTVDKSRWQEGNVFSCSVMHEALHNHYTQKSLSLSLGK (SEQ ID NO:11). In some cases the spacer has 1, 2, 3, 4, or 5 single amino acid changes (e.g., conservative changes) compared to SEQ ID NO:11. In some cases, the IgG4 Fc hinge/linker region that is mutated at two positions (L235E; N297Q) in a manner that reduces binding by Fc receptors (FcRs).

Transmembrane Region

A variety of transmembrane domains can be used in the. Table 2 includes examples of suitable transmembrane domains. Where a spacer region is present, the transmembrane domain is located carboxy terminal to the spacer region.

TABLE 2

Examples of Transmembrane Domains

| Name | Accession | Length | Sequence |
|---|---|---|---|
| CD3z | J04132.1 | 21 aa | LCYLLDGILFIYGVILTALFL (SEQ ID NO: 13) |
| CD28 | NM_006139 | 27 aa | FWVLVVVGGVLACYSLLVTVAF IIFWV (SEQ ID NO: 14) |
| CD28(M) | NM_006139 | 28 aa | MFWVLVVVGGVLACYSLLVTVAF IIFWV (SEQ ID NO: 15) |
| CD4 | M35160 | 22 aa | MALIVLGGVAGLLLFIGLGIFF (SEQ ID NO: 16) |

TABLE 2-continued

Examples of Transmembrane Domains

| Name | Accession | Length | Sequence |
|---|---|---|---|
| CD8tm | NM_001768 | 21 aa | IYIWAPLAGTCGVLLLSLVIT (SEQ ID NO: 17) |
| CD8tm2 | NM_001768 | 23 aa | IYIWAPLAGTCGVLLLSLVITLY (SEQ ID NO: 18) |
| CD8tm3 | NM_001768 | 24 aa | IYIWAPLAGTCGVLLLSLVITLYC (SEQ ID NO: 19) |
| 41BB | NM_001561 | 27 aa | IISFFLALTSTALLFLLFFLTLRFSVV (SEQ ID NO: 20) |

Costimulatory Domain

The costimulatory domain can be any domain that is suitable for use with a CD3ξ signaling domain. In some cases the costimulatory domain is a CD28 costimulatory domain that includes a sequence that is at least 90%, at least 95%, at least 98% identical to or identical to: RSKRSRGGHSDYMNMTPRRPGPTRKHYQPYAPPRD-FAAYRS (SEQ ID NO:23; LL to GG amino acid change double underlined). In some cases the CD28 co-signaling domain has 1, 2, 3, 4 of 5 amino acid changes (preferably conservative and preferably not in the underlined GG sequence) compared to SEQ ID NO:23. In some cases the co-signaling domain is a 4-1BB co-signaling domain that includes a sequence that is at least 90%, at least 95%, at least 98% identical to or identical to: KRGRKKLLY-IFKQPFMRPVQTTQEEDGCSCRFPEEEEGGCEL (SEQ ID NO:24). In some cases the 4-1BB co-signaling domain has 1, 2, 3, 4 of 5 amino acid changes (preferably conservative) compared to SEQ ID NO:24.

The costimulatory domain(s) are located between the transmembrane domain and the CD3ζ signaling domain. Table 3 includes examples of suitable costimulatory domains together with the sequence of the CD3ζ signaling domain.

TABLE 3

CD3ζ Domain and Examples of Costimulatory Domains

| Name | Accession | Length | Sequence |
|---|---|---|---|
| CD3ζ | J04132.1 | 113 aa | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR (SEQ ID NO: 21) |
| CD28 | NM_006139 | 42 aa | RSKRSRLLHSDYMNMTPRRPGPTRKHYQPYAPPRDFAAYRS (SEQ ID NO: 22) |
| CD28gg* | NM_006139 | 42 aa | RSKRSRGGHSDYMNMTPRRPGPTRKHYQPYAPPRDFAAYRS (SEQ ID NO: 23) |
| 41BB | NM_001561 | 42 aa | KRGRKKLLYIFKQPFMRPVQTTQEEDGCSCRFPEEEEGGCEL (SEQ ID NO: 24) |

TABLE 3-continued

CD3ζ Domain and Examples of Costimulatory Domains

| Name | Accession | Length | Sequence |
|---|---|---|---|
| OX40 | | 42 aa | ALYLLRRDQRLPPDAHKPPGGGSFRTPIQEEQADAHSTLAKI (SEQ ID NO: 25) |

In various embodiments: the costimulatory domain is selected from the group consisting of: a costimulatory domain depicted in Table 3 or a variant thereof having 1-5 (e.g., 1 or 2) amino acid modifications, a CD28 costimulatory domain or a variant thereof having 1-5 (e.g., 1 or 2) amino acid modifications, a 4-1BB costimulatory domain or a variant thereof having 1-5 (e.g., 1 or 2) amino acid modifications and an OX40 costimulatory domain or a variant thereof having 1-5 (e.g., 1 or 2) amino acid modifications. In certain embodiments, a 4-1BB costimulatory domain or a variant thereof having 1-5 (e.g., 1 or 2) amino acid modifications in present. In some embodiments there are two costimulatory domains, for example a CD28 co-stimulatory domain or a variant thereof having 1-5 (e.g., 1 or 2) amino acid modifications (e.g., substitutions) and a 4-1BB co-stimulatory domain or a variant thereof having 1-5 (e.g., 1 or 2) amino acid modifications (e.g., substitutions). In various embodiments the 1-5 (e.g., 1 or 2) amino acid modification are substitutions. The costimulatory domain is amino terminal to the CD3ζ signaling domain and in some cases a short linker consisting of 2-10, e.g., 3 amino acids (e.g., GGG) is positioned between the costimulatory domain and the CD3ζ signaling domain.

CD3ζ Signaling Domain

The CD3ζ Signaling domain can be any domain that is suitable for use with a CD3ζ signaling domain. In some cases the CD3ζ signaling domain includes a sequence that is at least 90%, at least 95%, at least 98% identical to or identical to: RVKFSRSADAPAYQQGQNQLYNELNLGR-REEYDVLDKRRGRDPEMGGKPRRK NPQEGLY-NELQKDKMAEAYSEIGMKGERRRGKGHDGLYQGL-STATKDTYDAL HMQALPPR (SEQ ID NO:21). In some cases the CD3ζ signaling has 1, 2, 3, 4 of 5 amino acid changes (preferably conservative) compared to SEQ ID NO:21.

Truncated EGFR

The CD3ζ signaling domain can be followed by a ribosomal skip sequence (e.g., LEGGGEGRGSLLTCGD-VEENPGPR; SEQ ID NO:27) and a truncated EGFR having a sequence that is at least 90%, at least 95%, at least 98% identical to or identical to: LVTSLLLCELPHPAFLLIP-RKVCNGIGIGEFKDSLSINATNIKHFKNCTSISGDLHIL PVAFRGDSFTHTPPLDPQELDI-LKTVKEITGFLLIQAWPENRTDLHAFENLEIIRGR TKQHGQFSLAVVSLNITSLGLRSLKEISDGDVIIS-GNKNLCYANTINWKKLFGTSG QKTKIISNRGENSCK-ATGQVCHALCSPEGCWGPEPRDCVSCRNVSR-GRECVDKC NLLEGEPREFVENSECIQCHPECLPQAMNITCT-GRGPDNCIQCAHYIDGPHCVKT CPAGVM-GENNTLVWKYADAGHVCHLCHPNCTYGCTGPG-LEGCPTNGPKIPSIA TGMVGALLLLLVVALGIGLFM (SEQ ID NO:28). In some cases the truncated EGFR has 1, 2, 3, 4 of 5 amino acid changes (preferably conservative) compared to SEQ ID NO:28.

CS1 CAR

The CS1 CAR can include a sequence that is at least 90%, at least 95%, at least 98% identical to or identical to the amino acid sequence depicted in FIG. 2, FIG. 6, FIG. 7, FIG. 8. FIG. 9 or FIG. 10 (SEQ ID Nos: 29-46; either including or excluding the GMCSFRa signal sequence and either including or excluding the T2A ribosomal skip sequence and the truncated EGFRt).

Among the CAR targeting CS1 described herein are those summarized in Table 4 in which the spacer region, transmembrane domain and costimulatory domain(s) for each CAR are indicated.

TABLE 4

Examples of CAR Targeting CS1

| Name | SEQ ID NO* | FIG. | Spacer | TM | Costimulatory Domain(s) |
|---|---|---|---|---|---|
| CS1scFv-IgG4(HL-CH3)-CD28tm-CD28gg-Zeta-T2A-EGFRt. | 29//30//31 | 2 | IgG4(HL-CH3) | CD28 | CD28GG |
| CS1scFv-IgG4(HL-CH3)-CD4tm-41BB-Zeta-T2A-EGFRt. | 32//33//34 | 6 | IgG4(HL-CH3) | CD4 | 4-1BB |
| CS1qscFv-IgG4(L235E, N297Q)-CD4tm-41BB-Zeta-T2A-EGFRt. | 35//36//37 | 7 | IgG4(L235E, N297Q) | CD4 | 4-1BB |
| CS1scFv-IgG4(L235E, N297Q)-CD28tm-CD28gg-Zeta-T2A-EGFRt | 38//39//40 | 8 | IgG4(L235E, N297Q) | CD28 | CD28GG |
| CS1scFv-Linker-CD4tm-41BB-Zeta-T2A-EGFRt. | 41//42//43 | 9 | L | CD4 | 4-1BB |
| CS1scFv-Linker-CD28tm-CD28gg-Zeta-T2A-EGFRt | 44//45//46 | 10 | L | CD28 | CD28GG |

*SEQ ID NOs for: entire sequence depicted including GMCSFRa signal sequence, T2A and EGFRt//sequence including GMCSFRa signal sequence but excluding T2A and EGFRt//sequence for sequence excluding GMCSFRa signal sequence, T2A and EGFRt.

DESCRIPTION OF DRAWINGS

FIG. 2 depicts the amino acid sequence of a CS1 CAR that includes signal peptide, a ribosomal skip sequence and an EGFRt (SEQ ID NO:29).

FIG. 6 depicts the amino acid sequence of CS1scFv-IgG4(HL-CH3)-CD4tm-41BB-Zeta-T2A-EGFRt (SEQ ID NO:32).

FIG. 7 depicts the amino acid sequence of CS1scFv-IgG4(L235E,N297Q)-CD4tm-41BB-Zeta-T2A-EGFRt (SEQ ID NO:35).

FIG. 8 depicts the amino acid sequence of CS1scFv-IgG4(L235E, N297Q)-CD28tm-CD28gg-Zeta-T2A-EGFRt (SEQ ID NO:38).

FIG. 9 depicts the amino acid sequence of CS1scFv-Linker-CD4tm-41BB-Zeta-T2A-EGFRt (SEQ ID NO:41).

FIG. 10 depicts the amino acid sequence of CS1scFv-Linker-CD28tm-CD28gg-Zeta-T2A-EGFRt (SEQ ID NO:44).

FIGS. 11A-11E are the complete nucleotide sequence of CS1scFv-IgG4(HL-CH3)-CD28gg-Zeta-T2A-EGFRt_epHIV7 (SEQ ID NO: 47).

FIG. 6 (CH2 4IBB); FIG. 8 (EQ CD28); FIG. 7 (EQ 4IBB); FIG. 10 (L CD28) and FIG. 9 (L CD4 IBB).

DETAILED DESCRIPTION

Figure 1:
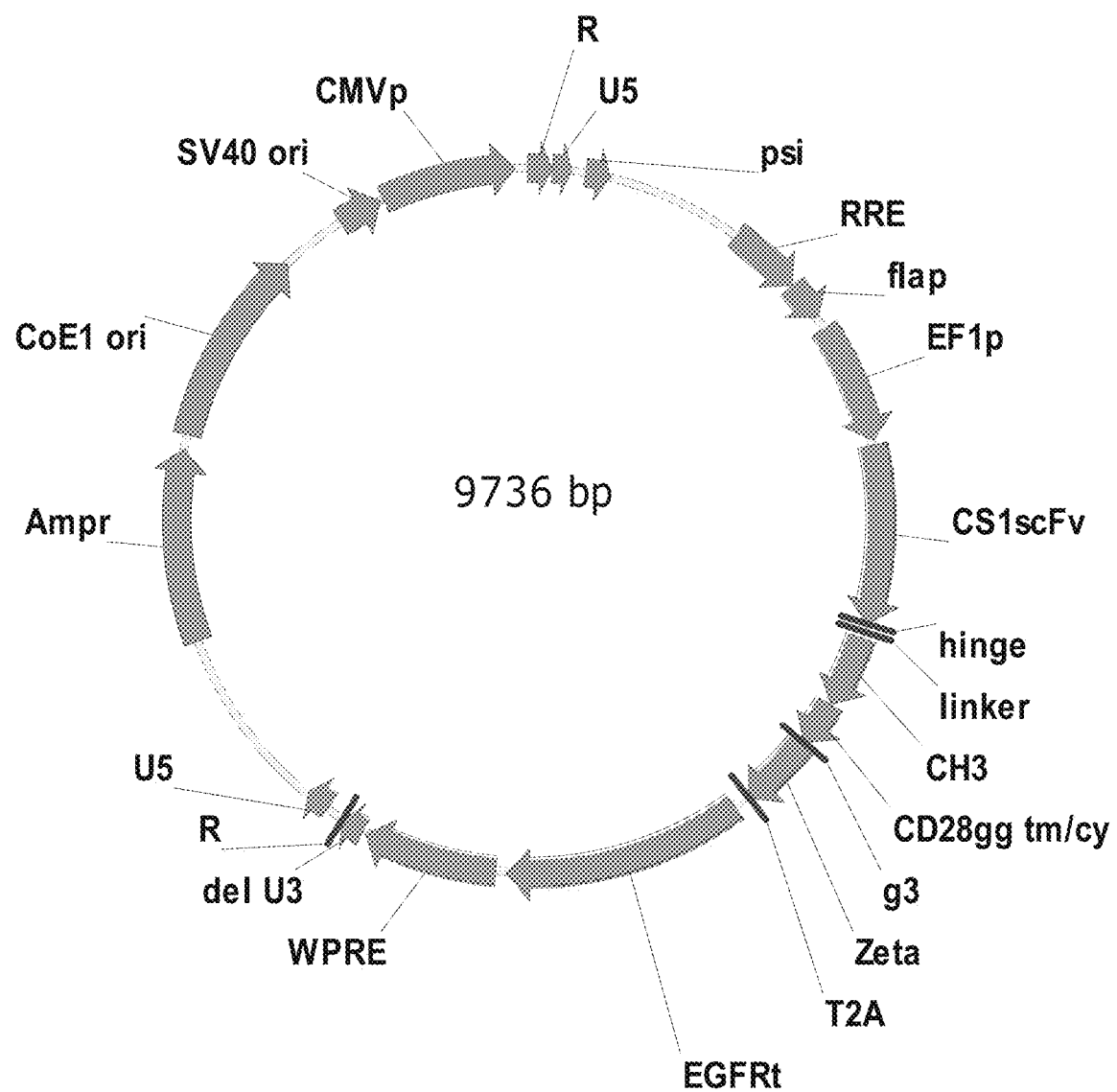
FIG. 1 is a schematic depiction of a CS1 CAR expressing lentiviral vector (CS1scFv-IgG4(HL-CH3)-CD28gg-Zeta(CO)-T2A-EGFRt_epHIV7). The CS1 CAR construct includes: a GMCSF signal sequence, CS1 scFv, IgG4 hinge region, linker, CH3 domain, a CD28 co-stimulatory domain and CD3ζ Signaling domain. The CAR construct is followed by a T2A ribosomal skip sequence, and then suicide gene EGFRt coding sequence. The CAR and EGFRt molecules are expressed from a single transcript.

Described below is the structure, construction and characterization of several CS1-specific chimeric antigen receptors ("CAR"). A CAR is a recombinant biomolecule that contains an extracellular recognition domain, a transmembrane region, and an intracellular signaling domain. The term "antigen," therefore, is not limited to molecules that bind antibodies, but to any molecule that can bind specifically to any receptor. "Antigen" thus refers to the recognition domain of the CAR. The extracellular recognition domain (also referred to as the extracellular domain or simply by the recognition element which it contains) comprises a recognition element that specifically binds to a molecule present on the cell surface of a target cell. The transmembrane region anchors the CAR in the membrane. The intracellular signaling domain comprises the signaling domain from the zeta chain of the human CD3 complex and optionally comprises one or more co-stimulatory signaling domains. CARs can both to bind antigen and transduce T cell activation, independent of MHC restriction. Thus, CARs are "universal" immunoreceptors which can treat a population of patients with antigen-positive tumors irrespective of their HLA genotype. Adoptive immunotherapy using T lymphocytes that express a tumor-specific CAR can be a powerful therapeutic strategy for the treatment of cancer.

In some cases, the CS1 CAR can be produced using a vector in which the CAR open reading frame is followed by a T2A ribosome skip sequence and a truncated EGFR (EGFRt), which lacks the cytoplasmic signaling tail. In this arrangement, co-expression of EGFRt provides an inert, non-immunogenic surface marker that allows for accurate measurement of gene modified cells, and enables positive selection of gene-modified cells, as well as efficient cell tracking of the therapeutic T cells in vivo following adoptive transfer. Efficiently controlling proliferation to avoid cytokine storm and off-target toxicity is an important hurdle for the success of T cell immunotherapy. The EGFRt incorporated in the CS1CAR lentiviral vector can act as suicide gene to ablate the CAR+ T cells in cases of treatment-related toxicity.

The CAR described herein can be produced by any means known in the art, though preferably it is produced using recombinant DNA techniques. Nucleic acids encoding the several regions of the chimeric receptor can be prepared and assembled into a complete coding sequence by standard techniques of molecular cloning known in the art (genomic library screening, overlapping PCR, primer-assisted ligation, site-directed mutagenesis, etc.) as is convenient. The resulting coding region is preferably inserted into an expression vector and used to transform a suitable expression host cell line, preferably a T lymphocyte cell line, and most preferably an autologous T lymphocyte cell line.

Various T cell subsets isolated from the patient can be transduced with a vector for CAR expression. Central memory T cells are one useful T cell subset. Central memory T cell can be isolated from peripheral blood mononuclear cells (PBMC) by selecting for CD45RO+/CD62L+ cells, using, for example, the CliniMACS® device to immunomagnetically select cells expressing the desired receptors. The cells enriched for central memory T cells can be activated with anti-CD3/CD28, transduced with, for example, a lentiviral vector that directs the expression of an CS1 CAR as well as a non-immunogenic surface marker for in vivo detection, ablation, and potential ex vivo selection. The activated/genetically modified CS1 central memory T cells can be expanded in vitro with IL-2/IL-15 and then cryopreserved.

Example 1: Construction and Structure of epHIV7 Used for Expression of CS1-Specific CAR The pHIV7 plasmid is a parent plasmid from which the clinical vectors expressing a CS1 CAR can be derived. The epHIV7 vector used for expression of the CAR was produced from pHIV7 vector (Wang et al. 2011 Blood 118: 1255). Importantly, this vector uses the human EF1 promoter to drive expression of the CAR. Both the 5' and 3' sequences of the vector were derived from pv653RSN as previously derived from the HXBc2 provirus. The polypurine tract DNA flap sequences (cPPT) were derived from HIV-1 strain pNL4-3 from the NIH AIDS Reagent Repository.

Construction of pHIV7 was carried out as follows. Briefly, pv653RSN, containing 653 bp from gag-pol plus 5' and 3' long-terminal repeats (LTRs) with an intervening SL3-neomycin phosphotransferase gene (Neo), was subcloned into pBluescript, as follows: In Step 1, the sequences from 5' LTR to rev-responsive element (RRE) made p5'HIV-1 51, and then the 5' LTR was modified by removing sequences upstream of the TATA box, and ligated first to a CMV enhancer and then to the SV40 origin of replication (p5'HIV-2). In Step 2, after cloning the 3' LTR into pBluescript to make p3'HIV-1, a 400-bp deletion in the 3' LTR enhancer/promoter was made to remove cis-regulatory elements in HIV U3 and form p3'HIV-2. In Step 3, fragments isolated from the p5'HIV-3 and p3'HIV-2 were ligated to make pHIV-3. In Step 4, the p3'HIV-2 was further modified by removing extra upstream HIV sequences to generate p3'HIV-3 and a 600-bp BamHI-SalI fragment containing WPRE was added to p3'HIV-3 to make the p3'HIV-4. In Step 5, the pHIV-3 RRE was reduced in size by PCR and ligated to a 5' fragment from pHIV-3 (not shown) and to the p3'HIV-4, to make pHIV-6. In Step 6, a 190-bp BglII-BamHI fragment containing the cPPT DNA flap sequence from HIV-1 pNL4-3 (55) was amplified from pNL4-3 and placed between the RRE and the WPRE sequences in pHIV6 to make pHIV-7. This parent plasmid pHIV7-GFP (GFP, green fluorescent protein) was used to package the parent vector using a four-plasmid system.

A packaging signal, psi w, is required for efficient packaging of viral genome into the vector. The RRE and WPRE enhance the RNA transcript transport and expression of the transgene. The flap sequence, in combination with WPRE, has been demonstrated to enhance the transduction efficiency of lentiviral vector in mammalian cells.

The helper functions, required for production of the viral vector, are divided into three separate plasmids to reduce the probability of generation of replication competent lentivirus via recombination: 1) pCgp encodes the gag/pol protein required for viral vector assembly; 2) pCMV-Rev2 encodes the Rev protein, which acts on the RRE sequence to assist in the transportation of the viral genome for efficient packaging; and 3) pCMV-G encodes the glycoprotein of the vesiculo-stomatitis virus (VSV), which is required for infectivity of the viral vector.

There is minimal DNA sequence homology between the pHIV7 encoded vector genome and the helper plasmids. The regions of homology include a packaging signal region of approximately 600 nucleotides, located in the gag/pol sequence of the pCgp helper plasmid; a CMV promoter sequence in all three helper plasmids; and a RRE sequence in the helper plasmid pCgp. It is highly improbable that replication competent recombinant virus could be generated due to the homology in these regions, as it would require multiple recombination events. Additionally, any resulting recombinants would be missing the functional LTR and tat sequences required for lentiviral replication.

The CMV promoter was replaced by the EF1α-HTLV promoter (EF1p), and the new plasmid was named epHIV7. The EF1p has 563 bp and was introduced into epHIV7 using NruI and NheI, after the CMV promoter was excised.

The lentiviral genome, excluding gag/pol and rev that are necessary for the pathogenicity of the wild-type virus and are required for productive infection of target cells, has been removed from this system. In addition, epHIV7 vector construct does not contain an intact 3'LTR promoter, so the resulting expressed and reverse transcribed DNA proviral genome in targeted cells will have inactive LTRs. As a result of this design, no HIV-I derived sequences will be transcribed from the provirus and only the therapeutic sequences will be expressed from their respective promoters. The removal of the LTR promoter activity in the SIN vector is expected to significantly reduce the possibility of unintentional activation of host genes. Table 5 summarizes the various regulator elements present in epHIV7.

FIG. 1 is a schematic depiction of CS1 CAR (CS1scFv-IgG4(HL-CH3)-CD28gg-Zeta(CO)-T2A-EGFRt_epHIV7), a lentiviral vector containing the CAR construct composed of CS1 scFv, IgG4 hinge region, linker, a CD28 costimulatory domain and CD3ζ Signaling domain. The CAR construct is followed by a T2A ribosomal skip sequence, and then suicide gene EGFRt coding sequence. The CAR and EGFRt molecules are expressed from a single transcript. The entire nucleotide sequence of the vector is presented in FIGS. 11A-11E and Table 5 presents position of various elements of the vector.

TABLE 5

Functional elements of CS1 CAR_epHIV7

| Regulatory Elements and Genes | Location (Nucleotide Numbers) | Comments |
|---|---|---|
| U5 | 87-171 | 5' Unique sequence |
| psi | 233-345 | Packaging signal |
| RRE | 957-1289 | Rev-responsive element |
| flap | 1290-1466 | Contains polypurine track sequence and central termination sequence to facilitate nuclear import of pre-integration complex |
| EF1p Promoter | 1524-2067 | EF1-alpha Eukaryotic Promoter sequence driving expression of CD19Rop |
|  | 2084-4963 | Therapeutic insert |
| WPRE | 5011-5611 | Woodchuck hepatitis virus derived regulatory element to enhance viral RNA transportation |
| delU3 | 5626-5730 | 3' U3 with deletion to generate SIN vector |
| R | 5731-5811 | Repeat sequence within LTR |
| U5 | 5812-5925 | 3' U5 sequence in LTR |
| $Amp^R$ | 6761-7619 | Ampicillin-resistance gene |

TABLE 5-continued

Functional elements of CS1 CAR_epHIV7

| Regulatory Elements and Genes | Location (Nucleotide Numbers) | Comments |
|---|---|---|
| CoE1 ori | 7682-8563 | Replication origin of plasmid |
| SV40 ori | 8860-=9059 | Replication origin of SV40 |
| CMV promoter | 9073-9672 | CMV promoter to generate viral genome RNA |
| R | 9728-86 | Repeat sequence within LTR |

Example 2: Production of Vectors for Transduction of Patient T Cells

For each plasmid (CS1 CAR_epHIV7; pCgp; pCMV-G; and pCMV-Rev2), a seed bank is generated, which is used to inoculate the fermenter to produce sufficient quantities of plasmid DNA. The plasmid DNA is tested for identity, sterility and endotoxin prior to its use in producing lentiviral vector.

Briefly, cells are expanded from the 293T working cell (WCB), which has been tested to confirm sterility and the absence of viral contamination. A vial of 293T cells from the 293T WCB is thawed. Cells are grown and expanded until sufficient numbers of cells existed to plate an appropriate number of 10 layer cell factories (CFs) for vector production and cell train maintenance. A single train of cells can be used for production.

The lentiviral vector was produced in sub-batches of up to 10 CFs. Two subbatches can be produced in the same week leading to the production of approximately 20 L of lentiviral supernatant/week. The material produced from all sub-batches were pooled during the downstream processing phase, in order to produce one lot of product. 293T cells were plated in CFs in 293T medium (DMEM with 10% FBS). Factories were placed in a 37° C. incubator and horizontally leveled in order to get an even distribution of the cells on all the layers of the CF. Two days later, cells were transfected with the four lentiviral plasmids described above using the CaPO4 method, which involves a mixture of Tris:EDTA, 2M CaCl2, 2×RBS, and the four DNA plasmids. Day 3 after transfection, the supernatant containing secreted lentiviral vectors was collected, purified and concentrated. After the supernatant was removed from the CFs, End-of-Production Cells were collected from each CF. Cells were trypsinized from each factory and collected by centrifugation. Cells were resuspended in freezing medium and cryopreserved. These cells were later used for replication-competent lentivirus (RCL) testing.

To purify and formulate vectors crude supernatant was clarified by membrane filtration to remove the cell debris. The host cell DNA and residual plasmid DNA were degraded by endonuclease digestion (Benzonase®). The viral supernatant was clarified of cellular debris using a 0.45 μm filter. The clarified supernatant was collected into a pre-weighed container into which the Benzonase® is added (final concentration 50 U/mL). The endonuclease digestion for residual plasmid DNA and host genomic DNA as performed at 37° C. for 6 h. The initial tangential flow ultra-filtration (TFF) concentration of the endonuclease-treated supernatant was used to remove residual low molecular weight components from the crude supernatant, while concentrating the virus ~20 fold. The clarified endonuclease-treated viral supernatant was circulated through a hollow fiber cartridge with a NMWCO of 500 kD at a flow rate designed to maintain the shear rate at ~4,000 sec-1 or less, while maximizing the flux rate. Diafiltration of the nuclease-treated supernatant was initiated during the concentration process to sustain the cartridge performance. An 80% permeate replacement rate was established, using 4% lactose in PBS as the diafiltration buffer. The viral supernatant was brought to the target volume, representing a 20-fold concentration of the crude supernatant, and the diafiltration was continued for 4 additional exchange volumes, with the permeate replacement rate at 100%.

Further concentration of the viral product was accomplished by using a high speed centrifugation technique. Each sub-batch of the lentivirus was pelleted using a Sorvall RC-26 plus centrifuge at 6000 RPM (6,088 RCF) at 6° C. for 16-20 h. The viral pellet from each sub-batch was then reconstituted in a 50 mL volume with 4% lactose in PBS. The reconstituted pellet in this buffer represents the final formulation for the virus preparation. The entire vector concentration process resulted in a 200-fold volume reduction, approximately. Following the completion of all of the sub-batches, the material was then placed at −80° C., while samples from each sub-batch were tested for sterility. Following confirmation of sample sterility, the sub-batches were rapidly thawed at 37° C. with frequent agitation. The material was then pooled and manually aliquoted in the Class II Type A/B3 biosafety cabinet in the viral vector suite. A fill configuration of 1 mL of the concentrated lentivirus in sterile USP class 6, externally threaded O-ring cryovials was used. Center for Applied Technology Development (CATD)'s Quality Systems (QS) at COH released all materials according to the Policies and Standard Operating Procedures for the CBG and in compliance with current Good Manufacturing Practices (cGMPs).

To ensure the purity of the lentiviral vector preparation, it is tested for residual host DNA contaminants, and the transfer of residual host and plasmid DNA. Among other tests, vector identity is evaluated by RT-PCR to ensure that the correct vector is present. All release criteria are met for the vector intended for use in this study.

Example 3: Preparation of Tcm Cells Suitable for Use in ACT

T lymphocytes are obtained from a patient by leukopheresis, and the appropriate allogenic or autologous T cell subset, for example, Central Memory T cells (Tcm), are genetically altered to express the CAR, then administered back to the patient by any clinically acceptable means, to achieve anticancer therapy.

Tcm that are CD8+ are isolated essentially as described in Wang et al. (J Immunology 35:689, 2012). Briefly, on the day of leukapheresis, PBMC were isolated by density gradient centrifugation over Ficoll-Paque followed by two washes in PBS/EDTA. PBMC were then washed once in PBS, resuspended in X Vivo15 media containing 10% fetal calf serum (FCS), transferred to a 300 cc transfer bag, and stored on a 3-D rotator overnight at room temperature (RT). The following day, up to $5 \times 10^9$ PBMC were incubated in a 300 cc transfer bag with clinical grade anti-CD4 (2.5 mL), anti-CD14 (1.25 mL), and anti-CD45RA (2.5 mL) microbeads (Miltenyi Biotec) for 30 minutes at RT in X Vivo15 containing 10% FCS. CD4+, CD14+ and CD45RA+ cells were then immediately depleted using the CliniMACS™ depletion mode according to the manufacturer's instructions (Miltenyi Biotec). After centrifugation, the unlabeled negative fraction of cells was resuspended in CliniMACS™ PBS/EDTA buffer (Miltenyi Biotec) containing 0.5% human serum albumin (HSA) and then labeled with clinical grade biotinylated-DREG56 mAb (COHNMC CBG) at 0.1 mg/106 cells for 30 minutes at RT. The cells were then washed and resuspended in a final volume of 100 mL CliniMACS™ PBS/EDTA containing 0.5% HSA and transferred into a new 300 cc transfer bag. After 30 minutes incubation with 1.25 mL anti-biotin microbeads (Miltenyi Biotec), the CD62L+ fraction of PBMC (CD8+ TCM) was purified with positive selection on CliniMACS™ according to the manufacturer's instructions, and resuspended in X Vivo15 containing 10% FCS.

Tcm that are CD8+/CD4+ are prepared using a modification of the forgoing process by modifying the CD4+, CD14+ and CD45RA+ selection to a CD14+ and CD45RA+ selection. The method uses a two-step process on the CliniMACS™ device to first deplete CD14+ and CD45RA+ cells, then to positively select CD62L+ cells. This modified platform generates $50 \times 10^6$ bulk Tcm from a single leukapheresis.

Following enrichment, Tcm cells are formulated in complete X-Vivo15 plus 50 IU/mL IL-2 and 0.5 ng/mL IL-15 and transferred to a Teflon cell culture bag, where they are stimulated with Dynal ClinEx™ Vivo CD3/CD28 beads. Up to five days after stimulation, cells are transduced with lentiviral vector encoding CS1 CAR at a multiplicity of infection (MOI) of about 3. Cultures are maintained for up to 42 days with addition of complete X-Vivo15 and IL-2 and IL-15 cytokine as required for cell expansion (keeping cell density between $3 \times 10^5$ and $2 \times 10^6$ viable cells/mL, and cytokine supplementation every Monday, Wednesday and Friday of culture). Cells typically expand to approximately $10^9$ cells under these conditions within 21 days. At the end of the culture period cells are harvested, washed twice and formulated in clinical grade cryopreservation medium.

On the day(s) of T cell infusion, the cryopreserved and released product will be thawed, washed and formulated for re-infusion. The cryopreserved vials containing the released cell product will be removed from liquid nitrogen storage, thawed, cooled and washed with a PBS/2% human serum albumin (HSA) Wash Buffer. After centrifugation, the supernatant will be removed and the cells resuspended in a Preservative-Free Normal Saline (PFNS)/2% HSA infusion diluent. Samples will be removed for quality control testing.

Example 4: Amino acid Sequence of CS1 CAR (CS1scFv-IgG4(HL-CH3)-CD28tm-CD28gg-Zeta-T2A-EGFRt)

The complete amino acid sequence of CS1scFv-IgG4 (HL-CH3)-CD28tm-CD28gg-Zeta-T2A-EGFRt is depicted in FIG. 2. The entire sequence (SEQ ID NO:29) includes: a 22 amino acid GMCSF signal peptide (SEQ ID NO:26), a CS1 scFv sequence (SEQ ID NO:1); a IgG4 hinge sequence (SEQ ID NO:3; with amino acid substitutions S to P shaded); a 10 amino acid linker (SEQ ID NO:2); IgG4 CH3 sequence (SEQ ID NO:12); a 28 amino acid CD28 transmembrane domain sequence (SEQ ID NO:14); a CD28gg co-stimulatory domain sequence (SEQ ID NO:23; LL to GG amino acid changes highlighted); a 3 amino acid Gly linker; a 112 amino acid CD3ζ sequence (SEQ ID NO:21); a 24 amino acid T2A skip sequence (SEQ ID NO:27); and EGFRt sequence (SEQ ID NO:28).

Example 5: Activity of CS1 CAR

Figure 3:
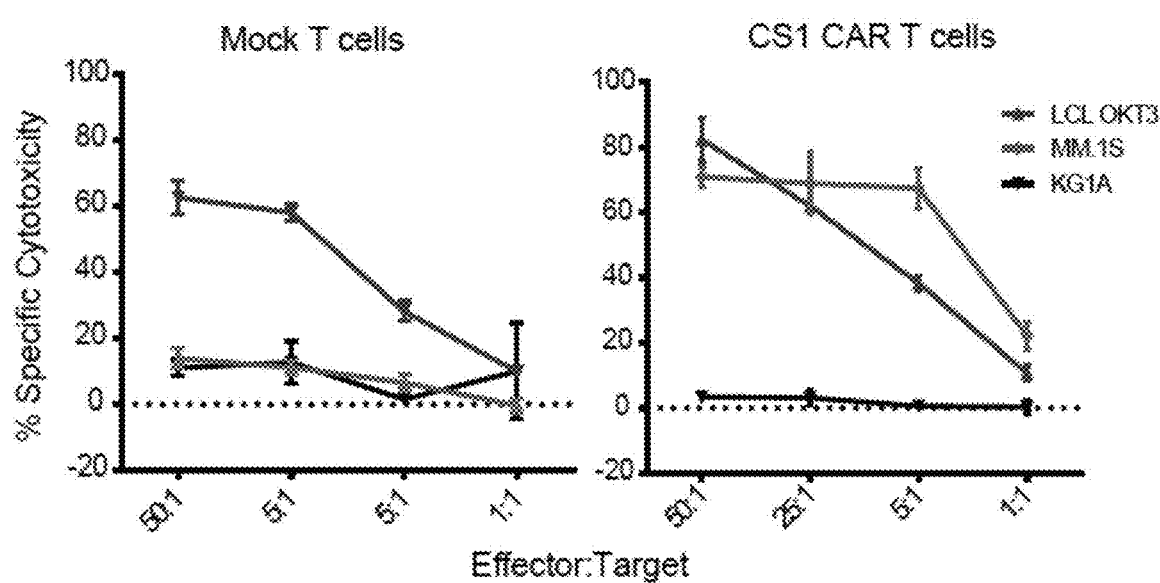
FIG. 3 is a pair of graphs depicting the results of studies showing that CS1 CAR re-directed Tcm exhibited cytotoxicity against MM cells. Cytotoxicity of the propagated CS1 CAR T cells was evaluated using 4-hour 51Cr release assays after co-culture with 51Cr-labeled target cells. OKT3 expressing LCLs were used as positive controls since they engage all TCRs, and CS1-negative AML cells (KG1a) were used as negative controls. CS1 CAR, but not un-engineered mock T cells showed specific cytotoxicity against MM cells.
Figure 4:
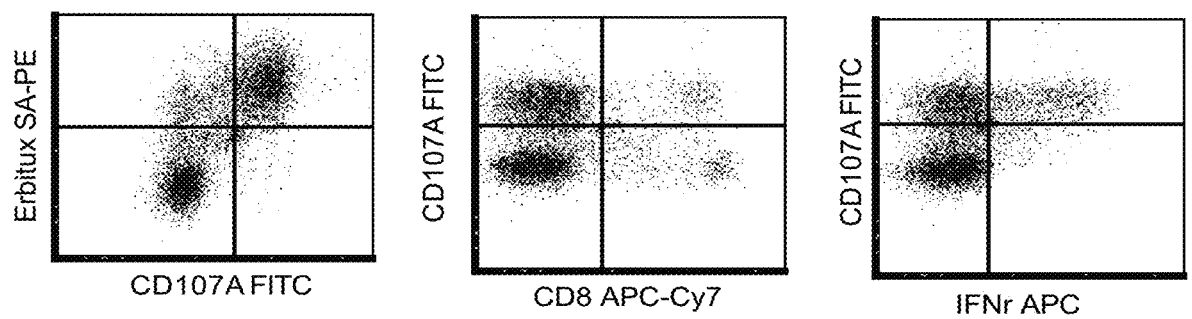
FIG. 4 depicts the results of studies showing that CS1 CAR re-directed Tcm cells exhibited effector function in response to stimulation of MM cells. CS1 CAR T cells ($10^5$) were co-cultured 6 hours in 96-well tissue culture plates with $10^5$ of MM.1S cells as stimulators. 107a degranulation and intracellular IFNgamma production were analyzed with flow cytometry. The majority of the CAR T cells identified by Erbitux were induced to degranulate after engagement with MM cells and IFNgamma positive cells were detected in respond to antigen stimulation.
Figure 5:
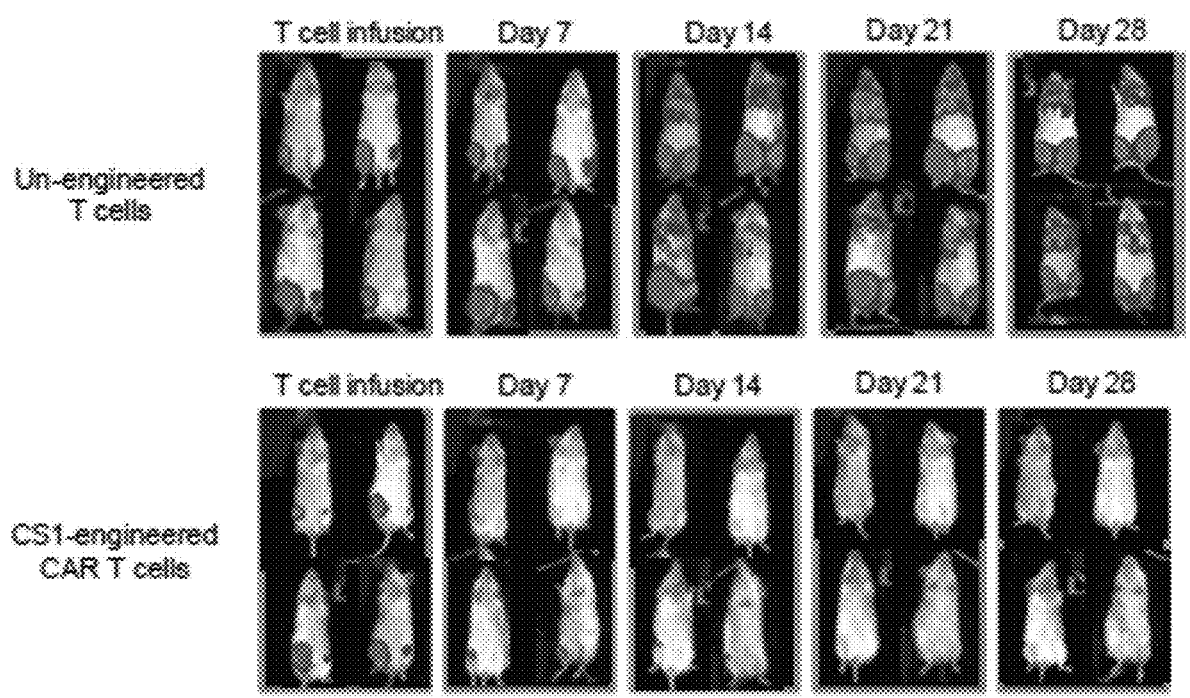
FIG. 5 depicts the results of studies showing that CS1 CAR re-directed Tcm cells eradicate multiple myeloma in vivo. Approximately $2\times10^6$ Firefly luciferase expressing MM.1S cells were inoculated into NSG mice via Intra-tibial injection. 7 days after tumor inoculation, $1\times10^6$ CS-1 CAR T cells were infused into the tumor bearing mice by intravenous injection. Tumor burdens were monitored with Xenogen® imaging once a week. Mice that received un-engineered cells were used as control. CS1 CAR T cells completely eradicated MM tumor 14 days post T cell infusion, while un-engineered T cells have no effects on tumor inhibition.

Cytotoxicity of the propagated CS1 CAR T cells expressing the CAR shown in FIG. 2 was evaluated using 4-hour 51Cr release assays after co-culture with 51Cr-labeled MM cells (MM.1S). As shown in FIG. 3, the engineered CS1 CART cells exhibit specific and efficient killing of MM cells, while un-transduced mock T cells has no cytocoxicity to MM cells. When co-cultured with MM cells, the engineered CS1 CAR Tcm-mediated strong effector function as indicated by 107a degranulation and IFNgamma as shown in FIG. 4. Upon adoptively transferred into MM tumor bearing NSG mice, the CS1 specific T cells exhibited efficient antitumor activity as shown in FIG. 5.

Figure 12:
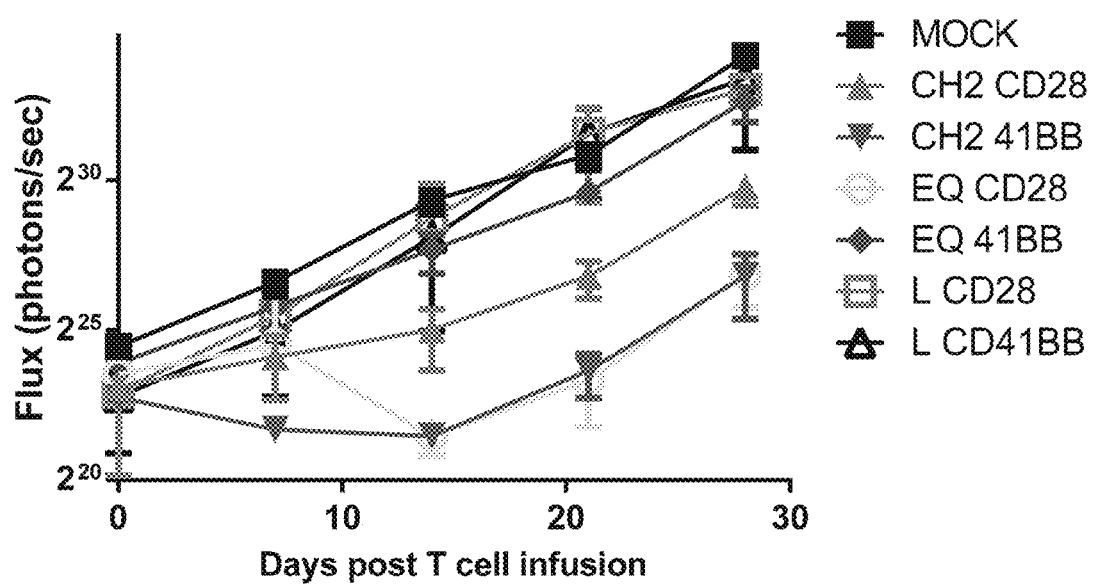
FIG. 12 depicts the results of studies showing that CS1 CAR re-directed Tcm cells eradicate multiple myeloma in vivo. 2×106 GFPffluc+ MM.1S cells were inoculated via Intra-tibial injection into NSG mice on day −7. 1×106 central memory T cell (Tcm) derived CS1 CAR+ T cells were intravenously infused into the tumor bearing mice on day 0. Mice received no T cells or un-transduced Tcm from the same donor were used as negative controls. Tumor signals were monitored by biophotonic imaging. Means±SEM of phonton/sec from multiple mice are depicted. The CAR were those of FIG. 2 (CH2 CD28)

In another study with additional CS1 CAR (FIG. 2 and FIGS. 6-10) $2\times10^6$ GFPffluc+MM.1S cells were inoculated via Intra-tibial injection into NSG mice on day $-7. 1\times10^6$ central memory T cell (Tcm) derived CS1 CAR+ T cells were intravenously infused into the tumor bearing mice on day 0. Mice received no T cells or un-transduced Tcm from the same donor were used as negative controls. Tumor signals were monitored by biophotonic imaging. Means±SEM of phonton/sec from multiple mice are depicted. The results of this analysis are shown in FIG. 12.

What is claimed is:

1. A chimeric antigen receptor (CAR) or polypeptide comprising the amino acid sequence of any of SEQ ID NOs: 29, 30, 31, 32, 33, 34, 38, 39, and 40.

2. The CAR or polypeptide of claim 1, wherein the chimeric antigen receptor or polypeptide comprises the amino acid sequence of any of SEQ ID NOs: 29, 30, and 31.

3. The CAR or polypeptide of claim 1, wherein the chimeric antigen receptor or polypeptide comprises the amino acid sequence of any of SEQ ID NOs: 32, 33, and 34.

4. The CAR or polypeptide of claim 1, wherein the chimeric antigen receptor or polypeptide comprises the amino acid sequence of any of SEQ ID NOs: 38, 39, and 40.

5. A method of treating a CS1-expressing cancer comprising administering to a patient in need thereof a pharmaceutical composition comprising a population of human T cells expressing the CAR or polypeptide of claim 1.

6. The method of claim 5 wherein the population of human T cells are autologous to the patient.

7. The method of claim 5 wherein the population of human T cells are allogenic to the patient.

8. The method of claim 5, wherein the human T cells are prepared by a method comprising obtaining T cells from the patient or obtaining T cells allogenic to the patient, isolating from the obtained T cells a population of cells enriched for CD4+/CD8+ central memory T cells, and transducing at least a portion of the isolated population of cells to with a viral vector encoding a chimeric antigen receptor or polypeptide, wherein chimeric antigen receptor or polypeptide comprising the amino acid sequence of any of SEQ ID NOs: 29, 30, 31, 32, 33, 34, 38, 39, and 40.

9. The method of claim 5, wherein the cancer is multiple myeloma.

* * * * *